United States Patent
Breinlinger et al.

(10) Patent No.: US 12,162,006 B2
(45) Date of Patent: Dec. 10, 2024

(54) ISOLATING MICROFLUIDIC STRUCTURES AND TRAPPING BUBBLES

(71) Applicants: Keith Joseph Breinlinger, San Rafael, CA (US); Eric D. Hobbs, Livermore, CA (US); Dorian Liepmann, Lafayette, CA (US); Joshua Tanner Nevill, El Cerrito, CA (US); Mark P. White, San Francisco, CA (US); Maria Jimena Loureiro, Albany, CA (US)

(72) Inventors: Keith Joseph Breinlinger, San Rafael, CA (US); Eric D. Hobbs, Livermore, CA (US); Dorian Liepmann, Lafayette, CA (US); Joshua Tanner Nevill, El Cerrito, CA (US); Mark P. White, San Francisco, CA (US); Maria Jimena Loureiro, Albany, CA (US)

(73) Assignee: BRUKER CELLULAR ANALYSIS, INC., Emeryville, CA (US)

( * ) Notice: Subject to any disclaimer, the term of this patent is extended or adjusted under 35 U.S.C. 154(b) by 767 days.

(21) Appl. No.: 15/634,097

(22) Filed: Jun. 27, 2017

(65) Prior Publication Data
US 2018/0071730 A1 Mar. 15, 2018

Related U.S. Application Data

(63) Continuation of application No. 14/732,682, filed on Jun. 6, 2015, now abandoned.

(60) Provisional application No. 62/176,890, filed on Jun. 6, 2014.

(51) Int. Cl.
*B01L 3/00* (2006.01)
*C12M 3/06* (2006.01)

(52) U.S. Cl.
CPC ........... *B01L 3/5027* (2013.01); *C12M 23/16* (2013.01); *B01L 2200/0647* (2013.01); *B01L 2200/0684* (2013.01); *B01L 2300/0864* (2013.01); *B01L 2300/0883* (2013.01); *B01L 2400/086* (2013.01); *Y10T 436/2575* (2015.01)

(58) Field of Classification Search
None
See application file for complete search history.

(56) References Cited

U.S. PATENT DOCUMENTS

| | | |
|---|---|---|
| 6,294,063 B1 | 9/2001 | Becker et al. |
| 6,379,929 B1 | 4/2002 | Burns et al. |
| 6,565,727 B1 | 5/2003 | Shenderov |
| 6,942,776 B2 | 9/2005 | Medoro |
| 6,958,132 B2 | 10/2005 | Chiou |
| 7,090,759 B1 | 8/2006 | Seul |
| 7,163,612 B2 | 1/2007 | Sterling et al. |
| 7,458,661 B2 | 12/2008 | Kim et al. |
| 7,612,355 B2 | 11/2009 | Wu |
| 7,956,339 B2 | 6/2011 | Ohta |
| 8,037,903 B2 | 10/2011 | Wang et al. |
| 2003/0008364 A1 | 1/2003 | Wang et al. |
| 2003/0224528 A1 | 12/2003 | Chiou et al. |
| 2004/0072278 A1 | 4/2004 | Chou et al. |
| 2004/0191789 A1 | 9/2004 | Manaresi et al. |
| 2004/0197905 A1 | 10/2004 | Hafeman |
| 2005/0112548 A1 | 5/2005 | Segawa et al. |
| 2005/0129581 A1 | 6/2005 | McBride et al. |
| 2005/0173313 A1 | 8/2005 | Tyvoll et al. |
| 2005/0175981 A1 | 8/2005 | Voldman et al. |
| 2006/0091015 A1 | 5/2006 | Lau |
| 2006/0154361 A1 | 7/2006 | Wikswo et al. |
| 2006/0186048 A1 | 8/2006 | Tan |
| 2007/0095669 A1 | 5/2007 | Lau |
| 2007/0183934 A1 | 8/2007 | Diercks et al. |
| 2008/0000635 A1 | 1/2008 | Paik |
| 2008/0223721 A1 | 9/2008 | Cohen |
| 2008/0302732 A1 | 12/2008 | Soh |

(Continued)

FOREIGN PATENT DOCUMENTS

| | | |
|---|---|---|
| EP | 1065378 A2 | 1/2001 |
| EP | 2685266 A4 | 1/2014 |

(Continued)

OTHER PUBLICATIONS

Banaeiyan, A.A. et al. Dec. 3, 2013. Hydrodynamic cell trapping for high throughput single-cell applications. Micromachines 4: 414-430. specif. pp. 416, 418, 426.*
Yamada, M. et al. 2005. Hydrodynamic filtration for on-chip particle concentration and classification utilizing microfluidics. Lab Chip 5: 1233-1239. specif. pp. 1233, 1234, 1235, 1236, 1238.*
Wlodkowic, D. et al. 2009. Microfluidic single-cell array cytometry for the analysis of tumor apoptosis. Analytical Chemistry 81: 5517-5523. specif. pp. 5517, 5518, 5519, 5521.*
Chung, K. et al. 2011. Imaging single-cell signaling dynamics with a deterministic high-density single-cell trap array. Analytical Chemistry 83: 7044-7052. specif. p. 7049.*
"Hua et al., Microfluidic Actuation Using Electrochemically Generated Bubbles, Anal Chem. 74:6392-96 (2002)."
Chiou et al., Massively parallel manipulation of single cells and microparticles using optical images, Nature 436:370-73 (2005).

(Continued)

*Primary Examiner* — Adam Weidner
*Assistant Examiner* — Sharon M. Papciak
(74) *Attorney, Agent, or Firm* — Kenneth E. Horton; Barnes & Thornburg LLP

(57) ABSTRACT

Some configurations of a microfluidic apparatus can comprise a fluidic circuit of interconnected fluidic structures into which a plurality of different media can be introduced or extracted. A variety of operations can be performed with the different media including isolating with a second medium one or more of the fluidic structures that is filled partially or fully with a first medium. Discrete volumes of a medium can be moved through the isolating second medium to deliver materials or micro-objects to or remove micro-objects or materials from a fluidic structure that is otherwise isolated by the second medium. Some configurations of a microfluidic apparatus can isolate microfluidic structures in a microfluidic apparatus using flow rates or blocking structures, and some configurations can manage bubbles in fluidic structures.

28 Claims, 28 Drawing Sheets

(56) References Cited

U.S. PATENT DOCUMENTS

| | | |
|---|---|---|
| 2009/0021728 A1 | 1/2009 | Heinz |
| 2009/0023608 A1 | 1/2009 | Hung et al. |
| 2009/0170186 A1 | 7/2009 | Wu |
| 2009/0220948 A1* | 9/2009 | Oviso ............... B01L 3/502707 435/6.19 |
| 2009/0266421 A1 | 10/2009 | Linder |
| 2009/0286300 A1 | 11/2009 | Vot et al. |
| 2010/0000620 A1 | 1/2010 | Fouillet |
| 2010/0003666 A1 | 1/2010 | Lee |
| 2010/0012568 A1 | 1/2010 | Angelescu |
| 2010/0012586 A1 | 1/2010 | Angelescu et al. |
| 2010/0101960 A1 | 4/2010 | Ohta |
| 2010/0252128 A1 | 10/2010 | Gong et al. |
| 2010/0273681 A1 | 10/2010 | Cerrina et al. |
| 2011/0053151 A1* | 3/2011 | Hansen .................. G06F 3/017 435/6.19 |
| 2011/0117634 A1 | 5/2011 | Halamish et al. |
| 2011/0143964 A1 | 6/2011 | Zhou et al. |
| 2011/0151479 A1 | 6/2011 | Stevens et al. |
| 2011/0262906 A1 | 10/2011 | Dimov et al. |
| 2012/0009671 A1 | 1/2012 | Hansen et al. |
| 2012/0015347 A1 | 1/2012 | Singhal et al. |
| 2012/0024708 A1 | 2/2012 | Chiou et al. |
| 2012/0118740 A1 | 5/2012 | Garcia et al. |
| 2012/0156675 A1 | 6/2012 | Lueerssen et al. |
| 2012/0325665 A1 | 12/2012 | Chiou et al. |
| 2013/0078163 A1 | 3/2013 | Chung et al. |
| 2013/0118905 A1 | 5/2013 | Morimoto et al. |
| 2013/0130232 A1 | 5/2013 | Weibel et al. |
| 2013/0146459 A1 | 6/2013 | Bazant et al. |
| 2013/0171628 A1 | 7/2013 | Di Carlo et al. |
| 2013/0190212 A1 | 7/2013 | Handique et al. |
| 2013/0204076 A1 | 8/2013 | Han et al. |
| 2013/0261021 A1 | 10/2013 | Bocchi et al. |
| 2014/0116881 A1 | 5/2014 | Chapman et al. |
| 2014/0124370 A1 | 5/2014 | Short et al. |
| 2015/0018226 A1 | 1/2015 | Hansen et al. |
| 2015/0151298 A1 | 6/2015 | Hobbs et al. |
| 2015/0151307 A1 | 6/2015 | Breinlinger et al. |
| 2015/0165436 A1 | 6/2015 | Chapman et al. |
| 2016/0184821 A1 | 6/2016 | Hobbs et al. |
| 2016/0199837 A1 | 7/2016 | Breinlinger et al. |
| 2016/0252495 A1 | 9/2016 | Ricicova et al. |
| 2016/0312165 A1 | 10/2016 | Lowe, Jr. et al. |
| 2017/0165667 A1 | 6/2017 | Beaumont et al. |
| 2018/0015473 A1 | 1/2018 | Bharadwaj et al. |
| 2018/0298318 A1 | 10/2018 | Kurz et al. |
| 2019/0240665 A1 | 8/2019 | Lionberger et al. |

FOREIGN PATENT DOCUMENTS

| | | |
|---|---|---|
| KR | 20100008222 A | 1/2010 |
| WO | 2002088702 A2 | 11/2002 |
| WO | 2004089810 A2 | 10/2004 |
| WO | 2005100541 A2 | 10/2005 |
| WO | 2007008609 A2 | 1/2007 |
| WO | 2007024701 A2 | 3/2007 |
| WO | 2008157257 A1 | 6/2008 |
| WO | 2008119066 A1 | 10/2008 |
| WO | 2009130694 A2 | 10/2009 |
| WO | 2010040851 A2 | 4/2010 |
| WO | 2010115167 A2 | 10/2010 |
| WO | 2010147078 A1 | 12/2010 |
| WO | 2010147942 A1 | 12/2010 |
| WO | 2011160430 A1 | 12/2011 |
| WO | 2012037030 A2 | 3/2012 |
| WO | 2012072823 A1 | 6/2012 |
| WO | 2012162779 A1 | 12/2012 |
| WO | 2013019491 A1 | 2/2013 |
| WO | 2014039514 A1 | 3/2014 |
| WO | 2014039514 A2 | 3/2014 |
| WO | 2019075476 A2 | 4/2019 |

OTHER PUBLICATIONS

Valley et al., Optoelectronic Tweezers as a Tool for Parallel Single-Cell Manipulation and Stimulation, IEEE Transactions on Biomedical Circuits and Systems 3(6):424-30 (2009).

Hur et al., High-Throughput Size Based Rare Cell Isolation Using Microscale Vortices, Intl Conf on Miniaturized Systems (2010).

WO201014078, University of Tokyo, Machine Translation, Dec. 23, 2010, 21 pages.

International Search Report and Written Opinion for PCT Application Serial No. PCT/US2015034594 (Aug. 30, 2015), 19 pages.

Chung et al., Imaging single-cell signaling dynamics with a deterministic high-density single-cell trap array, Anal. Chem.83(18):7044-7052 (2011).

The International Search Report and The Written Opinion of the International Searching Authority, PCT Application Serial No. US2015/034594, mailed Aug. 31, 2015 (19 pages).

Bose, Sayantan et al., Scalable microfluidics for single-cell RNA printing and sequencing, Genome Biology, 2015 16:120, CrossMark.

CHIOU_Dissertation_UC Berkeley "Massively Parallel Optical Manipulation of Single Cells, Micro- and Nano-particles on Optoelectronic Devices" 2005.

Chung et al., "Microwells support high-resolution time-lapse imaging and development of preimplanted mouse embryos", Biomicrofluidics 9:022407 (Apr. 28, 2015).

Hatch, A.C. et al., University of California-Irvine. Multilayer High-Density 3D Nanowell Arrays for Digital Biology. 15th International Conference on Miniaturized Systems for Chemistry and Life Sciences, Oct. 2-6, 2011, Seattle, Washington, USA.

Hsu, Hy et al., "Sorting of Differentiated Neurons Using Phototransistor-Based Optoelectronic Tweezers for Cell Replacement Therapy of Neurodegenerative Diseases", Transducers 2009, Denver, CO USA Jun. 2009, download dated Nov. 23, 2009 from IEEE Xplore, 4 pages.

Hung et al., Continuous Perfusion Microfluidic Cell Culture Array for High-Throughput Cell-Based Assays, Biotech and Bioengineering 89(1): 1-8 (2004). Dec. 3, 2004.

Iliescu et al., Continuous Field-Flow Separation of Particle Populations in a Dielectrophoretic Chip with Three Dimensional Electrodes, Applied Physics Letters 90:234104 (2007).

KIPO computer-generated English language translation of KR 20100008222A_Kyun.

Nevill et al., Integrated microfluidic cell culture and lysis on a chip, Lab on a Chip 7:1689-95 (2007).

Somaweera H. et al., Generation of a Chemical Gradient Across an Array of 256 Cell Cultures in a Single Chip. Analyst, Oct. 7, 2013, vol. 138, No. 19, pp. 5566-5571.

Xu, Guoling et al.,. Recent Trends in Dielectrophoresis, Informacije MIDEM, 2010, vol. 40, Issue No. 4, pp. 253-262.

Yi et al., "Microfluidics technology for manipulation and analysis of biological cells," Analytica Chimica Acta 560 (2006), pp. 1-23.

Yuan, Jinzhou and Sims, Peter, A., An Automated Microwell Platform for Large-Scale Single Cell RNA-Seq, Scientific Reports, 2016 6:33883, Nature.

* cited by examiner

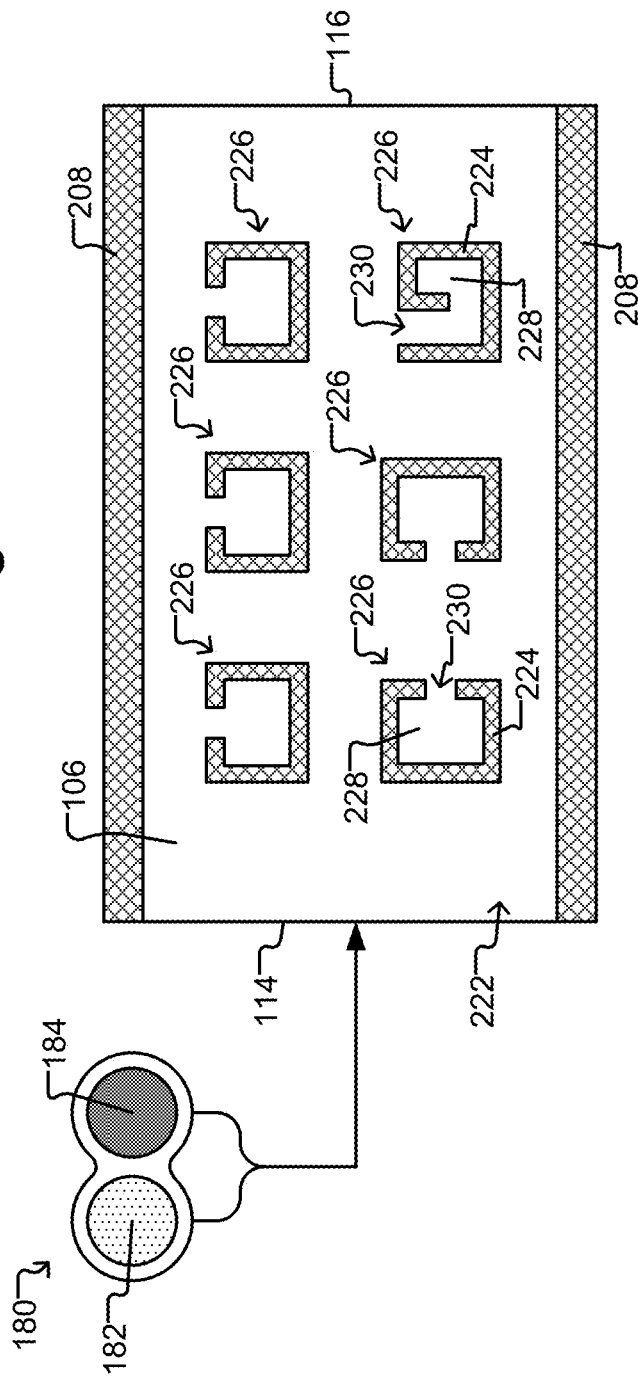

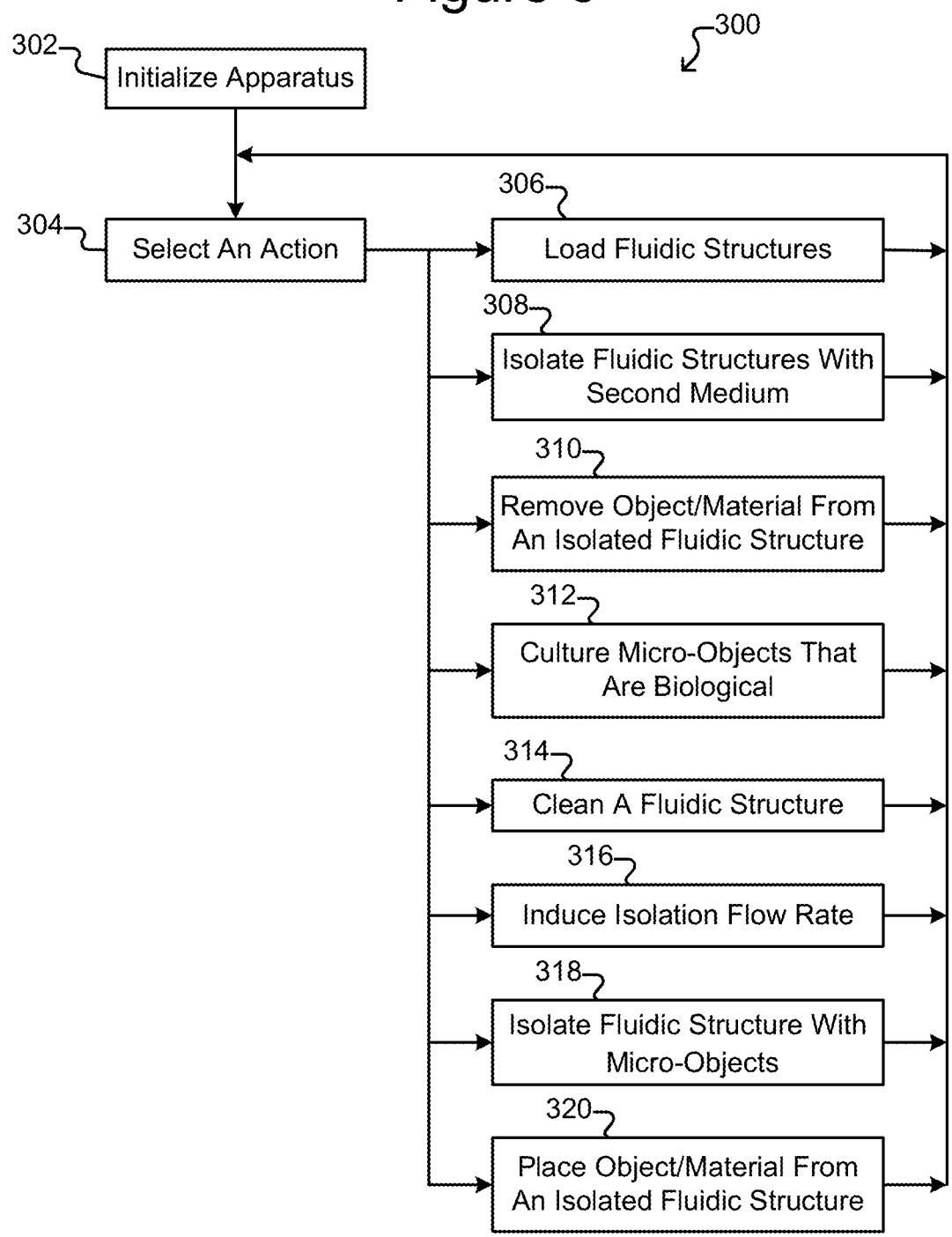

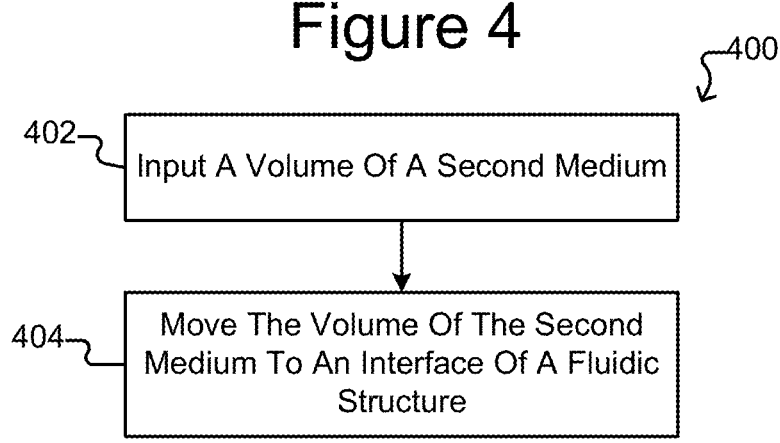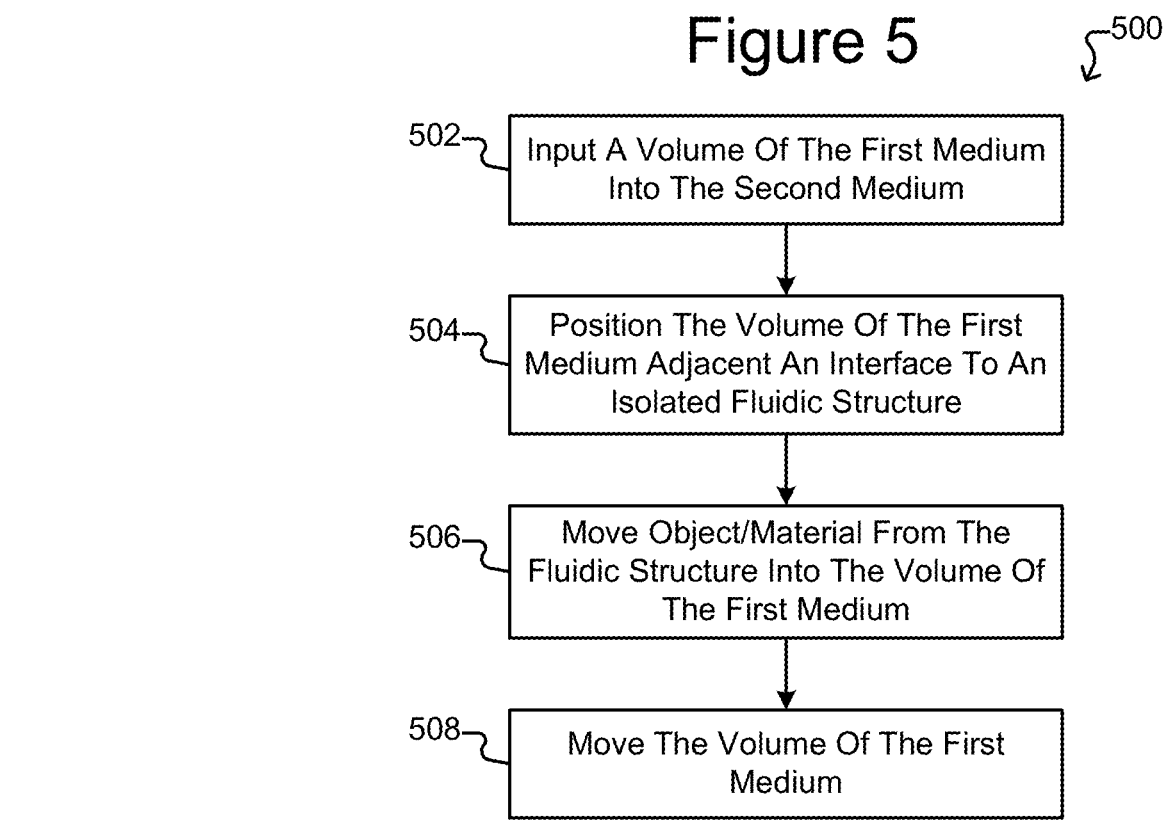

Figure 37
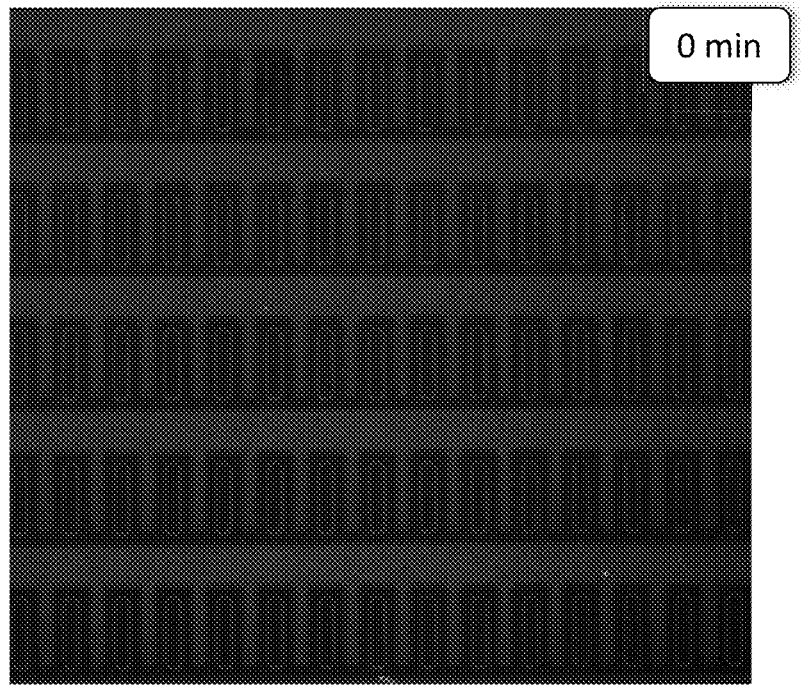
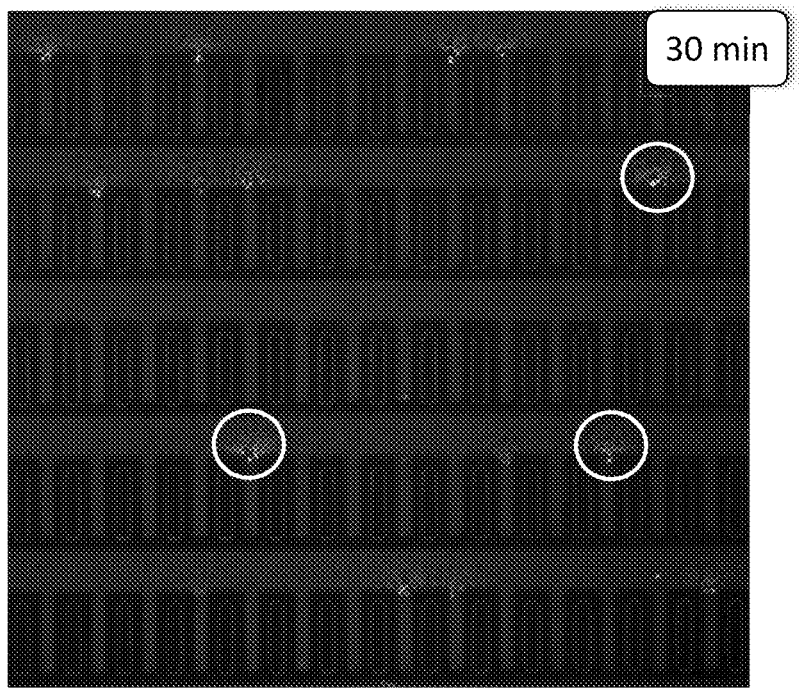

Figure 38
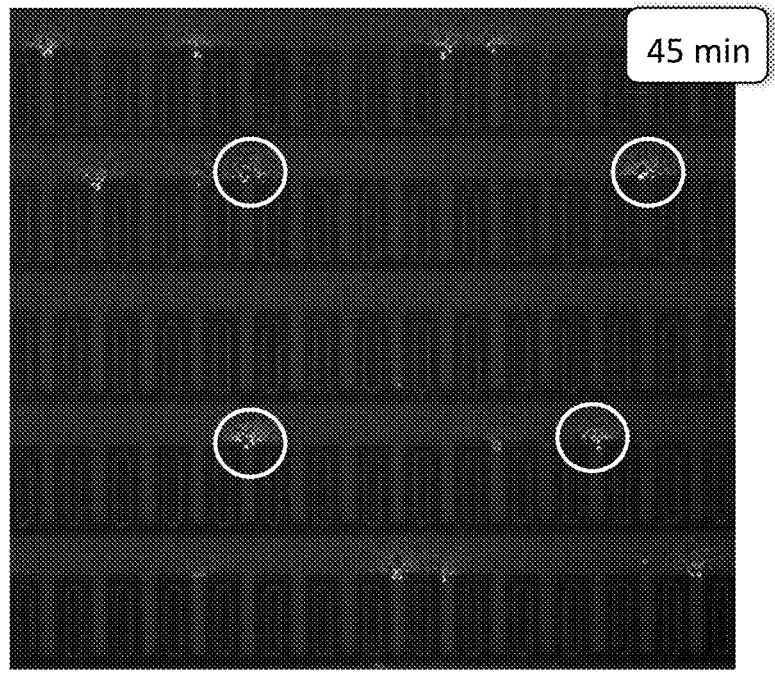
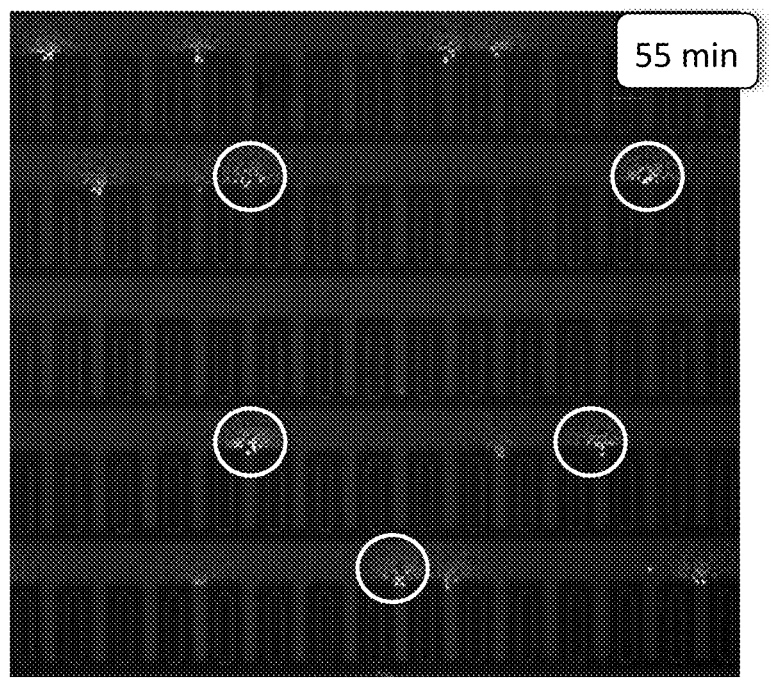

ISOLATING MICROFLUIDIC STRUCTURES AND TRAPPING BUBBLES

This application is a continuation of U.S. patent application Ser. No. 14/732,682 filed on Jun. 6, 2015, which is a non-provisional (and thus claims the benefit of the filing date of) U.S. Provisional Application No. 62/176,890, filed on Jun. 6, 2014, the disclosures of which are incorporated herein by reference in their entirety.

BACKGROUND

Micro-objects can be manipulated in microfluidic apparatuses. For example, inanimate micro-objects and/or biological micro-objects can be manipulated and/or analyzed in a microfluidic apparatus. Some embodiments of the present invention provide improvements in microfluidic apparatuses and in the operation of microfluidic apparatuses by, for example, isolating one or more fluidic structures and/or addressing the presence of bubbles in the microfluidic apparatus.

SUMMARY

In some embodiments, a process of operating a microfluidic apparatus can include introducing a first medium into a first fluidic structure and a second fluidic structure, which can be fluidically connected to the first fluidic structure. The process can also include isolating the second fluidic structure from the first fluidic structure.

In some embodiments, a microfluidic apparatus can comprise a fluidic channel, a first fluidic pen comprising a first opening connected to the channel, and a second fluidic pen comprising a second opening connected to the channel. The microfluidic apparatus can also include a flow discontinuity on an inner wall of the channel between the first opening and the second opening In some embodiments, a microfluidic apparatus can comprise a fluidic channel and a bubble trap. The fluidic channel can comprise a flow path for a fluidic medium. The bubble trap can comprise a first opening in the channel along the flow path. The first opening can be larger than a first cross-section of the fluidic path at an edge of the first opening, and the first cross-section can be substantially perpendicular to the flow path.

In some embodiments, a process of removing bubbles from a fluidic medium can include flowing a fluidic medium past a first opening in a fluidic channel. The first opening can connect the fluidic channel to a chamber, and the first opening can be larger than a first cross-section of the channel at an edge of the first opening. The process can also include pressure differentials on a bubble in the flowing medium at the first cross-section and at the first opening drawing the bubble from the channel through the first opening into the chamber.

In some embodiments, a process of providing substantially bubble-free fluidic medium to feed channels from a primary fluidic channel can include flowing a fluidic medium comprising bubbles in the primary fluidic channel. The process can also include first pressure differentials on the flowing fluidic medium at a first cross-section of the primary channel at a first edge of a first opening from the primary channel to a first of the feed channels drawing substantially bubble-free portions of the fluidic medium into the first feed channel. The first opening can be smaller than the first cross-section. The process can further include a second pressure differential on the flowing fluidic medium at a second cross-section of the primary channel at a second edge of a second opening (which can be smaller than the second cross-section) from the primary channel to a second of the feed channels drawing substantially bubble-free portions of the fluidic medium into the second feed channel.

In one aspect a microfluidic apparatus is provided including a flow region having a fluidic channel configured to direct fluid flow; at least two pens, each pen having a fluidic interface with the channel; where the fluidic channel is configured to fluidically isolate a first pen from a second pen by reducing diffusion of soluble components from the first pen into the second pen. In various embodiments, the fluidic interface of the first pen may be upstream from the fluidic interface of the second pen along the fluidic channel. The fluidic channel length between the first pen and the second pen may be at least 50% longer than a linear distance between the fluidic interface of the first pen and the fluidic interface of the second pen. In other embodiments, the length of the fluidic channel between the first pen and the second pen may be at least twice as long as a linear distance between the fluidic interface of the first pen and the fluidic interface of the second pen. In yet other embodiments, the length of the fluidic channel between the first pen and the second pen may be in a range of at least twice to about ten times as long as a linear distance between the fluidic interface of the first pen and the fluidic interface of the second pen. The fluidic channel of the microfluidic apparatus may be serpentine.

In various embodiments of the microfluidic apparatus, the fluidic channel may be interrupted by at least one interface with a minor fluidic channel having a non-parallel direction to the fluidic channel. The width of the minor fluidic channel may be about 10% of the width of the fluidic channel. In other embodiments, the width of the minor fluidic channel may be about 10% to about 50% of the width of the fluidic channel. In some embodiments, the fluidic channel may be serpentine, having a length between the first pen and the second pen in a range of at least twice to about five times as long as the linear distance between the fluidic interface of the first pen and the fluidic interface of the second pen, and may be interrupted by at least one interface with a minor fluidic channel having a non-parallel direction to the fluidic channel, where the width of the minor fluidic channel may be about 10% of the width of the fluidic channel or may be in a range of about 10% to about 50% of the width of the fluidic channel.

In various embodiments of the microfluidic apparatus, the fluidic channel may be interrupted by at least one interface with a branching fluidic channel having a generally similar direction of flow at the junction with the fluidic channel, but diverging from the direction of the fluidic channel after the intersection. In some embodiments, the branching channel is a minor fluidic channel. A width of a minor fluidic channel may be in a range from about 1% to about 10% of the width of the fluidic channel. In other embodiments, the width of the minor fluidic channel may be about 10% to about 50% of the width of the fluidic channel. In other embodiments, the branching channel may have a larger width than a minor branching fluidic channel and may have a width that is in a range from about 30% to about 90% of the width of the fluidic channel at the point of intersection.

In another aspect, a process of operating a microfluidic apparatus is provided, where the microfluidic apparatus includes a flow region having a fluidic channel and where the apparatus has at least two pens, where each of the pens has a fluidic interface with the fluidic channel, where the process includes the steps of: flowing a first fluidic medium along the fluidic channel; and fluidically isolating a first pen of the at least two pens from a second pen of the at least two pens by reducing diffusion of soluble components from the first pen into the second pen. The apparatus used in the process may be any apparatus as described herein. In various embodiments, diffusion of soluble components may be substantially reduced.

In various embodiments, flowing the first fluidic medium along the fluidic channel includes flowing the first fluidic medium past the fluidic interface of the first pen and, subsequently, past the fluidic interface of the second pen. In various embodiments, fluidically isolating the first pen from the second pen includes flowing the first fluidic medium along the fluidic channel where the fluidic channel may be configured to be at least 50% longer than a linear distance between the fluidic interface of the first pen and the fluidic interface of the second pen. In other embodiments, fluidically isolating the first pen from the second pen includes flowing the first fluidic medium along the fluidic channel where the fluidic channel may be configured to have a length in a range of at least twice to about ten times longer than a linear distance between the fluidic interface of the first pen and the fluidic interface of the second pen. Flowing the first fluidic medium along the fluidic channel may include flowing fluidic medium in a serpentine direction.

In various embodiments, the step of fluidically isolating may include interrupting the flowing of the first fluidic medium along the fluidic channel with a minor fluidic flow of a minor fluidic channel having a non-parallel direction to the flowing fluidic medium. The width of the minor fluidic channel may be about 10% of a width of the fluidic channel. Alternatively, the width of the minor fluidic channel is about 10% to about 50% of a width of the fluidic channel.

In some embodiments, the step of fluidically isolating the first pen from the second pen may include flowing the first fluidic medium along the serpentine fluidic channel wherein the serpentine fluidic channel may be configured to have a length in a range of at least twice to about five times longer than a linear distance between the fluidic interface of the first pen and the fluidic interface of the second pen.

In various embodiments, the step of fluidically isolating the first pen from the second pen further includes flowing a second fluidic medium along the fluidic channel; and displacing the first fluidic medium. The second fluidic medium may be substantially immiscible with the first fluidic medium.

In another aspect, a microfluidic apparatus is provided, including a fluidic channel including a flow path for a fluidic medium; and a bubble trap having a first opening in the channel along the flow path of the channel, where the first opening is larger than a first cross-section of the fluidic path at an edge of the first opening, and the cross-section is substantially perpendicular to the flow path. In various embodiments, the width of the first opening along the fluidic path may be greater than a width of the first cross-section of the channel. In some embodiments, the area of the first opening is greater than the area of the first cross-section of the channel.

In various embodiments of the bubble trap, the first opening in the channel along the flow path of the fluidic channel may be at least one and a half times larger than the first cross-section. The bubble trap may further include a chamber fluidically connected to the channel by the first opening. The chamber of the bubble trap may include a gas permeable sidewall. The bubble trap may further include an outgas channel disposed outside of the chamber and adjacent to the gas permeable sidewall. The bubble trap may further include a second opening to the channel along the flow path of the channel, where the second opening may be smaller than a second cross-section of the fluidic path at the edge of the second opening. The bubble trap may further include a barrier disposed between the first opening and the second opening and between the chamber and the channel. In some embodiments of the apparatus having a bubble trap, the first opening of the bubble trap may be substantially perpendicular to the first cross-section of the channel, and the second opening may be substantially perpendicular to the second cross-section of the channel. In other embodiments, the first opening of the bubble trap may be substantially perpendicular to the first cross-section of the channel. In various embodiments, more than one bubble trap may be present along the flow path of the channel. The one or more bubble traps may be located upstream of all pens in the microfluidic apparatus. The microfluidic apparatus having a bubble trap may further include a dielectrophoresis (DEP) device or electrowetting (OEW) device. The dielectrophoresis (DEP) device may be an optoelectronic tweezer (OET) device.

In yet another aspect, a process of removing bubbles from a fluidic medium in a microfluidic apparatus is provided, including the steps of: flowing a fluidic medium past a first opening in a fluidic channel of a microfluidic apparatus, the first opening connecting the fluidic channel to a chamber, where the first opening is larger than a first cross-section of the channel at an edge of the first opening; and drawing a bubble in the flowing medium at the first cross-section of the channel through the first opening into the chamber.

In various embodiments, the method of removing bubbles may further include filling the chamber with the fluidic medium prior to the step of flowing the fluidic medium. In some embodiments the step of drawing the bubble into the chamber displaces a volume of the fluidic medium from the chamber into the channel through a second opening connecting the channel to the chamber, and where the second opening may be smaller than a second cross-section of the channel at an edge of the second opening. In some embodiments, the first opening may be at least one and a half times larger than the first cross-section of the channel. In other embodiments, the first cross-section and the second cross-section of the channel may be substantially equal. In various embodiments of the method of removing bubbles, the first opening of the bubble trap may be substantially perpendicular to the first cross-section of the channel, and the second opening may be substantially perpendicular to the second cross-section of the channel.

In another aspect, a process of providing substantially bubble-free fluidic medium to one or more feed channels from a primary fluidic channel is provided, the process including the steps of: flowing a fluidic medium including bubbles in the primary fluidic channel past a first feed channel where an opening of the first feed channel at a first cross section of the primary fluidic channel has smaller dimensions than the first cross section, thereby retaining the bubbles in the fluidic medium in the primary fluidic channel; and drawing substantially bubble-free portions of the fluidic medium into the first feed channel. In various embodiments, the process may further include the steps of flowing medium containing bubbles at a second cross-section of the primary fluidic channel past a first edge of an opening of a second of the one or more feed channels, where the opening of the second feed channel has smaller dimensions than the second cross-section, thereby retaining the bubbles in the fluidic medium in the primary channel; and drawing substantially bubble-free portions of the fluidic medium into the second feed channel. In various embodiments, dimensions of the first cross-section and the second cross-section may be substantially the same. In some embodiments of the method, the opening of the first feed channel may be substantially perpendicular to the first cross-section of the primary channel, and the opening of the second feed channel may be substantially perpendicular to the second cross-section of the primary channel. In some embodiments of the method, the first cross-section of the primary channel may be at least one and half times larger than the opening of the first feed channel, and the second cross-section of the primary channel may be at least one and a half times larger than the opening of the second feed channel.

In another aspect a microfluidic apparatus is provided, including a fluidic channel; a pen connected by a fluidic interface to the channel; and a controller configured to isolate the channel from the pen when the pen contains a first medium, where a size of a cross-section of the channel is at least one and a quarter times greater than a size of the interface. In some embodiments, the fluidic interface may be an opening from the pen to the channel. In various embodiments, the controller may be configured to isolate the channel from the pen by flowing the first medium in the channel past the opening at a rate that is sufficiently fast to substantially eliminate diffusion through the opening. The method may substantially eliminate diffusion of soluble substances from the pen. In some embodiments, the apparatus may further include micro-objects sized to be placed in the opening. In other embodiments, the apparatus may include a plurality of micro-objects configured to be disposed at the opening of the channel or within the channel, where each micro-object may have a diameter smaller than a cross-sectional dimension of the channel. The micro-object may be configured to bind a particular biological material. In various embodiments of the apparatus, the controller may be configured to isolate the channel from the pen by moving a volume of a second medium to block the interface. In various embodiments, the controller may be configured to replace with the volume of the second medium a corresponding volume of the first medium in the channel. In some embodiments, the interface may be an only fluidic connection between the channel and the pen.

In yet another aspect, a microfluidic apparatus is provided, including a fluidic channel; a first fluidic pen having a first opening connected to the channel; a second fluidic pen having a second opening connected to the channel; and a flow discontinuity on an inner wall of the channel between the first opening and the second opening. In various embodiments, the flow discontinuity may include a protrusion into the channel between the first opening and the second opening. In some embodiments, the inner wall of the channel may be hydrophilic between the first opening and the second opening except for at least one hydrophobic area, wherein the at least one hydrophobic area may be configured to provide the flow discontinuity. In other embodiments, the flow discontinuity includes means for separating a first portion of a medium in the fluidic channel and a second portion of the medium in the first pen.

In another aspect, a process of operating a microfluidic apparatus is provided, the process including the steps of introducing a first volume of a first medium into a first fluidic structure and a second fluidic structure, where the second fluidic structure is fluidically connected to the first fluidic structure; and isolating the second fluidic structure from the first fluidic structure. In various embodiments, the first fluidic structure may be a fluidic channel, and the second fluidic structure may be a pen comprising an opening connected to the In various embodiments, the isolating step may include disposing a volume of a second medium at a first fluidic interface between the first fluidic structure and the second fluidic structure, the first medium remaining in the second fluidic structure.

The process of operating a microfluidic apparatus may further include loading a biological micro-object into the second fluidic structure. In various embodiments, the process may further include the step of culturing the biological micro-object in the second fluidic structure. In some embodiments, the culturing may be performed while the second fluidic structure is isolated from the first fluidic structure by the volume of the second medium. In some embodiments, the step of culturing may be performed after the isolating step. In various embodiments, the process may further include loading a biological micro-object into the second fluidic structure before disposing the volume of the second medium at the first fluidic interface. In some embodiments, loading the biological micro-object may include generating dielectrophoretic (DEP) forces that move the biological micro-object into the second fluidic structure. In some other embodiments, loading the biological micro-object may include generating electro-wetting (EW) forces that move the biological micro-object into the fluidic structure. In various embodiments of the process, the introducing step may further include introducing the first volume of the first medium into a third fluidic structure, wherein the third fluidic structure is fluidically connected to the first fluidic structure, and the isolating may further include isolating the third fluidic structure from the first fluidic structure by disposing the volume of the second medium at a second fluidic interface between the first fluidic structure and the third fluidic structure. In some embodiments, the isolating step may further include disposing the volume of the second medium at both the second fluidic interface and the first fluidic interface, thereby isolating the second fluidic structure from the third fluidic structure.

In various embodiments, the process of operating a microfluidic apparatus may further include moving a second volume of the first medium through the volume of the second medium to the first interface; and displacing the volume of the second medium from the first interface. In some embodiments, the displacing step may displace a portion of the volume of the second medium from the first interface.

In various embodiments of the process of operating a microfluidic apparatus, the process may further include moving the biological micro-object from the second fluidic structure into the second volume of the first medium at the first interface. In some embodiments, moving the biological micro-object object may include generating dielectrophoretic (DEP) forces or electrowetting (EW) forces that move the biological micro-object. In various embodiments, the process may further include moving the second volume of the first medium containing the biological micro-object away from the first interface. In various embodiments, the process may further include allowing biological material from the second fluidic structure to diffuse through the first interface into the second volume of the first medium. In various other embodiments, the process may further include moving the second volume of the first medium containing the biological material away from the first interface. In yet other embodiments, the process may further include moving a second micro-object in the second volume of the first medium through the first interface into the second fluidic structure. In other embodiments, the process may further include allowing material in the second volume of the first medium to diffuse through the first interface into the second fluidic structure. In some embodiments, the second medium may be immiscible with respect to the first medium. In some embodiments, the first medium may be an aqueous liquid. In yet other embodiments, the second medium may be a gas or a non-aqueous liquid. In some embodiments, the second medium may include an oil.

In various embodiments, the process may further include cleaning the first fluidic structure by passing a volume of a second medium through the first fluidic structure. In other embodiments of the process, isolating may include flowing the first medium in the channel at a rate that is sufficiently fast to substantially eliminate diffusion through the opening.

In various embodiments, the process of operating a microfluidic apparatus may further include the steps of loading a first micro-object into the second fluidic structure; and producing a material from the first micro-object.

In various embodiments of the process of operating a microfluidic apparatus, the step of isolating may include disposing one or more second micro-objects in the opening. In some embodiments, the disposing step may include disposing a sufficient number of the second micro-objects in the opening to substantially physically block the opening. In some embodiments, the one or more second micro-objects may be configured to bind the material produced by the first micro-object.

In various embodiments of the process, the isolating step may include substantially filling the channel with second micro-objects. In some embodiments, the second micro-objects may be configured to bind the material produced by the first micro-objects.

In various embodiments of the process, loading the first micro-object may include generating dielectrophoretic (DEP) forces or electrowetting (EW) forces that move the biological micro-object. In various embodiments of the process, the step of disposing the one or more second micro-objects may include generating dielectrophoretic (DEP) forces or electrowetting (EW) forces that move the one or more second micro-objects-.

In yet another aspect a process of operating a microfluidic apparatus is provided, the process including the steps of disposing a first biological micro-object in a first microfluidic pen of the microfluidic apparatus; disposing a second biological micro-object in a second microfluidic pen of the microfluidic apparatus, where the second pen is fluidically connected to the first pen; isolating the first pen from the second pen; and culturing the first biological micro-object in the first pen. The process may further include the step of analyzing the first biological micro-object.

In some embodiments, the process may further include culturing the second biological micro-object in the second pen after the first pen is isolated from the second pen. In various embodiments, the process may further include the step of, after the culturing the second analyte, analyzing the second biological micro-object.

In various embodiments, the step of analyzing the first biological micro-object or analyzing the second biological micro-object may include analyzing one or more biological materials produced by the first or second biological micro-object.

In various embodiments, the step of disposing the first biological micro-object or the second biological micro-object may include generating dielectrophoretic (DEP) forces or electrowetting (EW) forces to move the first biological micro-object or second biological micro-object.

In various embodiments, the process may further include delivering one or more assay reagents to the first pen or the second pen using dielectrophoresis (DEP) devices or electrowetting (EW) devices.

BRIEF DESCRIPTION OF THE DRAWINGS

FIG. 2 is a top view without the cover of another example of a configuration of the microfluidic apparatus of FIGS. 1A and 1B according to some embodiments of the invention.

FIG. 3 is an example of a process that can be performed on the apparatuses of FIGS. 1A, 1B, and 2 according to some embodiments of the invention.

FIG. 4 shows an example of a process for isolating a fluidic structure in a microfluidic apparatus according to some embodiments of the invention.

FIG. 5 is an example of a process for removing a micro-object from an isolated fluidic structure in a microfluidic apparatus according to some embodiments of the invention.

FIG. 37 is a photographic representation of another embodiment of isolating microfluidic structures of FIG. 1 according to some embodiments of the invention.

FIG. 38 is a photographic representation of another embodiment of isolating microfluidic structures of FIG. 1 according to some embodiments of the invention.

DETAILED DESCRIPTION OF EXEMPLARY EMBODIMENTS

Figure 1A:
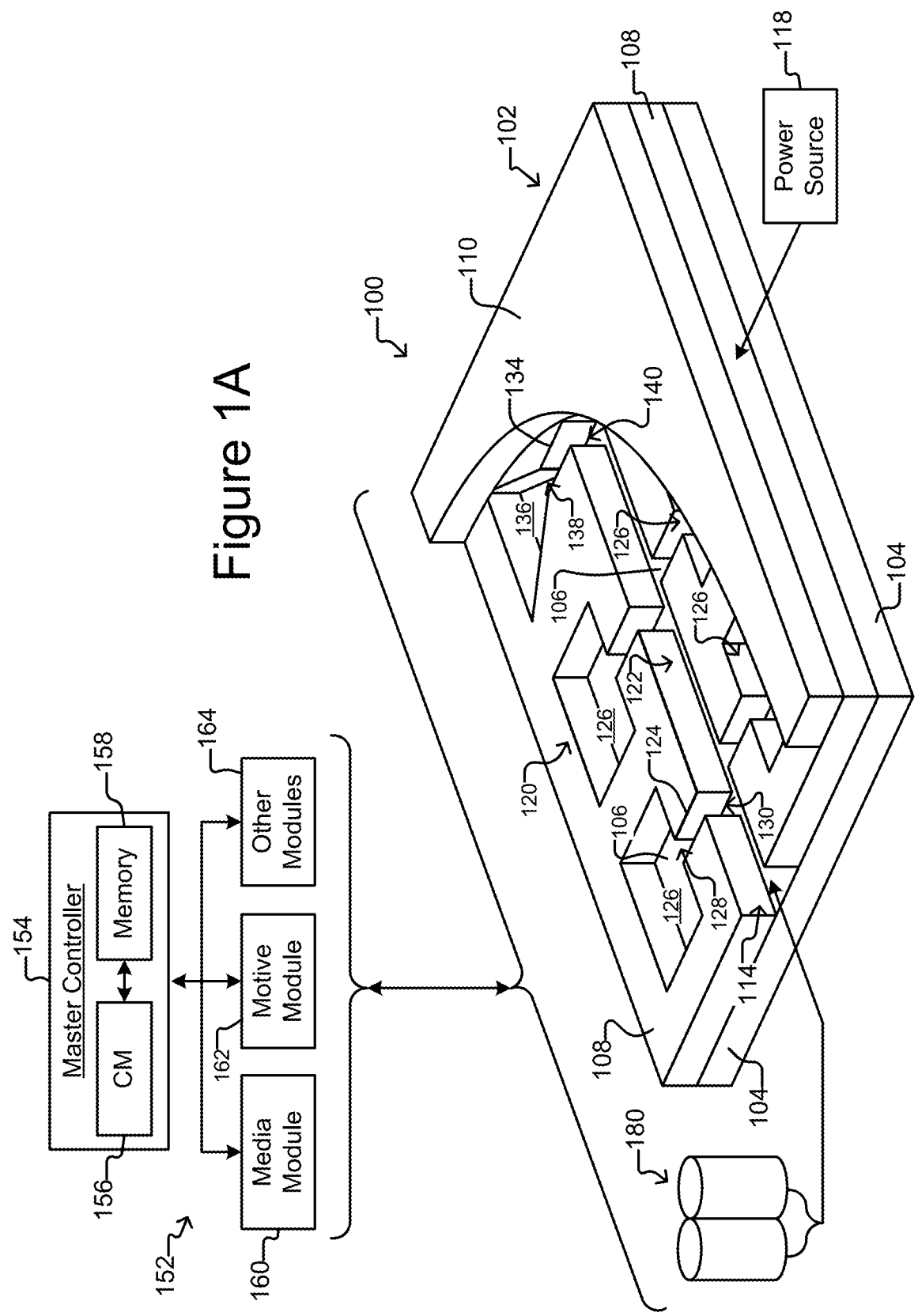
FIG. 1A illustrates a perspective view of an example of a microfluidic apparatus with a partial cut-out view through the cover and examples of control equipment according to some embodiments of the invention.

This specification describes exemplary embodiments and applications of the invention. The invention, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," or "coupled to" are used herein, one element (e.g., a material, a layer, a substrate, etc.) can be "on," "attached to," or "coupled to" another element regardless of whether the one element is directly on, attached to, or coupled to the other element or there are one or more intervening elements between the one element and the other element. Also, directions (e.g., above, below, top, bottom, side, up, down, under, over, upper, lower, horizontal, vertical, ceiling, floor, base, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent. The term "ones" means more than one.

As used herein, the term "micro-object" can encompass one or more of the following: inanimate micro-objects such as nanoparticles, microparticles, microbeads (e.g., polystyrene beads, glass beads, Luminex™ beads, or the like, any of which may be solid core or porous), magnetic or paramagnetic beads (e.g. solid phase reversible immobilization (SPRI) beads), microrods, microwires, quantum dots, and the like; biological micro-objects such as cells (e.g., embryos, oocytes, sperms, cells dissociated from a tissue, blood cells, hybridomas, cultured cells, cells from a cell line, cancer cells, infected cells, transfected and/or transformed cells, reporter cells, and the like), liposomes (e.g., synthetic or derived from membrane preparations), lipid nanorafts, proteins, genetic material (e.g., DNA), transfection vectors, nanoparticles (e.g. organelles), and the like; or a combination of inanimate micro-objects and biological micro-objects (e.g., microbeads attached to cells, liposome-coated microbeads, liposome-coated magnetic beads, or the like). Lipid nanorafts have been described, e.g., in Ritchie et al. (2009) "Reconstitution of Membrane Proteins in Phospholipid Bilayer Nanodiscs," Methods Enzymol., 464:211-231.

As used herein, "air" refers to the composition of gases predominating in the atmosphere of the earth. The four most plentiful gases are nitrogen (typically present at a concentration of about 78% by volume, e.g., in a range from about 70-80%), oxygen (typically present at about 20.95% by volume at sea level, e.g. in a range from about 10% to about 25%), argon (typically present at about 1.0% by volume, e.g. in a range from about 0.1% to about 3%), and carbon dioxide (typically present at about 0.04%, e.g., in a range from about 0.01% to about 0.07%). Air may have other trace gases such as methane, nitrous oxide or ozone, trace pollutants and organic materials such as pollen, diesel particulates and the like. Air may include water vapor (typically present at about 0.25%, or may be present in a range from about 10 ppm to about 5% by volume). Air may be provided for use in culturing experiments as a filtered, controlled composition and may be conditioned as described herein.

As used herein, the term "cell" refers to a biological cell, which can be a plant cell, an animal cell (e.g., a mammalian cell), a bacterial cell, a fungal cell, or the like. A mammalian cell can be, for example, from a human, a mouse, a rat, a horse, a goat, a sheep, a cow, a primate, or the like.

As used herein, "fluidic circuit" means one or more fluidic structures (e.g., chambers, channels, holding pens, reservoirs, or the like), which can be interconnected. A "fluidic circuit frame" means one or more walls that define all or part of a fluidic circuit. The term "fluid" includes within its meaning gases and liquids.

As used herein, the phrase "fluidically connected" or "in fluid connection with" and the like means that, when different regions of a microfluidic structure of a microfluidic apparatus, including a microfluidic circuit, are substantially filled with fluid, such as fluidic media, the fluid in each of the regions are in physical contact. This does not mean that the fluids (or fluidic media) in the different regions are necessarily identical in composition nor that the fluidic media are necessarily miscible in each other. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the microfluidic structure.

As referred to herein, "gas permeable" means that the material or structure is permeable to at least one of oxygen, carbon dioxide, or nitrogen. In some embodiments, the gas permeable material or structure is permeable to more than one of oxygen, carbon dioxide and nitrogen and may further be permeable to all three of these gases.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

As used herein, "microfluidic channel", "fluidic channel" or "flow channel" refers to a flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is in the range of from about 10,000 microns to about 500,000 microns, including any range therebetween. In some embodiments, the horizontal dimension is in the range of from about 30 microns to about 1000 microns, about 50 to about 900 microns, about 100 microns to about 1000 microns, about 100 microns to about 900 microns, about 100 microns to about 800 microns, about 100 microns to about 700 microns, about 100 to about 600 microns, about 100 microns to about 500 microns, about 100 microns to about 400 microns, about 100 microns to about 300 microns, or about 100 to about 200 microns. In some embodiments, the width of a flow channel may be about 200 microns. The vertical dimension of a flow channel is in the range of from about 25 microns to about 100 microns, e.g., from about 40 to about 50 microns. It is noted that a flow channel may have a variety of different\ spatial configurations in a microfluidic device, and thus is not restricted to a perfectly linear element. For example, a flow channel may be, or include one or more sections having, the following configurations: straight, curve, bend, spiral, incline, decline, serpentine (e.g., meandering, coiling, or having a flow path that is constrained to double back on itself), fork (e.g., multiple different flow paths), and any combination thereof. In addition, a flow channel may have different cross sectional areas along its path, widening and constricting to provide a desired fluid flow therein.

Some embodiments of the present invention include a microfluidic apparatus comprising a fluidic circuit of interconnected fluidic structures into which a plurality of different media can be introduced and/or extracted. A variety of operations can be performed with the different media including isolating with a second medium one or more of the fluidic structures that is filled partially or fully with a first medium. As another example, discrete volumes (e.g., droplets) of a medium can be moved through the isolating second medium to deliver materials or micro-objects to or remove micro-objects or materials from a fluidic structure that is otherwise isolated by the second medium. Some embodiments of the invention comprise isolating microfluidic structures in a microfluidic apparatus using flow rates or blocking structures, and some embodiments of the invention comprise managing bubbles in a microfluidic apparatus.

Figure 1B:
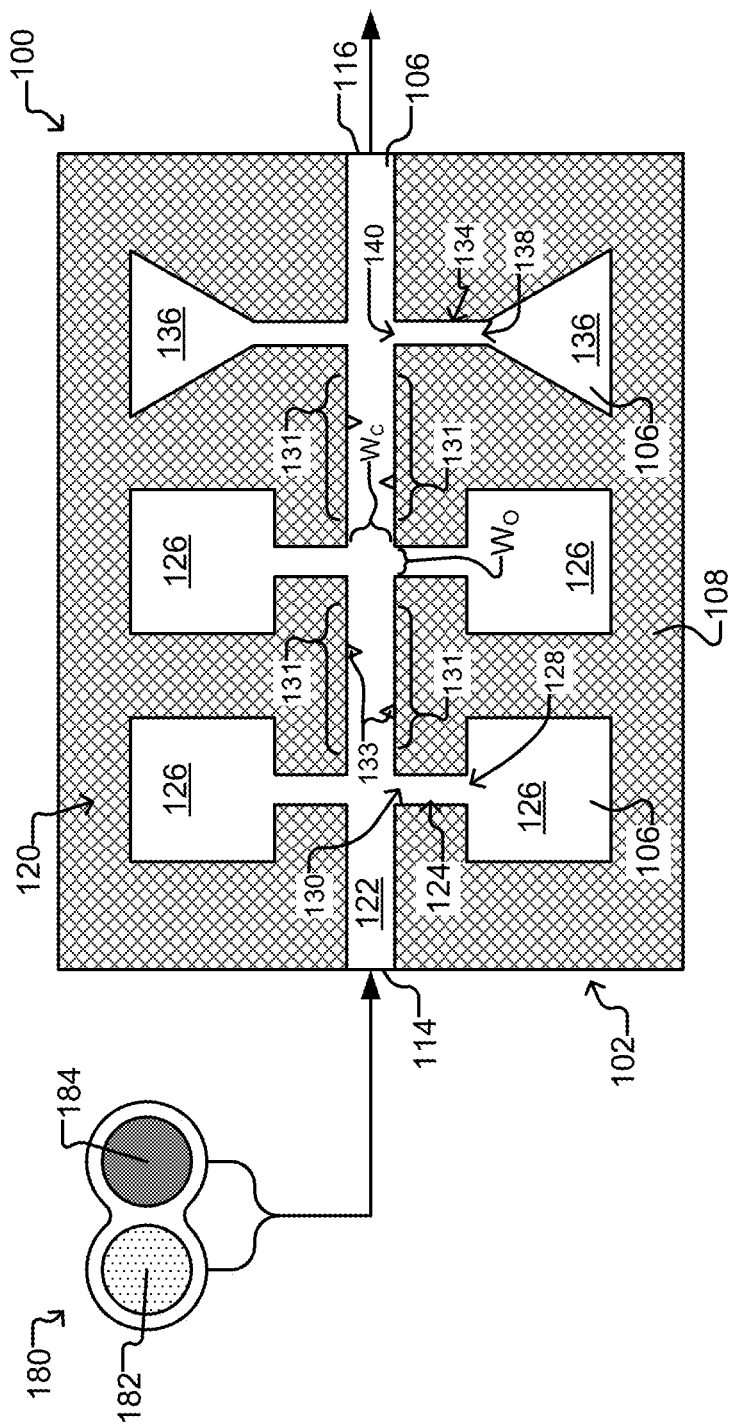
FIG. 1B is a top view of the media source and the microfluidic apparatus of FIG. 1A with its cover removed.

FIGS. 1A and 1B illustrate an example of a microfluidic apparatus 100. In FIG. 1A, the apparatus 100 is depicted in a perspective view with a cut out in the cover 110, and FIG. 1B shows a top view of the apparatus 100 without the cover 110.

Although the apparatus 100 can be physically structured in different ways, in the example shown in FIGS. 1A and 1B, the enclosure 102 is depicted as comprising a structure 104 (e.g., a base), a fluidic circuit frame 108, and a cover 110. As shown, the fluidic circuit frame 108 can be disposed on an inner surface 106 of the structure 104, and the cover 110 can be disposed over the fluidic circuit frame 108. With the structure 104 and the cover 110, the fluidic circuit frame 108 can define a fluidic circuit 120, which can comprise one or more fluidic structures (e.g., chambers, channels, pens, reservoirs, and the like), which can be interconnected. The structure 104 can be at the bottom and the cover 110 at the top of the apparatus 100 as illustrated in FIGS. 1A and 1B. Alternatively, the structure 104 and cover 110 can be in other orientations. For example, the structure 104 can be at the top and the cover 110 at the bottom of the apparatus 100. Regardless, there can be one or more inlets 114 into and one or more outlets 116 out of the enclosure 102. The inlets 114 and outlets 116 can be flow regulated or non-flow regulated and can be, for example, valves, passages, or the like.

In the example of FIG. 1A, the fluidic circuit 120 is illustrated as comprising four fluidic structures (any one of which can be an example of a first, second, third, or fourth fluidic structure): a fluidic channel 122 to which three isolation pens 126, 136 are fluidically connected. In FIG. 1B, a total of seven fluidic structures are shown including channel 122, four pens 126, and 2 pens 136. There can be more or fewer fluidic structures in any fluidic circuit, and those fluidic structures can include a channel 122 and pens 126, 136 as shown and/or any other types, numbers, and interconnections of fluidic structures. FIGS. 2, and 26-31 illustrate an example of an alternative configuration.

FIG. 2 shows a top view without the cover 110 of another example of a microfluidic apparatus 200, which can be the same as the microfluidic apparatus 100 of FIGS. 1A and 1B except that the apparatus 200 comprises a fluidic circuit frame 208 rather than the fluidic circuit frame 108 of FIGS. 1A and 1B. As shown, the fluidic circuit frame 208 can comprise walls 208 that, with the surface 106 of the structure 104 and the cover 110 (not shown in FIG. 2), can define a relatively wide channel 222 and pens 226 disposed inside the channel 222. Each pen 226 can, for example, comprise walls 224, an interior space 228, and an opening 230 from the channel 222 into the interior space 228. The walls 224 can be part of the fluidic circuit frame 208, which can otherwise be like (e.g., comprised of the same materials as) the fluidic circuit frame 108. Although six pens 226 with difference shapes and orientations are shown in FIG. 2, there can be fewer or more than six pens 226 in a channel 222, and the pens 226 can take any of many possible shapes or orientations. All discussions and references herein to the channel 122 or pens 126, 136 (or the openings 128 or 130) of FIGS. 1A and 1B are equally applicable to the channel 222 and pens 226 (or openings 230) of FIG. 2. Similarly, references herein to the apparatus 100 are applicable to the apparatus 200.

Referring again to FIGS. 1A and 1B and the apparatus 100, the channel 122 can comprise a flow path for liquid and/or gas media. In the example shown in FIGS. 1A and 1B, the channel 122 is illustrated as connected to an inlet 114 into and an outlet 116 out of the enclosure 102. Alternatively, the channel 122 can be connected to, and thus provide a flow path between, other microfluidic structures (not shown) of the fluidic circuit 120. Regardless, the pens 126, 136 can be configured to hold liquid and/or gas media and can be fluidically connected to the channel 122. For example, a fluidic connector 124, 134 can fluidically connect a pen opening 128, 138 to a channel opening 130, 140. In some embodiments, however, there are not fluidic connectors 124, 134, and a pen opening 128, 138 and a corresponding channel opening 130, 140 are the same. A connector 124, 134, a pen opening 128, 138, and/or a channel opening 130, 140 are all examples of a fluidic interface between a pen 126, 136 and the channel 122.

The pens 126, 136 and their channel openings 130, 140, connectors 124, 134, and pen openings 128, 138 can be any of a variety of possible shapes and sizes (e.g., like pens 226 in FIG. 2). FIGS. 1A and 1B illustrate examples of generally square or rectangular shaped pens 126 and generally triangular shaped pens 136. Other examples of shapes include circular, oval, polygon, hybrid shapes, complex shapes, or the like. Moreover, corners of the pens 126, 136, channel openings 130, 140, connectors 124, 134, and pen openings 128, 138 can be sharp (as shown) or rounded.

As shown in FIG. 1B, a size $W_O$ (e.g., cross-sectional width, diameter, area, or the like) of a channel opening 130, 140 can be less than the size $W_C$ (e.g., cross-sectional width, diameter, area, or the like) of the channel 122 (e.g., in the immediate vicinity of a channel opening 130, 140). As shown in FIG. 1B, the cross-section of the channel opening 130, 140 corresponding to the size $W_O$ of the channel opening 130, 140 can be substantially perpendicular to the cross-section of the channel corresponding to the size $W_C$ the channel 122. In some embodiments, the size $W_C$ of the channel 122 can be one and a quarter, one and a half, two, three, or more times the size $W_O$ of a channel opening 130, 140. This can reduce a rate of diffusion (or diffusion flux) through the opening 130, 140 for materials diffusing from a selected pen 126, 136 into channel 122 and subsequently re-entering a downstream or adjacent pen 126, 136. The rate of diffusion of a molecule (e.g., an analyte of interest, such as an antibody) is dependent on a number of factors, including (without limitation) temperature, viscosity of the medium, and the coefficient of diffusion $D_0$ of the molecule. For example, the $D_0$ for an IgG antibody in aqueous solution at about 20° C. is about $4.4 \times 10^{-7}$ cm$^2$/sec, while the kinematic viscosity of cell culture medium is about $9 \times 10^{-4}$ m$^2$/sec. Thus, an antibody in cell culture medium at about 20° C. can have a rate of diffusion of about 0.5 microns/sec. Accordingly, in some embodiments, a time period for diffusion from a biological micro-object located pen 126, 136 into the channel 122 can be about 10 minutes or less (e.g., about 9, 8, 7, 6, 5 minutes, or less). The time period for diffusion can be manipulated by changing parameters that influence the rate of diffusion. For example, the temperature of the media can be increased (e.g., to a physiological temperature such as about 37° C.) or decreased (e.g., to about 15° C., 10° C., or 4° C.) thereby increasing or decreasing the rate of diffusion, respectively. Alternatively, or in addition, the concentrations of solutes in the medium can be increased or decreased as discussed herein to isolate a selected pen from solutes from other upstream pens.

In addition, as discussed below with respect to FIG. 21, the smaller size $W_O$ of the channel openings 130, 140 (as compared to the size $W_C$ of the channel 122) can reduce or substantially eliminate bubbles (e.g., of air, oil, or any immiscible fluid) in the channel 122 from entering the pens 126, 136.

The inner walls of the fluidic circuit 120 can all be hydrophobic or hydrophilic. In some embodiments, the term hydrophilic when used with reference to modified inner walls or other features of the microfluidic circuit, may include features that are less hydrophobic than the walls as fabricated (which are hydrophobic). For example, all of the walls of the channel 122, connectors 124, 134, and pens 126, 136 can be hydrophobic or all can be hydrophilic. Alternatively, one or more portions of the inner walls of the fluidic circuit 120 can be hydrophobic and other portions of the inner walls can be hydrophilic. For example, the walls (e.g., comprising parts of the structure 104, fluidic circuit structure 108, and/or cover 110) of the channel 122 can be hydrophobic and the walls of the connectors 124, 134 and/or the pens 126, 136 can be hydrophilic. As yet another example, one or more portions (e.g., patches or areas 131) of the inner walls of the channel 122 between adjacent channel openings 130, 140 can be hydrophobic, and other portions of the walls of the channel 122 can be hydrophilic and/or the walls of the connectors 124, 134 and/or the pens 126, 136 can be hydrophilic. Alternatively or in addition, the channel 122 can comprise protrusions 133 extending from a wall of the channel 122 into the channel 122. The protrusions 133, which can be pointed or blunt, can be disposed between channel openings 130, 140 of adjacent pens 126, 136. As will be discussed, one or more of the foregoing features can aid in separating the medium in the channel 122 and the medium in the pens 126, 136, allowing the medium in the channel 122 to be removed without also substantially removing the medium from the pens 126, 136. One or more of these features can permit the medium in a selected individual pen 126 to remain substantially isolated from components present in the medium in other adjacent pens 126, 136 which may diffuse from adjacent pens 126, 136 into the channel 122. The protrusions 133 can also effectively increase a distance between adjacent pen openings 130, 140, which can decrease the likelihood of unwanted materials (not shown) in the channel 122 diffusing into a pen 126, 136. The foregoing can also be examples of flow discontinuities in the channel 122 between openings 130, 140 to adjacent pens 126, 136.

The structure 104 can comprise, for example, a substrate or a plurality of interconnected substrates. For example, the structure 104 can comprise one or more semiconductor substrates, printed circuit boards, or the like. The fluidic circuit frame 108 can comprise a flexible material (e.g. rubber, plastic, an elastomer, silicone, photo patternable silicone (PPS), polydimethylsiloxane ("PDMS"), or the like), which can be gas permeable. The cover 110 can be an integral part of the fluidic circuit frame 108, or the cover 110 can be a structurally distinct element (as illustrated in FIGS. 1A and 1B). The cover 110 can comprise the same or different materials than the fluidic circuit frame 108. In some embodiments, the cover 110 and/or the structure 104 can be transparent to light.

Surface properties of inner walls of the fluidic circuit 120 can be set in any of many different ways. For example, all inner walls of the fluidic circuit 120 can be rendered hydrophilic or hydrophobic and selected portions of the inner walls can then be rendered the other of hydrophobic or hydrophilic. Non-limiting examples of techniques for rendering all or part of a surface of an inner wall of a microfluidic circuit hydrophobic or hydrophilic include applying a dynamic coating, plasma-assisted surface modification; covalent modification, biotin/streptavidin, nonspecific binding treatments; nanoparticle-based treatments; or the like.

In embodiments where the inner walls of the fluidic circuit 120 are hydrophobic after initial fabrication, such as but not limited to silicone or PDMS, a dynamic coating (e.g., a liquid based coating) may be used to render all or a portion of the inner walls hydrophilic. One non-limiting exemplary class of liquid based coatings include alkylene ether containing polymers. These polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a conditioned surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da. Other surfactants such as sodium dodecyl sulfate (SDS), Brij® (polyoxyethylene glycol alkyl ethers), phosphatidic acid, Triton™ X-100 (polyethylene glycol tert-octylphenyl ether), or didodecyldimethylammonium bromide may be used in a dynamic coating.

Another type of treatment, plasma-assisted surface modification, may also be used to introduce hydrophilic character to hydrophobic inner walls. Hydroxyl functionalities may be introduced or alternatively, plasma modification can include graft of hydrophilic polymers on to the wall surface, which can include acrylic or lactic acid monomers. One specific example of covalent modification after surface plasma treatment includes introduction of biotin functionalized monolayers which can further immobilize avidin. Ultraviolet treatment may also be used to introduce hydroxyl functionalities onto the wall surface, which can be further modified upon chemical modification with hydrophilic reagents. Chemical vapor deposition with, for example, poly(p-xylene) species can provide precise and selective surface modification which may also be further modified by reaction with chemical reagents providing a hydrophilic surface at the selected location. Layer by layer (LBL) deposition is another alternative which can be used to form adherent layers of alternating charge polyion species, and can even introduce protein or polysaccharide moieties, thus offering avenues to biocompatible surface modification. Non-specific binding treatments with proteins can provide biocompatible and hydrophilic surface modifications. Nanoparticle modification with, for example, sputtered gold nanoparticles can provide hydrophilic surfaces at selected locations. The various types of modifications can be used in any kind of combination to arrive at hydrophilic modified locations in the fluidic circuit.

An electrical power source 118 is shown in FIG. 1A, and a media source 180 is shown in FIGS. 1A and 1B. The power source 118 can provide electric power to the apparatus 100 and biasing voltages or currents as needed. The electrical power source 118 can, for example, comprise one or more alternating current (AC) or direct current (DC) voltage or current sources. The media source 180 (e.g., a container, reservoir, or the like) can comprise multiple sections or containers each for holding a different medium. In the example shown in FIGS. 1A and 1B, the media source 180 comprises two sections for holding a first medium 182 and a second medium 184 (see FIG. 1B), but the media source 180 can comprise more than two sections and can thus hold more than two different media.

The first medium 182 can be a different medium than the second medium 184. For example, the first medium 182 can be a liquid medium such as an aqueous medium (e.g., a water based medium), and the second medium 184 can be a medium that is immiscible in the first medium 182. For example, the second medium 184 can comprise a gas, an oil, a non-aqueous liquid, or the like. Examples of suitable gases include air, nitrogen, oxygen, carbon dioxide, helium, or the like. Examples of suitable oils include gas permeable oils such as fluorinated oils, mineral or silicone oils, each of which may admix some gases such as the gases described above. Examples of liquids include aqueous solutions and non-aqueous solutions. Non aqueous solutions may include but are not limited to perfluorinated fluids (e.g., Fluorinert™, or other perfluorinated species containing ethereal or amino functionalities). A variety of different molecular weight range Fluorinert™ liquids are widely commercially available and may afford delivery of air to biological cells that may be isolated in the pens. An aqueous medium can be, for example, water, an aqueous buffer (e.g., a phosphate buffer, a tris(hydroxymethyl)aminomethane (Tris) buffer, or the like), an aqueous solution (e.g., containing one or more soluble active agents), cell culture medium, and the like. As shown, the media source 180 can be connected to an inlet 114 into the enclosure 102.

The media source 180 can be a device that is outside of and separate from the apparatus 100 as illustrated in FIGS. 1A and 1B. Alternatively, the media source 180 can be located in whole or in part inside the enclosure 102. For example, the media source 180 can comprise two or more reservoirs that are part of the fluidic circuit 120.

FIG. 1A also illustrates simplified block diagram depictions of examples of control equipment 152 that can be utilized in conjunction with the apparatus 100. As shown, examples of such control equipment 152 include a master controller 154, a media module 160 for controlling media in the apparatus 100, and a motive module 162 for moving micro-objects (not shown) and/or medium (e.g., droplets of medium) (not shown) in the fluidic circuit 120. The control equipment 152 can also include other modules 164 for controlling, monitoring, or performing other functions with respect to the apparatus 100.

The master controller 154 can comprise a control module 156 and a digital memory 158. The control module 156 can comprise, for example, a digital processor configured to operate in accordance with machine executable instructions (e.g., software, firmware, microcode, or the like) stored in the memory 158. Alternatively or in addition, the control module 156 can comprise hardwired digital circuitry and/or analog circuitry. The media module 160, motive module 162, and/or other modules 164 can be similarly configured. Thus, functions, processes (e.g., all or part of the processes 300, 400, 500, 2000, 2400 of FIGS. 3, 4, 5, 22, and 24), acts, actions, or steps (e.g., one or more steps of the processes 300, 400, 500, 2200, 2400 of FIGS. 3, 4, 5, 22, and 24) of a process discussed herein as being performed with respect to the apparatus 100 or any other microfluidic apparatus can be performed by one or more of the master controller 154, media module 160, motive module 162, and/or other modules 164 configured as discussed above.

The media module 160 (and/or the master controller 154) can control the media source 180. For example, the media module 160 can control the media source 180 to input a selected one of the media 182, 184 into the enclosure 102 (e.g., through an inlet 114). The media module 160 can also control removal of media from the enclosure 102 (e.g., through an outlet 116). One or more media (e.g., media 182, 184) can thus be selectively input into and removed from the apparatus 110. In various embodiments, the media 182, 184 may be flowed in and may be stopped. In some embodiments, the flow of media 182, 184 is intermittent.

The motive module 162 can be configured to control selection and movement of micro-objects (not shown) in the fluidic circuit 120. For example, all or parts of the enclosure 102 can comprise dielectrophoresis (DEP) devices such as are known in the art for selectively producing a net DEP force on a micro-object (not shown) in the fluidic circuit 120 sufficient to trap and move the micro-object (not shown). Examples of such DEP devices include electronic tweezers (ET) devices such as are known in the art. Examples of such ET devices are disclosed in U.S. Pat. No. 7,612,355 (now RE44,711), U.S. Pat. No. 7,956,339, and U.S. Patent Application Publication No. 2014/0124370. Other examples of the DEP configurations include any kind of electronically controlled electronic tweezers, an example of which is disclosed in U.S. Pat. No. 6,942,776. The foregoing US patent documents (U.S. Pat. No. 7,612,355 (now RE44,711); U.S. Pat. No. 7,956,339; U.S. Patent Application Publication No. 2014/0124370; and U.S. Pat. No. 6,942,776) are incorporated herein in their entirety by reference. The motive module 162 can be configured to control such DEP devices to select and move individual micro-objects in the fluidic circuit 120, for example, as illustrated in any of the foregoing patent documents. The power source 118 can be configured to electrically bias such DEP devices.

The motive module 162 can alternatively or in addition be configured to control electrowetting controlled movement of volumes (e.g., droplets) of medium in the fluidic circuit 120. For example, all or parts of the enclosure 102 can comprise electrowetting (EW) devices such as are known in the art for controllably changing electrowetting properties of regions of the inner surface 106 of the enclosure 102. Examples of such EW devices include optoelectronic wetting (OEW) devices examples of which are disclosed in U.S. Pat. No. 6,958,132; and U.S. patent application Ser. No. 13/194,966. The foregoing two US patent documents (U.S. Pat. No. 6,958,132; and U.S. patent application Ser. No. 13/194,966) are incorporated herein by reference in their entirety. Other examples of such EW devices include electrowetting on dielectric (EWOD) devices, which can be electronically controlled. The motive module 162 can be configured to control such EW devices to selectively move volumes (e.g., droplets) of a medium (not shown) in the fluidic circuit 120, for example, as illustrated in any of the foregoing patent documents. The power source 118 can be configured to electrically bias such EW devices (not shown).

As noted, the enclosure 102 of the apparatus 100 can comprise DEP devices (not shown) for selecting and moving micro-objects (not shown) in the fluidic circuit 120 or EW devices (not shown) for moving volumes of a medium (not shown) in the fluidic circuit 120. As yet another example, the enclosure 102 of the apparatus 100 can comprise both DEP devices (not shown) and EW devices (not shown). Examples of enclosures having both DEP devices and EW devices are illustrated in U.S. patent application Ser. No. 14/262,140, International Application No. PCT/US/2015/027679, U.S. patent application Ser. No. 14/262,200, and PCT/US/2015/027680. The foregoing US patent applications (U.S. patent application Ser. No. 14/262,140; and U.S. patent application Ser. No. 14/262,200) and International Applications (PCT/US/2015/027679 and PCT/US/2015/027680) are each incorporated herein by reference in its entirety. The motive module 162 can be configured to control such DEP devices and EW devices (not shown), for example, as illustrated in any of the foregoing patent documents. The power source 118 can be configured to electrically bias both the DEP devices and the EW devices (not shown).

FIG. 3 is an example of a process 300 by which a microfluidic apparatus like 100 or 200 can be operated. For ease of discussion and illustration, process 300 is discussed below operating on the apparatus 100 of FIGS. 1A and 1B. The process 300, however, is not so limited but can operate on other microfluidic apparatuses (e.g., the apparatus 200 of FIG. 2).

Figure 6:
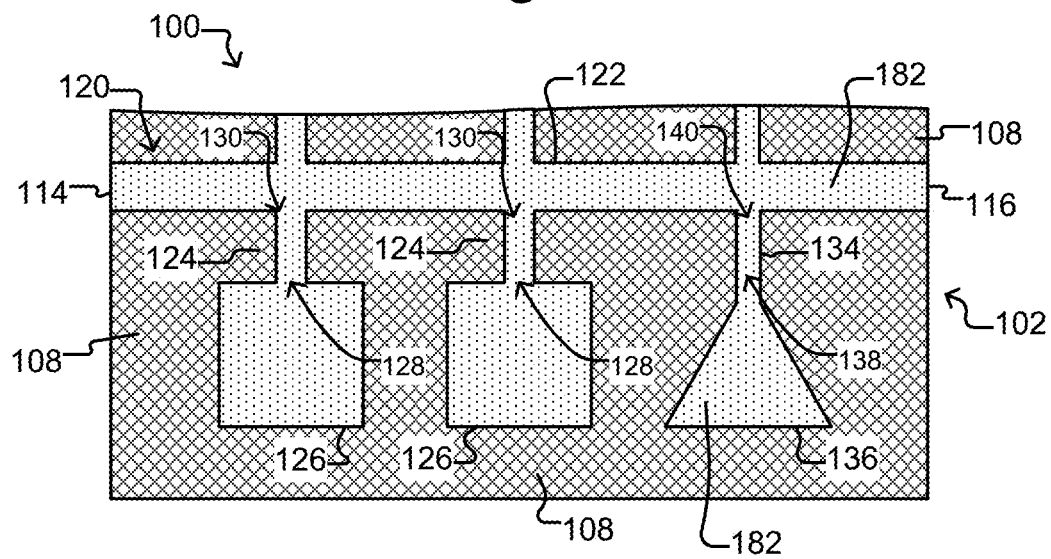
FIG. 6 illustrates an example of initializing a microfluidic apparatus with a first medium according to some embodiments of the invention.

As shown in FIG. 3, at step 302, the process 300 can initialize (e.g., prime) the microfluidic apparatus 100 with a first medium 182. Priming may include several steps or may include a simple one step process. An initial step may include purging the microfluidic apparatus 100 with 100% carbon dioxide gas prior to priming with the first medium 182. The purge may be carried out at 15 psi for 5 min. Following the carbon dioxide purge, a priming solution which may include an aqueous medium (one non-limiting example include a culture medium compatible with biological cells), and which may further contain 1% by weight of a conditioning reagent, e.g. Pluronic® F127, may be flowed for 8 min at a constant rate, such as 5 µl/sec. After completion of priming with the priming solution, a suitable culture medium or other aqueous medium may be flowed for an additional 5 min at a constant rate such as 5 µl/sec. For example, the apparatus 100 can be initialized by inputting the first medium 182 from the media source 180 into the fluidic circuit 120 of the apparatus 100. The media module 160 of FIG. 1A, for example, can control the media source 180 to fill partially or entirely the channel 122 and the pens 126, 136 with the first medium 182 as illustrated in FIG. 6. (FIGS. 6-17 show partial top views of the apparatus 100 of FIGS. 1A and 1B without the cover 110.) As another example, initializing can include fully or partially filling the fluidic circuit 120 with the first medium 182 and bringing the first medium 182 in the fluidic circuit 120 to a desired temperature, pH level, rate of the flow of the medium 182, and/or the like.

Once inside the apparatus 100, the first medium 182 can be moved in the fluidic circuit 120 in any suitable manner. For example, the media module 160 of FIGS. 1A and 1B can control fluidic pressure in the fluidic circuit 120 to move the first medium 182 in the fluidic circuit 120. As another example, the motive module 162 can be configured to move the first medium 182 in the fluidic circuit 120 by controlling electrowetting properties at regions on the surface 106 of the structure 104 (e.g., using EW devices (not shown)) as discussed above. As yet another example, the apparatus 100 can be tilted as needed so that gravity moves the first medium 182 in the fluidic circuit 120.

As illustrated by steps 304-320 of FIG. 3, the process 300 can then selectively perform a variety of actions. A subset of steps from 304-320 may be selected. Not all steps are necessarily performed when selecting any of the steps. Selected steps may be performed in differing order than as presented in FIG. 3. In discussion of process 300 in the following paragraphs, while pens 126, 136 are specifically mentioned for simplicity, any of the pen configurations along with the accompanying microfluidic channel variants described herein may be used alternatively or in combination with pens 126, 136, and process 300 is not so limited to use only pens 126, 136. Any of the microfluidic circuits, structures, and/or pens of FIGS. 26-31 may be used.

Figure 7:
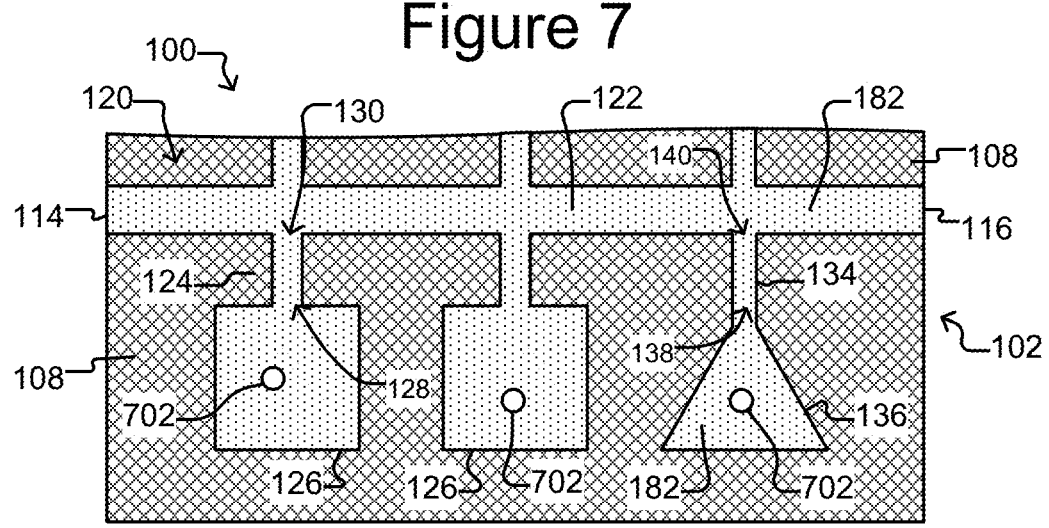
FIG. 7 shows an example of loading micro-objects into a microfluidic apparatus according to some embodiments of the invention.

For example, the process 300 can load micro-objects into the apparatus 100 (e.g., into the pens 126, 136) at step 306. An example is shown in FIG. 7 in which micro-objects 702 are loaded into the pens 126, 136. The micro-objects 702 can be biological micro-objects (e.g., biological cells) and/or inanimate micro-objects (e.g., microbeads, microrods, or the like). Although one micro-object 702 is shown in FIG. 7 in each pen 126, 136, alternatively more than one micro-object 702 can be loaded into a pen 126, 136. As another alternative, no micro-objects are loaded into some of the pens 126, 136. As yet another example, the micro-objects 702 can be biological cells, which can multiply in the pens 126, 136 resulting in, for example, clonal populations of cells in the pens 126, 136. Moreover, the micro-objects 702 need not be all the same type of micro-objects. Thus, the micro-object(s) 702 in one pen 126, 136 can be different than the micro-object(s) 702 in another pen 126, 136. Also, if there is more than one micro-object 702 in a pen 126, 136, all of the micro-objects 702 in the pen 126, 136 can be the same type of micro-object, or the micro-objects 702 in a pen 126, 136 can include different types of micro-objects.

The micro-objects 702 can be loaded into and moved inside the apparatus 100 in any suitable manner. For example, the micro-objects 702 can be loaded into the apparatus 100 through an inlet 114 by fluid flow. Similarly, micro-objects 702 can be moved within the apparatus 100 using other techniques such as the flow of media in the apparatus. Once inside the apparatus 100, individual micro-objects 702 can be selected and moved directly using DEP devices (not shown) or indirectly in droplets of a fluidic medium using EW devices (not shown) generally as discussed above.

At step 308, the process 300 of FIG. 3 can isolate one or more of the fluidic structures (e.g., the channel 122 or one or more of the pens 126, 136) in the apparatus 100 utilizing a second medium. FIG. 4 illustrates an example of a process 400 by which step 308 of FIG. 3 can be performed. As shown in FIG. 4, at step 402, the process 400 can input a volume 814 (see FIG. 8) of a second medium 184 into the fluidic circuit 120 of the apparatus 100 and move the second medium 184 to block all interfaces between the fluidic structure to be isolated and other fluidic structures of the fluidic circuit. The volume 814 can be sufficient to substantially block all fluidic interfaces to and from the fluidic structure to be isolated.

Figure 8:
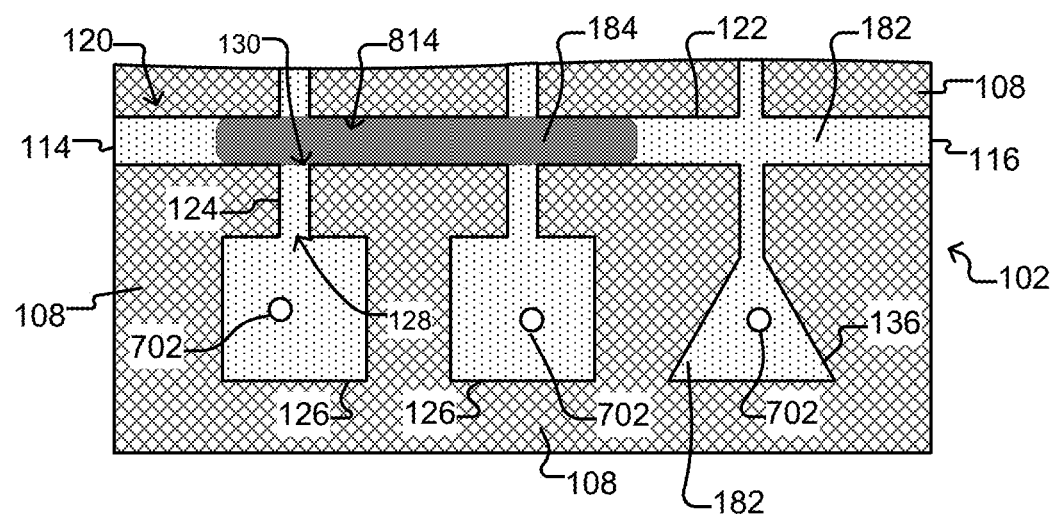
FIG. 8 is an example of isolating a fluidic structure with a second medium according to some embodiments of the invention.

FIG. 8 illustrates an example in which two of the pens 126 of the apparatus 100 are isolated by a volume 814 of the second medium 184. At step 402, the media module 160 of FIG. 1A can cause a volume 814 of the second medium 184 to be input from the media source 180 into the first medium 182 in the channel 122 of the apparatus 100, which was filled with the first medium 182 at step 302 of FIG. 3 as discussed above. At step 404, the volume 814 of the second medium 184 can be moved to a position that blocks fluidic channel openings 130 between the pens 126 to be isolated and the channel 122 as shown in FIG. 8. The volume 814 of the second medium 184 can be moved in the channel 122 in any suitable manner. For example, the media module 160 of FIGS. 1A and 1B can control fluidic pressure in the channel 122 to move the volume 814 of the second medium 184. As another example, the motive module 162 can be configured to move the volume 814 of the second medium 184 in the channel 122 by electrowetting (e.g., using EW devices (not shown)) as discussed above.

In FIG. 8, the volume 814 is shown blocking entirely the channel openings 130 of two pens 126. As shown, the channel openings 130 are the only connections (fluidic interfaces) from the pens 126 to the channel 122, and the volume 814 can thus effectively isolate each of the two pens 126 from every other circuit element (e.g., another pen 126, 136, the channel 122, or the like) in the fluidic circuit 120. Although illustrated as being disposed adjacent the channel openings 130 in FIG. 8, the volume 814 of the second medium 184 can be disposed inside the connectors 124 to the two pens 126 to be isolated and/or adjacent the pen openings 128. Using the technique illustrated in FIG. 8, one or more pens 126, 136 can be isolated.

Figure 9:
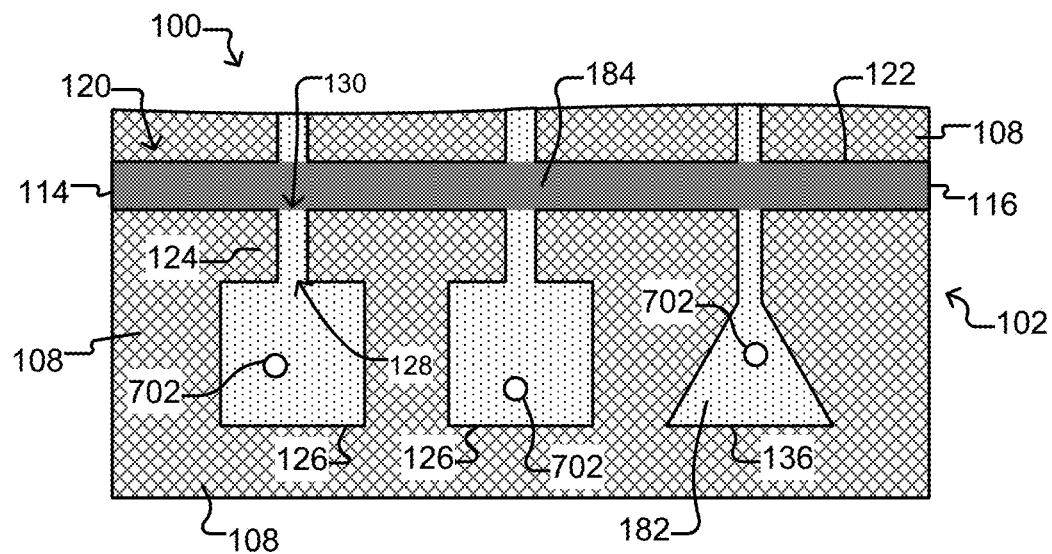
FIG. 9 is another example of isolating a fluidic structure with a second medium according to some embodiments of the invention.

FIG. 9 illustrates another example of isolating pens 126, 136 of the apparatus 100, which can thus be another example of performing step 308 of FIG. 3. As shown in FIG. 9, the first medium 182 in the channel 122 can be substantially replaced with a volume of the second medium 184. For example, the media module 160 of FIGS. 1A and 1B can control the media source 180 and the apparatus 100 to input second medium 184 from the media source 180 into the channel 122 (e.g., through an inlet 114) and remove the first medium 182 from the channel 122 (e.g., through an outlet 116). As shown in FIG. 9, the second medium 184 can block the channel openings 130, 140 to all of the pens 126, 136 and thus effectively isolate all of the pens 126, 136. Although illustrated as being disposed adjacent the channel openings 130 in FIG. 9, the second medium 184 can instead extend into the connectors 124 and can even extend to the pen openings 128.

When displacing the first medium 182 in the channel 122 by a second medium 184, it can be desirable to substantially separate the first medium 182 in a first pen 126, 136, from adjacent pens 126, 136. Surface tension between the first medium 182, the walls 108, floor (not shown), and celling (not shown) of the pens 126, 136 and channel 122 of the microfluidic apparatus and the second medium 184 in the channel 122 can allow for diffusion of a film of the first medium 182 that can connect adjacent pens 126, 136. The presence of this film may create potential concentration gradients of soluble substances present in the first pen 126, 136, and not in adjacent pens 126, 136, or vice versa. There are a number of possible strategies for breaking or significantly reducing the first medium 182 connectivity between pens 126, 136 and/or increasing the diffusion length between adjacent pens 126, 136. For example, sharp (as opposed to rounded) corners generally at or in the vicinity of the channel openings 130, 140, in the connectors 124, 134, and/or the pens 126, 136 can disrupt or substantially thin the connecting film of the first medium 182. As another example, walls of the pens 126, 136 and/or connectors 124, 134 can be hydrophilic and/or walls of the channel 122 (e.g., in the regions 131 shown in FIG. 1B) can be hydrophobic. Alternatively, there can be reduction of hydrophobicity along the path that connects the adjacent pens. As yet another example, protrusions 133 (see FIG. 1B) into the channel 122 between channel openings 130, 140 of adjacent pens 126, 136 can aid in separating the first medium 182 in the channel 122 and the first medium 182 in adjacent pens 126, 136. The protrusions can disrupt or thin the fluidic connection between adjacent pens 126, 136. The protrusions may be located at any position along the channel 122 between channel openings 130, 140 of adjacent pens 126, 136.

Pens 226 of FIG. 2 illustrate one embodiment of the isolating microfluidic structures which can diminish or eliminate fluidic connection between pens. The pens 226 have sharp corners, as discussed above, and are distributed in a flow channel 222 in varying orientations. Further, there is no structural connection between pens 226, thus decreasing fluidic connectivity as a second medium is flowed into the flow channel 222.

Figure 26:
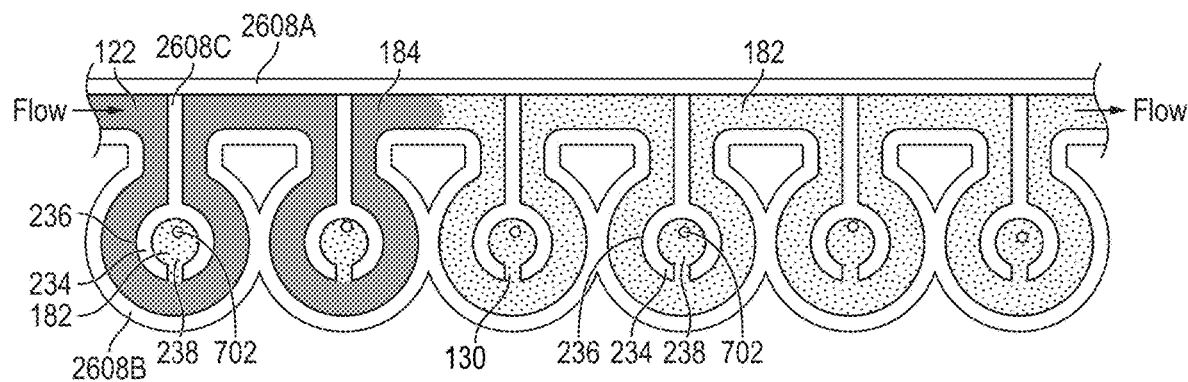
FIG. 26 is a graphical representation of another embodiment of isolating microfluidic structures of the apparatus of FIG. 1 according to some embodiments of the invention.

Some additional exemplary embodiments of isolating microfluidic structures are shown in FIGS. 26-31. A combination of features may assist in disrupting or substantially thinning connecting films of first medium 182 as second medium 184 is introduced into the fluidic channel 122 thereby isolating the pens which may contain micro-objects. In FIG. 26, pens 236 having walls 234 and interior space 238 are distributed along fluidic channel 122, each pen 236 having a pen opening 130 to the channel. The microfluidic circuit encompassing fluidic channel 122 and pens 236 is bounded by walls 2608A and 2608B. Pens 236 are connected to wall 2608A by a wall separator 2608C, which directs and lengthens the fluid connection between a first pen 236 and the next pen 236. Micro-objects 702 may present in pens 236 and be maintained/cultured in medium 182. Micro-objects 702 may be loaded into pens 236 in any way described herein (e.g., by any of flow, gravity, DEP forces including OET, or OEW). Isolating medium 184 may be introduced such that materials produced by micro-objects 702 or other reagents loaded into a specific pen do not diffuse out from a pen and thereafter diffuse into any other pen. The increased length of the flow path and the increased number of sharp corners that a thin connecting film must traverse from a first pen to an adjacent second pen help to break thin film connectivity of medium 182 as medium 184 is introduced. Comparing the flow path that a pen material must travel in the microfluidic circuit of FIGS. 1A and 1B (having only two sharp corners between the openings in pens 126, 136) and that in the microfluidic circuit of FIG. 26 (6 sharp corners and a longer flow path to be traversed), the possibility for diffusion of pen material between pens is reduced in the microfluidic circuit of FIG. 26.

Figure 27:
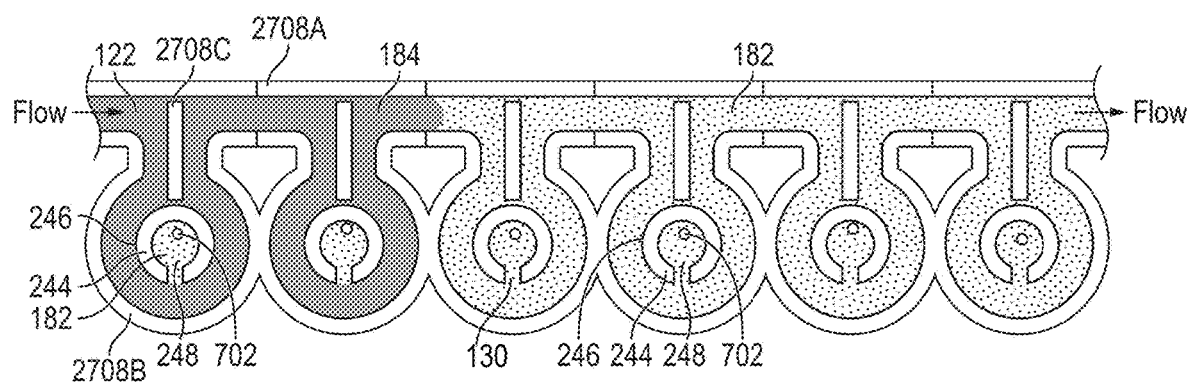
FIG. 27 is a graphical representation of another embodiment of isolating microfluidic structures of the apparatus of FIG. 1 according to some embodiments of the invention.

Another configuration of isolating microfluidic structure is shown in FIG. 27. The microfluidic structure has similar features as FIG. 26 where fluidic channel 122 traverses the circuit encompassed by walls 2708A and 2708B. Pens 246 having walls 244, interior space 248, and opening 130 to the channel 122 are distributed within the circuit, and may have micro-objects 702 loaded in any way described herein. In this embodiment, the flow separator 2708C does not connect to the wall 2708A nor to the pen wall 244, and the gaps create small breaks near each end at wall 2708A and 244 respectively, which again, help to disrupt the connectivity of thin film medium 182 between a first pen 246 and a second pen 246, as second medium 184 is flowed (F) through fluidic channel 122 to isolate the pens. The gap near wall 2708A acts to create a minor branching fluidic channel, with flow initially in the same direction as that of fluidic channel 122. A branching channel may flow in a generally similar direction at the junction of the fluidic channel 122 with the branching channel, but the branching channel diverges from the direction of the fluidic channel after the intersection of two channels, fluidic channel 122 and branching channel. In some embodiments the branching channel is a minor fluidic channel. A minor branching channel may have a width about 1%, 2, %, 3%, 4%, 5%, 6%, 7%, 8%, 9%, or 10% of the width of fluidic channel 122. The gap produced by the flow separator 2708C and pen wall 244 creates a minor fluidic channel with flow that is not parallel to that of fluidic channel 122. The width of this minor fluidic channel may be about 1%, 2, %, 3%, 4%, 5%, 6%, 7%, 8%, 9%, or 10% of the width of fluidic channel 122. The microfluidic structure in this embodiment adds further thin film disruption with two gaps as well as diffusion flow length increase and additional sharp corners.

Figure 28:
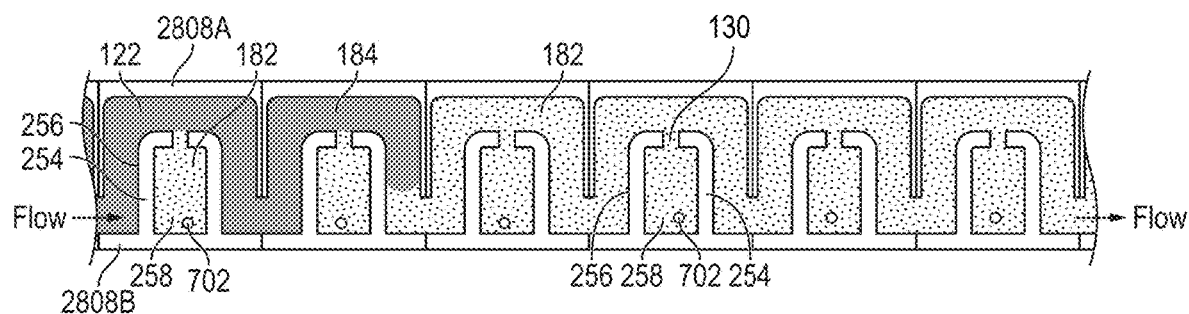
FIG. 28 is a graphical representation of another embodiment of isolating microfluidic structures of the apparatus of FIG. 1 according to some embodiments of the invention.

Yet another embodiment of isolating microfluidic structure is shown in FIG. 28. Fluidic channel 122 is contained within a microfluidic circuit encompassed by walls 2808A and 2808B. Pens 156 having walls 254 emanating from wall 2808B, interior spaces 258, and pen opening 130 to the channel 122 are distributed within the fluidic channel 122, having flow F. Micro-objects 702 may be loaded in pens 256 in any manner described herein, and may be maintained or cultured in medium 182. Medium 184 may be introduced and flowed (F) in channel 122 to isolate the pens from each other. The sharp corners at the pen opening and at flow diversions help to disrupt the thin film connectivity between adjacent pens and reduce or substantially eliminate materials produced by micro-objects 702 or other reagents placed in a specific pen 256 from diffusing into any adjacent/downstream pens.

Figure 29:
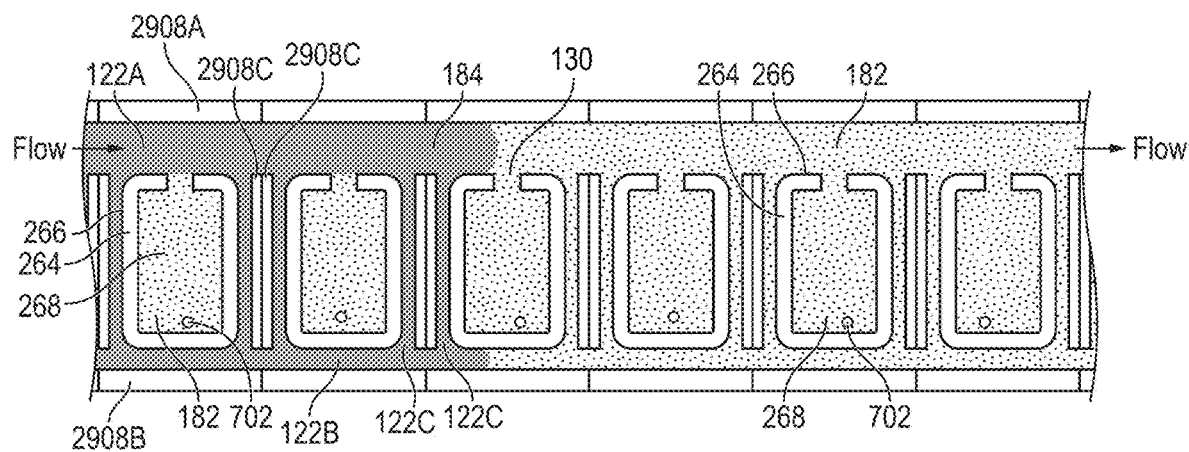
FIG. 29 is a graphical representation of another embodiment of isolating microfluidic structures of the apparatus of FIG. 1 according to some embodiments of the invention.

FIG. 29 illustrates yet another embodiment of isolating microfluidic structure. The microfluidic circuit has a flow region containing an upper fluidic channel 122A and lower fluidic channel 122B which have flow in the same direction, encompassed by walls 2908A and 2908B. Pens 266 are distributed within the flow channel and each has wall 264 enclosing interior space 268, and pen opening 130 to the channel 122. Flow separators 2908C create two minor flow channels 122C, which disrupt thin film connectivity of fluid medium 182 from adjacent pens as second medium 184 is flowed through the channel 122. The two minor flow channels 122C flow in non-parallel directions from that of upper fluidic channel 122A and lower fluidic channel 122B. Micro-objects 702 may be placed in pens by any methods described herein, and can be maintained/cultured in medium 182 whether medium 182 or medium 184 is in the fluidic channel 122.

Figure 30:
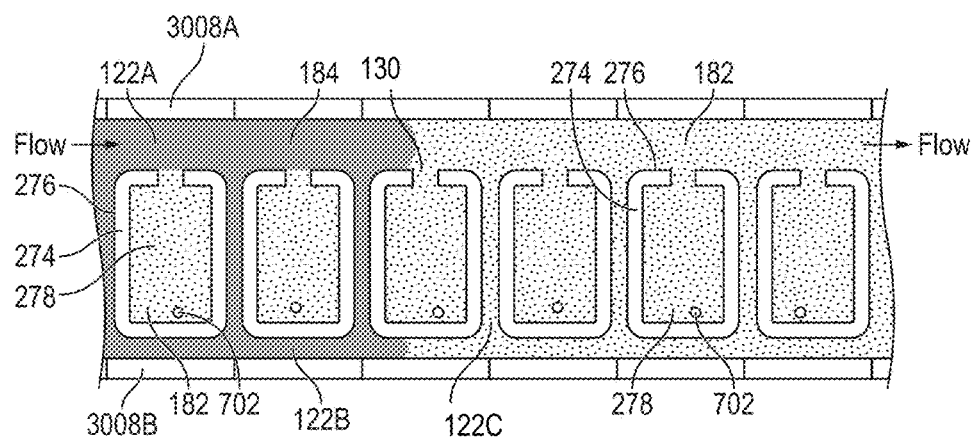
FIG. 30 is a graphical representation of another embodiment of isolating microfluidic structures of the apparatus of FIG. 1 according to some embodiments of the invention.

A further alternative embodiment of an isolating microfluidic structure is shown in FIG. 30. The microfluidic circuit has upper fluidic channel 122A and lower fluidic channel 122B encompassed by walls 3008A and 3008B. Free-standing pens 276 have include wall 274 enclosing interior space 278 and pen opening 130 to the channel 122. Flow through the upper and lower flow channel sections which is interrupted by the gaps between pens 276 provide disruption to thin film connectivity of fluid medium 182 from adjacent pens as second medium 184 is flowed through channels 122A and 122B. Micro-objects 702 may be placed in pens by any methods described herein, and can be maintained/cultured in medium 182 whether medium 182 or medium 184 is in the fluidic channel 122.

In both FIGS. 29 and 30, the fluidic channel 122A may have a larger width than fluidic channel 122B. The width of fluidic channel 122A may be about 30%, 40%, 50%, 75%, 90%, 2×, 2.5×, 3×, or about 4× larger than the width of fluidic channel 122B, or in other words, the width of fluidic channel 122B may be about 25%, 33%, 40%, 50%, 52%, 60%, 67%, 70%, or 80% of the width of fluidic channel 122A. In other embodiments, fluidic channel 122A may be about 2×, 3×, or about 5× wider than fluidic channel 122B. In some embodiments, this difference in width may be combined with selecting the width of the fluidic channel 122B to have a first width, near flow input that is larger than the width near the end of the fluidic channel 122B. In some embodiments, the first width of lower fluidic channel 122B may be about 30%, 40%, 50%, 75% or 90% larger than that of the second width of lower fluidic channel 122B. In other embodiments, the first width of lower fluidic channel 122B may be at least about 2×, 3×, or about 5× wider than the second width of fluidic channel 122B. Selecting the upper fluidic channel 122A to be larger than fluidic channel 122B in combination with narrowing of fluidic channel 122B along the microfluidic circuit may create flow intrusions into upper channel 122A via the minor fluidic channels 122C of FIGS. 29 and 30, which will tend to further disrupt thin film connectivity between adjacent pens. The minor fluidic channels 122C may have a width that is about 1%, 2%, 3%, 4%, 5%, 6%, 7%, 8%, 9% or about 10% of the width of upper fluidic channel 122A. The minor fluidic channels 122C may have a width in the range of about 1%-10%, 1%-8%, 1%-7%, 1-6%, or about 1-5% of the width of fluidic channel 122A.

Figure 31A:
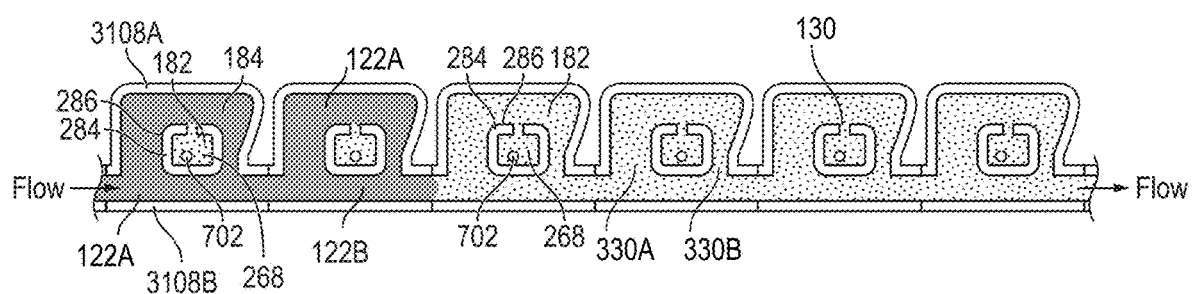
FIGS. 31A and 31B are graphical representations of other embodiments of isolating microfluidic structures of the apparatus of FIG. 1 according to some embodiments of the invention.
Figure 31B:
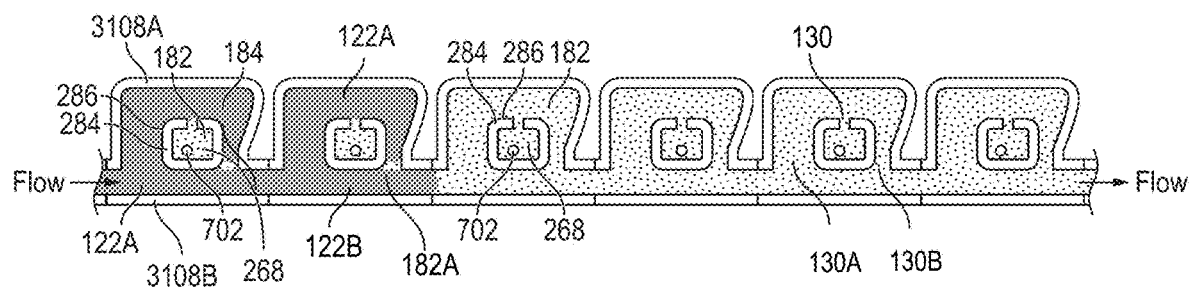

Yet another embodiment is illustrated in FIG. 31A and FIG. 31B. The microfluidic circuit has an upper fluidic channel 122A, which has a serpentine shape, with a branching fluidic channel 122B encompassed by walls 3108A and 3108B. Flow enters the microfluidic circuit within Channel 122A, but loops up and around pen 286 as it meets minor fluidic channel 122B, at the upstream bottom corner of pen 286. Fluidic channel(s) 122B runs parallel to the base of each pen 286 and branches to flow in a perpendicular direction from the flow in channel 122A as channel 122A turns to flow around pen opening 130. The shape of the channel 122A and 122B can be other than that shown here, e.g., the loop may be circular and the lower fluidic channel 122B may also include curved or semi-circular path around pens 286. Pens 286 are distributed within the flow channel, with the pen opening 130 oriented towards the serpentine upper fluidic channel 122A and oriented away from the lower channel 122B, which again disrupts fluidic connectivity between pens. Each pen has wall 284 enclosing interior space 268. The placement of pen 286 results in two fluidic channel openings 330A and 330B surrounding each pen 286. The upstream opening 330A may be larger than the downstream opening 330B. The upstream opening 330A may also be larger than the lower fluidic channel 122B. Micro-objects 702 may be placed in pens by any methods described herein, and can be maintained/cultured in medium 182 whether medium 182 or medium 184 is in the fluidic channel 122A or 122B. When immiscible fluidic medium 184 is flowed through the main fluidic channel 122A, displacing fluidic medium 182, flow of 184 will preferentially proceed along the serpentine path of channel 122A (due to the larger opening of 330A relative to that of channel 122A). This isolates the pen 286 and its contents. As flow of medium 184 continues, channel 122A narrows as it approaches the downstream channel opening 330B which has a smaller dimension than that of 330A. The fluidic medium 184 may pinch off and stop flowing at the smaller channel opening 330B, leaving a meniscus of fluidic medium 182A isolated at the opening (see FIG. 31B) to the channel at 330B or the meniscus 182A may break and fluidic medium 184 may fill the opening 330B entirely (FIG. 31A). Depending on the nature of the medium 182, medium 184, flow rate, and the dimensions of opening 330B into channel 122, the meniscus may be present or may be eradicated by flow of medium 184. In either case, the flow of medium 184 effectively isolates the fluidic medium 182 within the pen 286. In some embodiments, the branching fluidic channel 122B may have a width that is about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, or about 80% of the width of the fluidic channel 122A at the opening 330A. In various embodiments, the branching fluidic channel 122B, for example at the opening 330A is larger than a minor branching channel and may have a width that is about 20%, 25%, 30%, 35%, 40%, 45%, 50%, 55%, 60%, 65%, 70%, 75%, or about 80% of the width of the fluidic channel 122A at the opening 330A. In various embodiments, channel 122A may narrow as it rejoins channel 122B at the opening 330B and may have a width of about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 90% or about 100% of the width of the fluidic channel 122B at opening 330B.

There are many alternatives to the pens described herein, as the pens and flow channels may have different variations of shape while still performing as described herein. For example, while pens 236, 246 are shown as circular, oblong, square, rhomboid, or irregularly shaped pens would also function to isolate the interior of the pen from the flow channel. Similar changes can be envisioned for the channels surrounding the pens and all such variability is possible while providing the function of isolating a pen. Any of the isolating microfluidic structures may be used in any combination, and features from different embodiments may be combined within one microfluidic circuit. A microfluidic device may have one microfluidic circuit as described above or any number of microfluidic circuits as desired.

In some embodiments, a microfluidic apparatus has an isolating microfluidic structure including a fluidic channel and pens distributed therein. In some embodiments, the walls of pens may not be contiguous to each other, as in pens 236, 246, 256, 266, 276, 286. The fluidic channel between each pen opening 130 for pens 236, 246, 256, 266, 286 may be at least 10% longer than the linear distance separating the openings 130 to the pens 236, 246, 256, 266, 286. That is, the pens 236, 246, 256, 266, 286 may be distributed in the fluidic channel where a distance a fluidic medium flows between a first opening 130 to a first pen 236, 246, 256, 266, 286 and a second opening 130 to a second pen 236, 246, 256, 266, 286 may be at least about 10%, 20%, 50%, or about 100% longer than the linear distance between pen openings 130 for pens 236, 246, 256, 266, 286 or at least about 2×, 2.5×, 5×, 10×, or about 20× the linear distance between the first opening 130 and the second opening 130 for adjacent pens 236, 246, 256, 266, 286. The fluid flow path may be lengthened by providing a serpentine or non-linear path between adjacent pen openings 130 in the channel 122. The diffusion length between openings 130 of pens 236, 246, 256, 266, 286 may be at least about 10%, 20%, 50%, or about 100% longer than the linear distance between openings 130 of adjacent pens 236, 246, 256, 266, 286 or may be at least about 2×, 2.5×, 5×, 10×, or about 20× the linear distance between openings 130 of adjacent pens 236, 246, 256, 266, 286. In some embodiments, substantially all the fluidic medium may travel in this flow path.

In other embodiments of isolating microfluidic structures, the walls of pens may not be contiguous and portions of the microfluidic structure may provide one or more gaps in the fluidic channel. In some embodiments, about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, or about 80% of the fluidic flow may flow through gaps in the fluidic channel in a configuration that may disrupt thin film flow at surfaces of the fluid flow path. In some embodiments of isolating microfluidic structures, a fluidic channel having a flow path that is longer than the linear distance between adjacent pens is combined with the feature of having one or more gaps in the linear flow path to disrupt and thin connecting thin films between adjacent pens.

In various embodiments of pens 126, 136, 236, 246, 256, 266, 276, 286, the width $W_o$ (not shown) of a pen opening 130 can be any of the following ranges: from about 2-100 microns, 2-70 microns, 2-60 microns, 2-50 microns, 2-35 microns, 2-25 microns, 2-20 microns, 2-15 microns, 2-10 microns, 2-7 microns, 2-5 microns, 2-3 microns, 3-25 microns, 3-20 microns, 3-15 microns, 3-10 microns, 3-7 microns, 3-5 microns, 3-4 microns, 4-20 microns, 4-15 microns, 4-10 microns, 4-7 microns, 4-5 microns, 5-15 microns, 5-10 microns, 5-7 microns, 6-15 microns, 6-10 microns, 6-7 microns, 7-15 microns, 7-10 microns, 8-15 microns, about 8-10 microns, about 10-25 microns, about 30-150 microns, about 30-120 microns, about 30-100 microns, about 30-90 microns, about 30-80 microns, about 30-70 microns, or about 30-60 microns. The foregoing are examples only, and the width $W_o$ of a pen opening 130 can be different than the foregoing examples (e.g., a range defined by any of the endpoints listed above).

In various embodiments of isolating microfluidic structures, pens 126, 136, 236, 246, 256, 266, 276, 286 may have a volume of at least about $3\times10^3$, $6\times10^3$, $9\times10^3$, $1\times10^4$, $2\times10^4$, $4\times10^4$, $8\times10^4$, $1\times10^5$, $2\times10^5$, $4\times10^5$, $8\times10^5$, $1\times10^6$, $2\times10^6$, $4\times10^6$, $6\times10^6$, $1\times10^7$, $1\times10^8$ cubic microns, or more.

In some other embodiments, the isolating microfluidic structures may have pens configured as in any of the embodiments discussed herein where the microfluidic structure may have about 1500 to about 3000 pens, about 2000 to about 3500 pens, about 2000 to about 4000 pens, about 2500 to about 4000 pens, or about 3000 to about 4500 pens.

In some other embodiments, the isolating microfluidic structures may have pens configured as in any of the embodiments discussed herein where the microfluidic structure may have about 3000 to about 4500 pens, about 3500 to about 5000 pens, about 4000 to about 5500 pens, about 4500 to about 6000 pens or about 5000 to about 6500 pens.

In further embodiments, the isolating microfluidic structures may have pens configured as in any of the embodiments discussed herein where the microfluidic structure may have about 6000 to about 7500 pens, about 7000 to about 8500 pens, about 8000 to about 9500 pens, about 9000 to about 10,500 pens, about 10,000 to about 11,500 pens, about 11,000 to about 12,500 pens, about 12,000 to about 13,500 pens, about 13,000 to about 14,500 pens, about 14,000 to about 15,500 pens, about 15,000 to about 16,500 pens, about 16,000 to about 17,500 pens, or about 17,000 to about 18,500 pens.

In various other embodiments, the isolating microfluidic structures may have pens configured as in any of the embodiments discussed herein where the microfluidic structure may have about 18,000 to about 19,500 pens, about 18,500 to about 20,000 pens, about 19,000 to about 20,500 pens, about 19,500 to about 21,000 pens, or about 20,000 to about 21,500 pens.

The linear distance between openings in the pens to the microfluidic channel may be about 60 to about 2500 microns, about 100 to about 2200 microns, about 100 to about 2000 microns, about 100 to about 1800 microns, about 100 to about 1600 microns, about 100 to about 1400 microns, about 100 to about 1200 microns, about 100 to about 1000 microns, about 100 to about 800 microns, about 100 to about 600 microns, about 100 to about 500 microns, about 100 to about 400 microns, about 100 to about 300 microns, about 100 to about 200 microns, about 80 to about 2000 microns, about 80 to about 1500 microns, about 80 to about 1200 microns, about 80 to about 1000 microns, about 80 to about 800 microns, or about 80 to about 500 microns.

The width $W_c$ of the channel 122 or 122A at a channel opening 130 of pens 126, 136, 236, 246, 256, 266, 276, 286, can be any of the following ranges: from about 30-1000 microns, 30-500 microns, 30-400 microns, 30-300 microns, 30-200 microns, 30-100 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. The width $W_c$ of the channel 122B may be any of the following ranges from about 1-500 microns, about 1-250 microns, about 1-150 microns, about 1-100 microns, about 1-90 microns, about 1-80 microns, about 1-70 microns, about 1-50 microns, about 1-40 microns, about 1-30 microns, about 1-20 microns, or about 1-10 microns. The foregoing are examples only, and the width $W_c$ of the channel 122, 122A or 122B can be in other ranges (e.g., a range defined by any of the endpoints listed above). The width $W_c$ of minor flow channels 122C for the fluidic structure shown in FIG. 29 may be less than width $W_c$ of the major fluidic channels 122A and/or 122B, and may be about 50%, 40%, 30%, 20% or about 10% of the width $W_c$ for major fluidic channels 122A and/or 122B. The width $W_c$ for the fluidic channels 122, 122B shown in FIG. 31 and/or fluidic channels 122A, 122B shown in FIGS. 29 and 30 do not need to be the same but may be chosen from any of the ranges shown above, as described above for each FIG. 26-31.

The width of the channel 122A at channel opening 330A may be can be any of the following ranges: from about 30-1000 microns, 30-500 microns, 30-400 microns, 30-300 microns, 30-200 microns, 30-100 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. The width of channel 122A at channel opening 330B may be any of the following ranges from about 1-500 microns, about 1-250 microns, about 1-150 microns, about 1-100 microns, about 1-90 microns, about 1-80 microns, about 1-70 microns, about 1-50 microns, about 1-40 microns, about 1-30 microns, about 1-20 microns, about 1-10 microns, 30-500 microns, 30-400 microns, 30-300 microns, 30-200 microns, or about 30-100 microns.

The height $H_{ch}$ (not shown) of the channel 122 or 122B at a pen opening 130 (for any of the pens 126, 136, 236, 246, 256, 266, 276, 286) or for channel openings 330A or 330B (for the microfluidic structure of FIG. 31) can be selected from any of the following ranges: from about 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or about 40-50 microns. The foregoing are examples only, and the height $H_{ch}$ of the channel 122 can be in other ranges (e.g., a range defined by any of the endpoints listed above).

A cross-sectional area of the channel 122 or 122A at a pen opening 130 (for pens 126, 136, 236, 246, 256, 266, 276, 286) or the channel 122B at a channel opening 330A or 330B (pens 286) can be any of the following ranges: from about 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, about 3,000 to 6,000 square microns, about 200-1500 square microns, about 200-2000 square microns, about 200-2500 square microns, or about 200-3500 square microns. The foregoing are examples only, and the cross-sectional area of the channel 134 at a proximal opening 152, the channel 134 at a proximal opening 352, or the channel 434 at a proximal opening 472 can be in other ranges (e.g., a range defined by any of the endpoints listed above).

In some embodiments, the linear distance between openings in the pens to the microfluidic channel may be about 100 to about 2000 microns, the width $W_o$ of a pen opening 130 can be about 30-70 microns, the width $W_c$ of the channel 122 or 122A at a channel opening 130 of pens can be about 30-200 microns, and the fluidic channel 122 may be at least about 2x longer than the linear distance between openings 130 of adjacent pens. In some embodiments, the fluidic channel 122 that is at least 2x longer than the linear distance between openings 130 of adjacent pens is serpentine. In some embodiments, the microfluidic circuit may further include minor flow channels having a non-parallel direction of flow, wherein the minor flow channels have a width that is about 1%-10% of the width of major fluidic channel 122 or 122A.

In some other embodiments, the linear distance between openings in the pens to the microfluidic channel may be about 100 to about 2000 microns, the width $W_o$ of a pen opening 130 can be about 30-70 microns, the width $W_c$ of the channel 122 or 122A at a channel opening 130 of pens can be about 30-200 microns, and the fluidic channel 122 may be at least about 10% longer than the linear distance between openings 130 of adjacent pens. In some embodiments, the fluidic channel 122 that is at least 10% longer than the linear distance between openings 130 of adjacent pens is serpentine. In some embodiments, the microfluidic circuit may further include minor flow channels having a non-parallel direction of flow, wherein the minor flow channels have a width that is about 1%-10%, of the width of major fluidic channel 122 or 122A.

In some other embodiments, the linear distance between openings in the pens to the microfluidic channel may be about 100 to about 2000 microns, the width $W_o$ of a pen opening 130 can be about 30-70 microns, the width $W_c$ of the channel 122 or 122A at a channel opening 130 of pens can be about 30-200 microns, and the fluidic channel 122 may be from about 2x to about 10x longer than the linear distance between openings 130 of adjacent pens. In other embodiments, the fluidic channel 122 may be from about 2x to about 5x longer than the linear distance between openings 130 of adjacent pens. In some embodiments, the fluidic channel 122 that is at about 2x to about 10x or about 2x to about 5x longer than the linear distance between openings 130 of adjacent pens is serpentine. In some embodiments, the microfluidic circuit may further include minor flow channels having a non-parallel direction of flow, wherein the minor flow channels have a width that is about 1%-10%, of the width of major fluidic channel 122 or 122A.

In yet other embodiments, the fluidic channel 122A may have a larger width than fluidic channel 122B. The width of fluidic channel 122A may be about 30%, 40%, 50%, 75%, 90%, 2x, 2.5x, 3x, or about 4x larger than the width of fluidic channel 122B. Additionally, a first width of lower fluidic channel 122B may be at least about 2x, 3x, or about 5x wider than the second width of fluidic channel 122B. There may also be branching or minor fluidic channels present in combination with the wider channel 122A and narrower channel 122B, which also changes width as it progresses through the microfluidic circuit. The minor and/or branching fluidic channels may have a width that is about 1-10% of the width of channel 122A. In other embodiments, one or more branching fluidic channels may be present in combination with the wider channel 122A and narrower channel 122B, which also changes width as it progresses through the microfluidic circuit, where the branching fluidic channel has a width that may be about 30%-90% that of the channel 122A.

Figure 10:
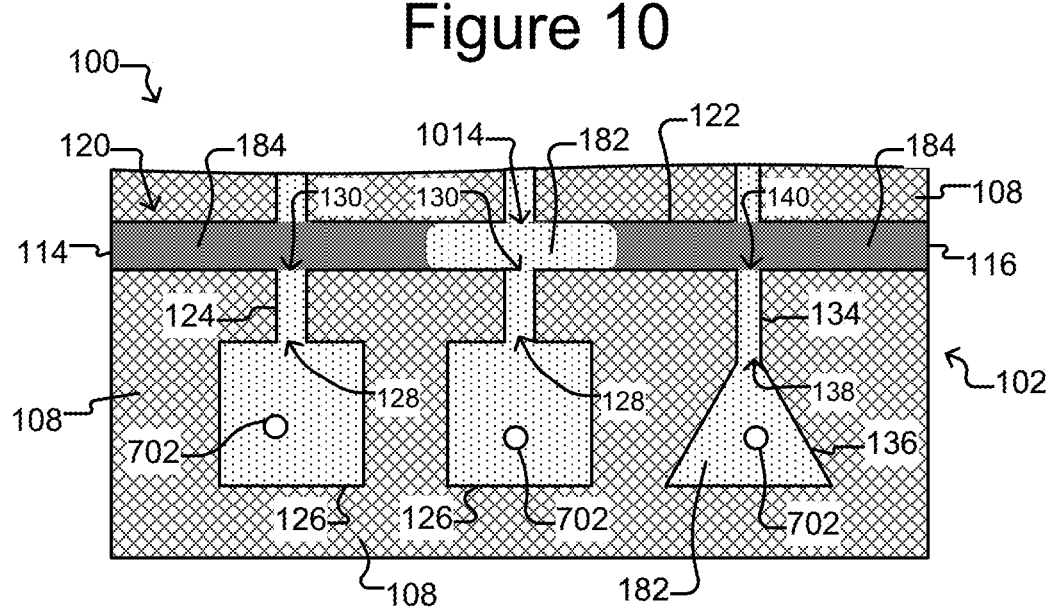
FIGS. 10-12 illustrate an example of removing a micro-object from an isolated fluidic structure according to some embodiments of the invention.
Figure 11:
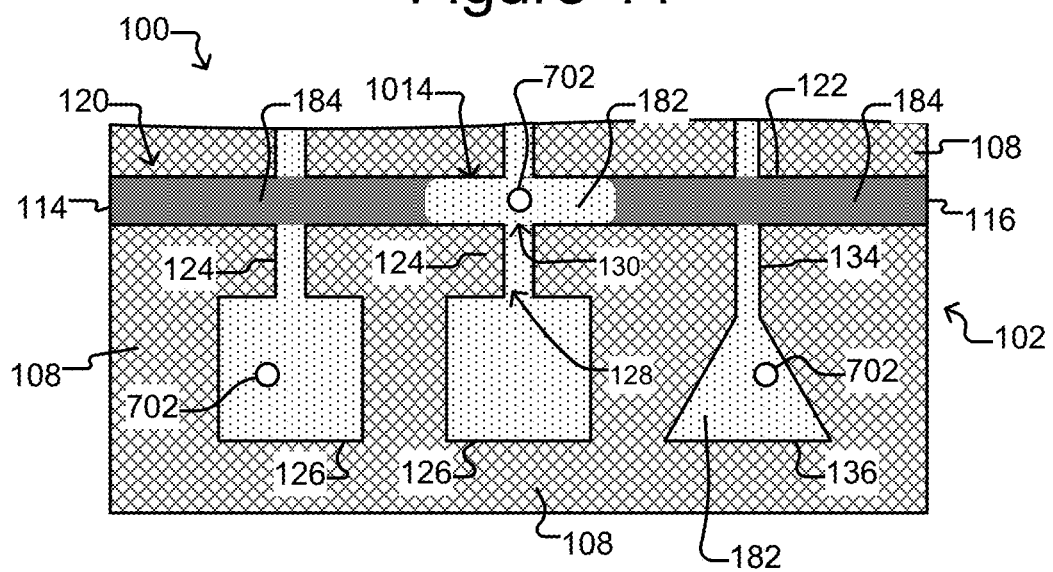
Figure 12:
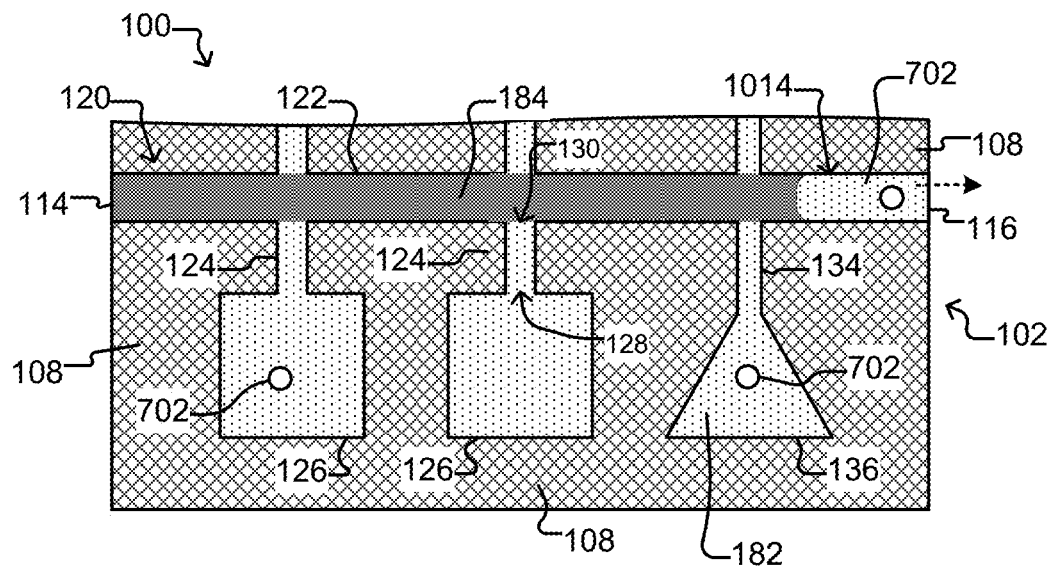

Returning to FIG. 3, at step 310, the process 300 of FIG. 3 can remove a micro-object 702 or other material (not shown) from one of the fluidic structures (e.g., a pen 126, 136) isolated at step 308. FIG. 5 illustrates an example of a process 500 by which step 310 of FIG. 3 can be performed. FIGS. 10-12 show an example of performance of the process 500 on the apparatus 100 of FIGS. 1A and 1B in which micro-objects 702 have been loaded into the pens 126, 136 as shown in FIG. 7, and the pens 126, 136 have been isolated as shown in FIG. 9.

At step 502, the process 500 of FIG. 5 can input a volume of a medium into the apparatus 100, and at step 504, the volume of the medium can be moved to a fluidic interface of the isolated fluidic structure. FIG. 10 illustrates an example in which a volume 1014 of medium (e.g., the first medium 182) can be input into the second medium 184 in the channel 122. For example, the media module 160 of FIG. 1A can cause a volume 1014 of the first medium 182 to be input from the media source 180 (see FIG. 1B) into the second medium 184 in the channel 122.

At step 504, the volume 1014 of the first medium 182 can be moved to a position adjacent the pen 126, 136 from which a micro-object 702 is to be removed. As shown in FIG. 10, the volume 1014 can be moved to a position adjacent an interface (e.g., the channel opening 130, 140 the connector 124, 134, or the pen opening 128, 138) to the pen 126, 136. The volume 1014 of the first medium 182 can be sufficient to effectively merge with the first medium 182 in the pen 126, 136 and thus create a continuous mass of the first medium 182 from the pen 126, 136 into the volume 1014 in the channel 122. The volume 1014 of the first medium 182 can be moved in the channel 122 in any suitable manner including any of the ways discussed above with respect to step 302 of FIG. 3 for moving the first medium 182 in the channel 122.

At step 506 of FIG. 5, the process 500 can move a micro-object from the pen into the volume of the medium in the channel. An example is illustrated in FIG. 11. As shown, a micro-object 702 in the pen 126 can be moved from the pen 126, through the connector 124, and into the volume 1014 in the channel 122. The micro-object 702 can be moved in any suitable manner including any of the ways for moving micro-objects 702 into the pens 126, 136 as discussed above with respect to step 306. Although one micro-object 702 is illustrated in the pen 126, 136 in FIG. 11, there can be more than one micro-object 702. In such a case, one of the micro-objects 702 in the pen 126, 136 can be selected and moved into the volume 1014 of the first medium 182 in the channel 122. Alternatively, more than one of the micro-objects 702 in the pen 126, 136 can be selected and moved into the volume 1014. For example, when the apparatus 100 includes DEP devices, a net DEP force can select one or more micro-objects 702 in pen 126 to move the micro-object(s) 702 through the connector 124 and into volume 1014 in the channel. This net DEP force can be provided, for example by an OET configuration which can initiate such forces using light.

Alternatively or in addition, at step 506, material other than a micro-object 702 can be moved from the pen 126, 136 into the volume 1014 of the first medium 182. For example, if the micro-objects 702 are biological, materials produced by a micro-object 702 in a pen 126, 136 can be moved from the pen into the volume 1014 of the first medium 182. Biological materials produced by a biological micro-object 702 can include secretions, internal material of the micro-object 702, or the like. As one example, the volume 1014 of the first medium 182 can be left at the channel opening 130, 140 to the pen 126, 136 for a time period sufficient for materials produced by a micro-object 702 in the pen 126, 136 to diffuse from the pen 126, 136 into the volume 1014 of the first medium 182. As another example, such material (not shown) can be moved from the pen 126, 136 into the volume 1014 of the first medium 182 in any manner discussed above for moving a micro-object 702 into the volume 1014.

Regardless, at step 508 of FIG. 5, the process 500 can move the volume 1014 of the first medium 182 with the micro-object 702 (and/or material from a micro-object 702) therein in the channel 122. For example, as shown in FIG. 12, the volume 1014 with the micro-object 702 (and/or material from a micro-object 702) can be moved to an outlet 116 and then removed from the apparatus 100 through the outlet 116. Alternatively, the volume 1014 of the first medium 182 with the micro-object 702 (and/or material from a micro-object 702) therein can be moved to another location (e.g., another fluidic structure such as a storage structure (not shown)) in the apparatus 100. Regardless, the volume 1014 of the first medium 182 can be moved in the channel 122 in any suitable manner including any of the ways discussed above with respect to step 302 of FIG. 3 for moving the first medium 182 in the channel 122.

In other embodiments, when the microfluidic apparatus 100 has a EW configuration including an electrowetting surface, activating EW electrodes on the electrowetting surface within a pen 126, 136 can attract a droplet of the first medium 182 which contains one or more micro-objects 702 (and/or material from a micro-object). The attracted droplet can be moved from the pen, through the connector 124 and into the channel 122 containing medium 184. The droplet of medium 182 containing the micro-object(s) (and/or material from micro-object(s)) can be moved from the intersection of the pen 126 with the channel 122 along the channel 122 (see FIGS. 11 and 12) using EW surfaces in the channel, fluid flow in the channel or gravity. The droplet of medium 182 containing the micro-object(s) (and/or material from micro-object(s)) may be moved along the channel to another pen 126, 136 or out of the microfluidic apparatus 100. Placement into another pen may be accomplished by EW forces or, if present, by DEP forces upon the droplet.

Figure 17:
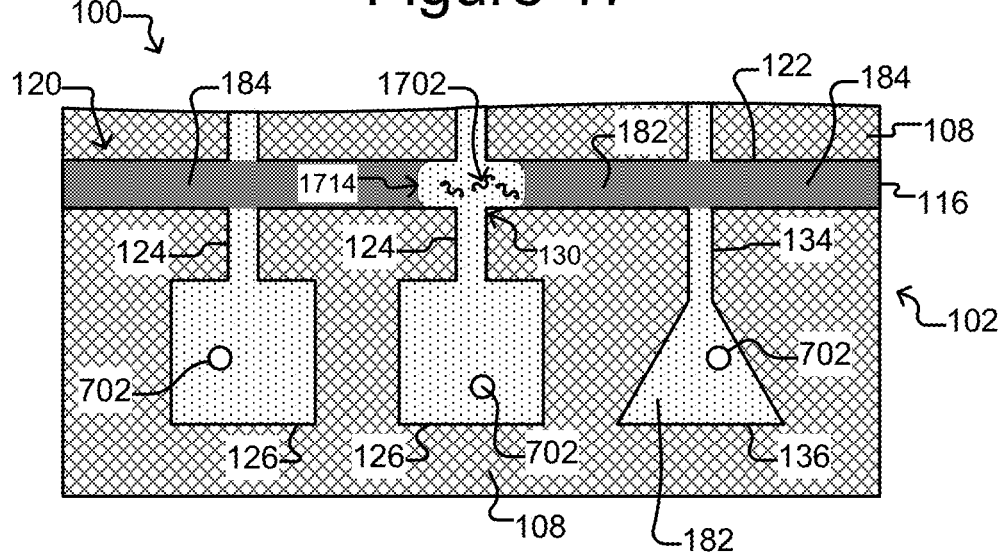
FIG. 17 is an example of diffusing material into an isolated microfluidic structure according to some embodiments of the invention.
Figure 25:
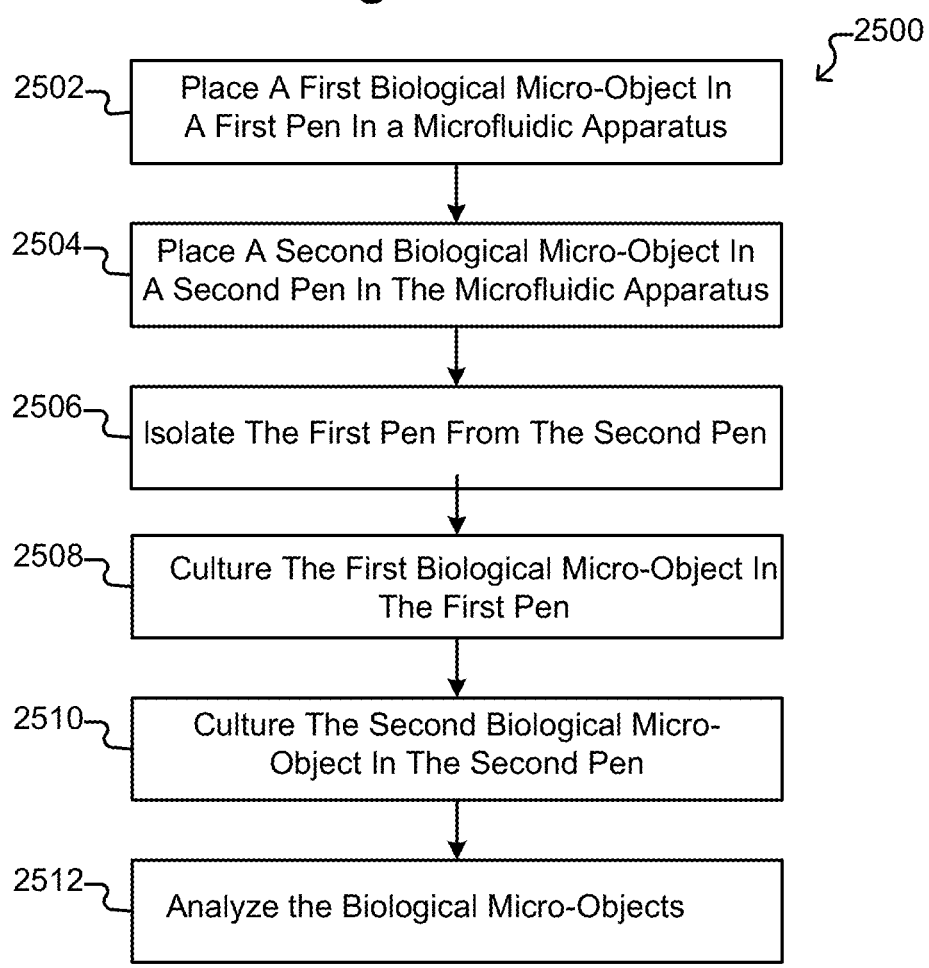
FIG. 25 shows an example of a process for culturing biological micro-objects in isolated pens and then analyzing the micro-objects or materials produced by the micro-objects according to some embodiments of the invention.

Returning again to FIG. 3, at step 312, the process 300 can culture micro-objects 702 loaded into the apparatus at step 306. As noted above, the micro-objects 702 can be biological (e.g., cells), which can be cultured for a time period and in any manner for culturing biological cells. After micro-object(s) 702 have been loaded into pens 126, 136, steps 308, 301 may not be performed. Instead, culturing (step 312) may be performed while first medium 182 is in the channel 122. Culturing the micro-object(s) 702 may include perfusing the first medium 182 to bring fresh nutrients, remove waste products and/or replenish gaseous components necessary to biological micro-object viability. In some embodiments, fresh nutrients may include soluble substances Perfusing may be continuous or non-continuous. In some embodiments, perfusing is intermittent. During intermittent perfusion, flow may be stopped for periods of time up to about 15 min, 20 min, 25 min, 30 min, 35 min, 40 min or up to about 45 min between perfusion periods. After culturing for a period of time, other micro-objects may be loaded into the pen 126, 136, using, for example, DEP (e.g., OET) or EW methods as described herein. The other micro-objects may be other types of biological cells and/or micro-object such as, for example, beads having assay/detection reagents. These other types of biological cells and/or assay/detector micro-objects may be introduced as in step 306 and used in any analysis of the cultured micro-objects(s) 702 that one of skill may find to be desirable. One example of the analysis process that can be performed is shown in FIG. 25 (process 2500). The culturing step 312 may optionally include implementation of isolation using the second medium 184 (step 308) and/or removal of an object or materials from such isolated structure (step 310) at some point after initiation of culturing. For example, if isolation of the pens 126, 136 with a second medium 184 is performed after the start of culturing, the second medium 184 in the channel 122 may be gas permeable, and nutrients in the form of gases (e.g., oxygen) can be provided through the second medium 184 in the channel 122 to the micro-object 702 in the isolated pens 126, 136. As another example, if the structure 104, the fluidic circuit 108, and/or the cover 110 are gas permeable, nutrients in the form of gases can similarly be provided through the structure 104, fluidic circuit 108, or cover 110 to the micro-object cells 702 in the isolated pens 126, 136. As yet another example, nutrients in the form of liquids or solids can be provided through openings (not shown) in the structure 104, the fluidic circuit 108, and/or the cover 110. As still another example, nutrients in the form of liquids or solids can be provided in a volume (e.g., like 1014) of the first medium 182 moved to an interface to a pen 126, 136 generally as illustrated in FIG. 17, which is discussed below. Removal of a micro-object and/or material can be performed either prior to isolation or after isolation as described herein for FIGS. 5, 11-13.

Figure 13:
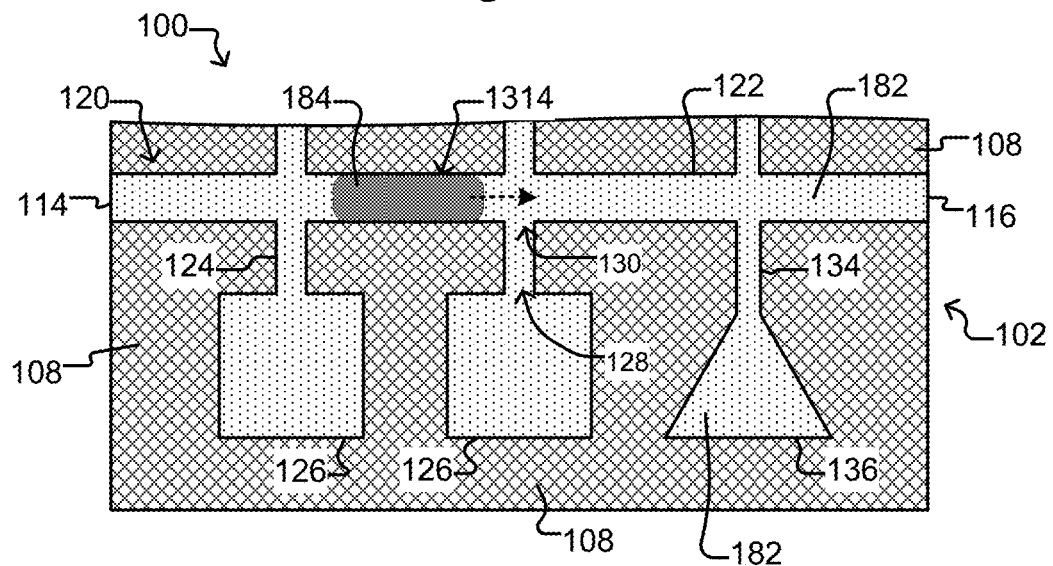
FIG. 13 shows an example of cleaning a fluidic structure according to some embodiments of the invention.

Referring again to FIG. 3, at step 314, the process 300 can clean one or more of the microfluidic structures of the microfluidic apparatus 100. One embodiment of this step introduces flow of the first medium 182 to clean the microfluidic apparatus, particularly the channel 122. Alternatively, FIG. 13 illustrates an example in which a volume 1314 of medium (e.g., the second medium 184) is introduced into and swept through the channel 122. The volume 1314 (and first medium 182 moving concomitantly with volume 1314) can clean the channel 122 of micro-objects (e.g., 702), which as noted can be cells, and/or other debris. The volume 1314 of the second medium 184 can be input into the channel 122 through an inlet 114 and removed from the channel 122 through an outlet 116. The volume 1314 of the second medium 184 can be introduced into and moved through the channel in any of the ways discussed above for introducing and moving the volume 814 of the second medium 184 in the channel 122 as discussed above for FIG. 8.

Figure 14:
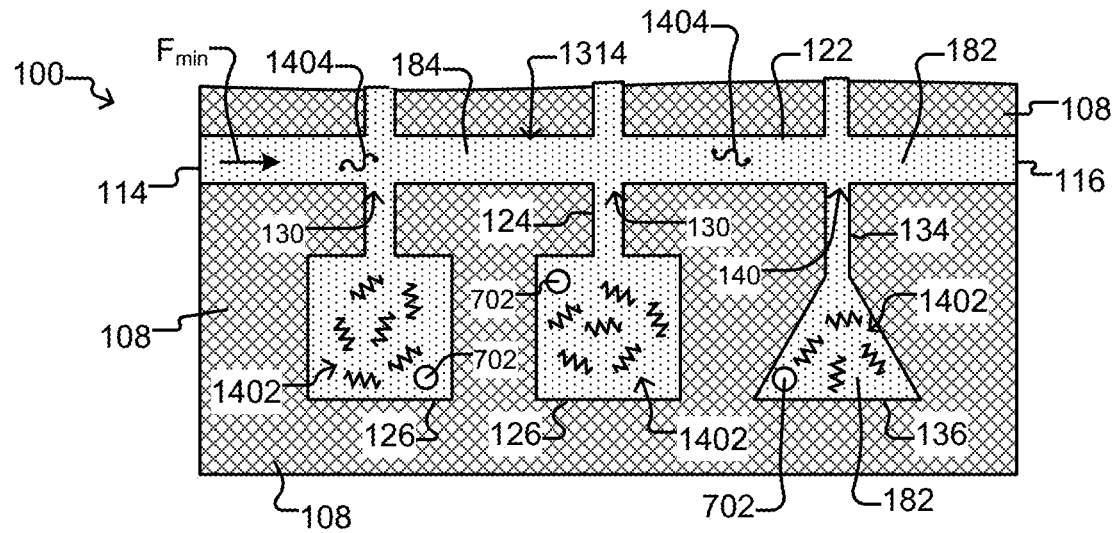
FIG. 14 is an example of isolating fluidic structures connected to a fluidic channel by inducing a flow rate of medium in a channel that substantially eliminates diffusion of pen materials between adjacent pens according to some embodiments of the invention.

At step 316, the process 300 can effectively isolate the pens 126, 136 by generating a flow of the first medium 182 in the channel 122 that is sufficiently high to reduce the concentration of materials such as a cross-contaminant that may have diffused from an upstream pen and may be present in the first medium 182 in the channel 122. The high rate of flow can resultingly reduce or substantially eliminate diffusion of such material from the first medium 182 in the channel 122 into the first medium 182 in the downstream pens 126, 136. FIG. 14 illustrates an example.

In the example shown in FIG. 14, material 1402 inside a pen 126, 136 is referred to as "pen material," and material 1404 in the channel 122 is referred to as "channel material." The pen material 1402 can be, for example, material from a micro-object 702 (which can be a biological micro-object such as a cell). The material 1402 can thus be material produced (e.g., secreted) by a micro-object in the pen 126, 136; internal material released by the micro-object 702, for example, after the micro-object is lysed; or the like. The channel material 1404 can be miscellaneous material. For example, the channel material 1404 can be pen material 1402 that has diffused from a pen 126, 136 into the channel 122.

The flow rate of the first medium 182 in the channel 122 can be set (e.g., by the media module 160 of FIG. 1A) to be greater than or equal to a minimum flow rate $F_{min}$ resulting in a decreased concentration of channel material 1404. As the channel material 1404 moves past each opening 130, 140 to a pen 126, 136, the amount of the channel material 1404 that can diffuse through a channel opening 130 into the pen 126, 136 is thereby reduced or substantially eliminated. The minimum flow rate $F_{min}$ can depend on any number of variables such as the size (e.g., cross-sectional width, diameter, area, or the like) of the openings 130, 140 from the channel 122 to the pens 126, 136 and characteristics of the first medium 182 such as viscosity, temperature, diffusion coefficient, concentration of channel material 1404, or the like. Step 316 in FIG. 3 can thus comprise inducing a rate of flow of the first medium 182 in the channel 122 that is greater than or equal to the minimum flow rate $F_{min}$. The media module 160 of FIG. 1A, for example, can control the flow rate in the channel 122 and can perform step 316 by itself or in conjunction with other means (e.g., the master controller 154). As shown in FIG. 14, the minimum flow rate $F_{min}$ of the medium 182 in the channel 122 can be in a direction that is substantially parallel to the openings 130, 140 from the channel 122 to the pens 126, 136.

Figure 15A:
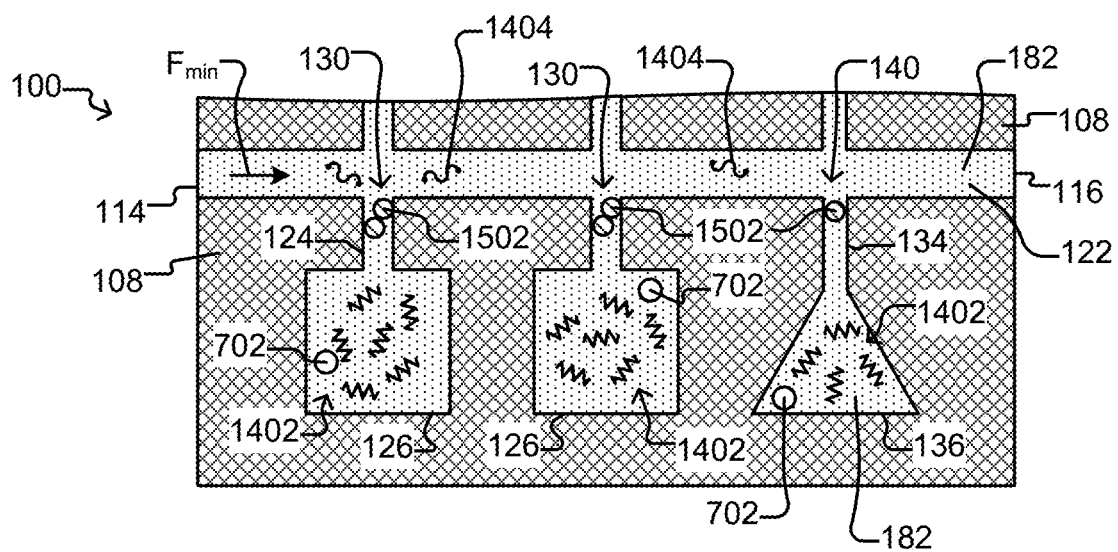
FIGS. 15A and 15B show additional examples of isolating microfluidic structures of the apparatus of FIG. 1 according to some embodiments of the invention.

At step 318, the process 300 can isolate the pens 126, 136 by placing "getters" between the pens 126, 136 and the channel 122. The "getters" can be micro-objects (e.g., microbeads, microrods, biological cells, or the like) that block the pen material 1402 and/or the channel material 1404 (see FIG. 14). FIG. 15A shows an example.

As shown in FIG. 15A, one or more micro-objects ("getters") 1502 can be placed generally at the channel openings 130, 140 (e.g., in the connectors 124, 134). A sufficient number of the micro-objects 1502 can be placed between a pen 126, 136 and the channel 122 to physically block the pen material 1402 from diffusing from a pen 126, 136 into the channel 122 and/or to physically block channel material 1404 from diffusing from the channel 122 into the pen 126, 136.

Alternatively or in addition, the micro-objects 1502 can comprise a material that binds one or both of the pen material 1402 and/or the channel material 1404. For example, the micro-objects 1502 can be micro-objects coated with a material that binds the pen material 1402 and/or the channel material 1404. Examples of such coatings can include poly dT tails (for binding mRNA), biotin-streptavidin, and antibodies for binding particular antigens. Additional examples of binding mechanisms can include hydrophobic/hydrophilic interactions, covalent linkages, non-specific binding, and electrostatic attractions. Micro-objects 1502 may be magnetic or may be non-magnetic. Micro-objects 1502 having a surface that binds pen material or channel material 1404 using hydrophobic interactions may include latex beads that strongly bind any hydrophobic material. Micro-objects 1502 may alternatively be polystyrene, glass or silica core beads and have surface treatments or coatings that render the surface of the bead hydrophobic. Surface treatments that render beads hydrophobic include materials that have long chain alkyl, alkenyl or alkynyl moieties such as organosilanes, siloxanes, carboxyl acids, or carboxylic amines/amides. Other types of chemical moieties may be included within the bead surface treatments such as cyano or amino functionalities that modulate the hydrophobicity of the final micro-object 1502. Alternatively, surface treatments for polystyrene, glass or silica beads include surface coating that provide hydroxyl, carboxylic or amino groups at the surface of the bead. One example are hydrophilic Dynabeads® (Thermo Fisher Scientific) Besides having carboxylic or amino functionalities available on the bead surface which can form covalent attachments to pen or channel materials, micro-objects 1502 can be modified to display biotin, avidin or any suitably functionalized antibody or antigen. A wide variety of such functionalized beads are commercially available from Spherotech, Inc, Bangs Laboratories, Thermo Fisher Scientific, for some nonlimiting examples.

The micro-objects 1502 can thus physically block and/or bind any pen material 1402 that starts to diffuse from a pen 126, 136 into the channel 122, and/or the micro-objects 1502 can physically block and/or bind any channel material 1404 that starts to diffuse from the channel 122 into a pen 126, 136. The micro-objects 1502 can thus substantially eliminate or reduce diffusion of pen material 1402 into the channel 122 and/or diffusion of channel material 1404 into a pen 126, 136 regardless of the flow rate of the first medium 182 in the channel 122, which can thus be between substantially zero and the minimum flow rate $F_{min}$ discussed above with respect to FIG. 14. Alternatively, the first medium 182 can be flowed at a rate that is greater than or equal to the minimum flow rate $F_{min}$ discussed above with respect to FIG. 14.

Figure 15B:
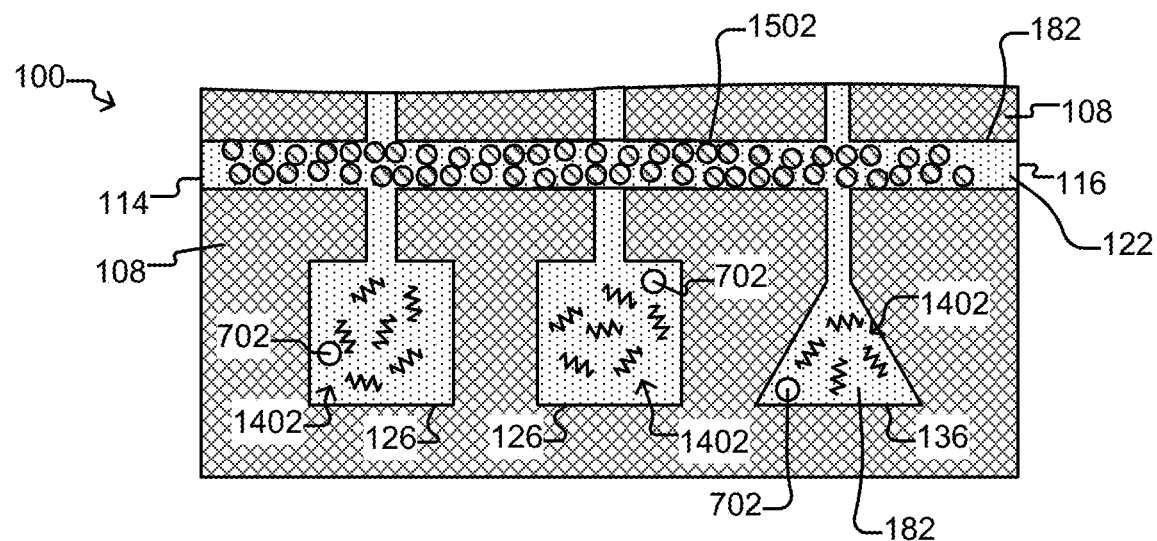

Rather than place micro-objects 1502 at the connections 124, 134 between pens 126, 136 and the channel 122, the channel 122 can be substantially filled with micro-objects 1502, for example, as shown in FIG. 15B. The range of concentration of micro-objects 1502 that may be used to block and/or absorb pen material 1402 needs to be high enough to capture most of the pen material within a short distance from the openings 130 to the channel 122 and not so high as to cause clogging in the microfluidic apparatus 100. The micro-objects may have any suitable shape including but not limited to round, spheroid, irregular or cubic. The micro-objects may have a dimension, such as a diameter or cross-section, which characterizes a size of the micro-object permitting use within the channel 122 without clogging. In some embodiments, the dimension such as the diameter or cross-section of the micro-object 1502 may be in a range of about 1-80 microns, about 5 to 75 microns, about 5 to about 60 microns, about 5 to about 50 microns, about 5 to about 40 microns, about 5 to about 30 microns, about 5 to about 20 microns or about 5 to about 10 microns. In some embodiments, the diameter or cross section of the micro-objects 1502 may be about 1, 2, 3, 4, 5, 6, 7, 8, 9, or 10 microns. In other embodiments, the sizes of the micro-objects 1502 range in size, and in some embodiments, the diameter or cross section of the micro-objects 1502 may be in a range of about 1 to about 50 microns, about 3 to about 30 microns, about 3 to about 20 microns, or about 3 to about 10 microns. A concentration of micro-objects 1502 which may fill the channel 122 may be in the range of about $1\times e^5$ beads/ml to about $1\times e^{10}$ beads/ml, about $1\times e^6$ beads/ml to about $1\times e^{10}$ beads/ml, about $1\times e^7$ beads/ml to about $1\times e^{10}$ beads/ml, or about $1\times e^7$ beads/ml to about $1\times e^9$ beads/ml. In some embodiments, the micro-objects may be flowed into the channel 122 using a concentration of $1\times e^8$ beads/ml where the beads have a diameter size of 8 microns. As another example of an alternative, binding material for binding pen material 1402 and/or channel material 1404 can be disposed (e.g., as a coating) on walls of the connectors 124, 134 between the pens 126, 136 and the channel 122.

Figure 16:
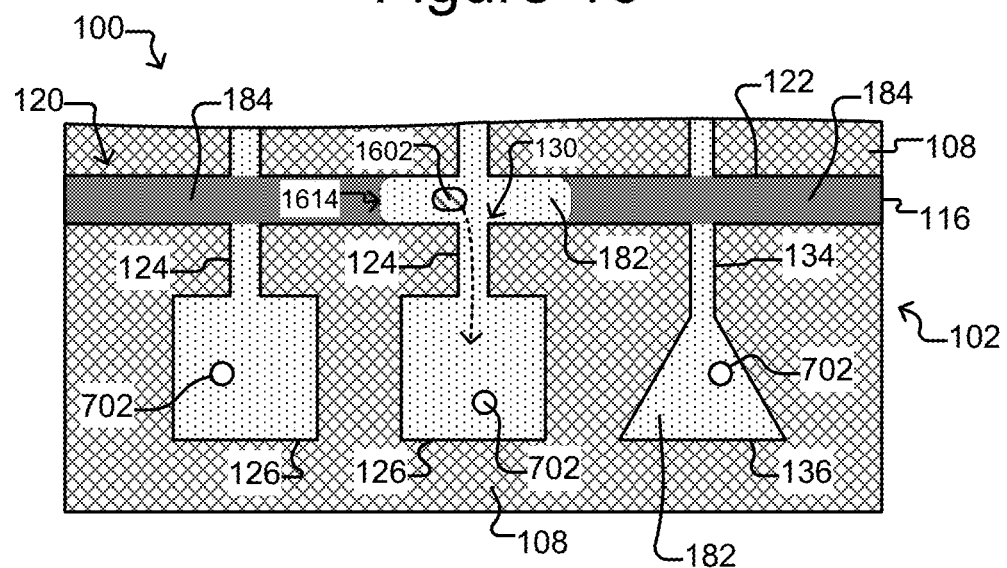
FIG. 16 illustrates an example of placing another micro-object into an isolated microfluidic structure according to some embodiments of the invention.

Referring again to FIG. 3, at step 320, the process 300 can place another micro-object or other material into a pen 126, 136, which can be one of the pens 126, 136 isolated at step 308. FIG. 16 illustrates an example in which another micro-object 1602 is placed into an isolated pen 126, and FIG. 17 shows an example in which material 1702 is allowed to diffuse into an isolated pen 126.

Referring first to FIG. 16, the micro-object 1602 can be any of the types of micro-objects discussed above with respect to micro-objects 702. For example, micro-object 1602 can be an inanimate micro-object configured to bind biological material produced by a micro-object 702 (which, as discussed above, can be biological) previously placed into the pen 126, 136 at step 306. As shown in FIG. 16, the micro-object 1602 can be included in a volume 1614 of the medium (e.g., the first medium 182) introduced into the channel 122 and moved to an interface (e.g., the channel opening 130, 140) to the pen 126, 136 generally as illustrated in FIG. 16 and discussed above. The volume 1614 of first medium 182 can be moved in the channel 122 generally as discussed above with respect moving the volume 1014 of FIG. 10. The micro-object 1602 can then be moved from the volume 1614 of the first medium 182 into the pen 126, 136 as also shown in FIG. 16. The micro-object 1602 can be moved in any way discussed herein for moving micro-objects in a medium. Rather than introducing the micro-object 1602 in a volume 1614 of the first medium 182, the micro-object 1602 can be placed into a pen 126, 136 at step 320 through an opening (not shown) in the structure 104, the fluidic circuit 108, and/or the cover 110, if such an opening is present.

As shown in FIG. 17, material 1702 for a pen 126, 136 can be included in a volume 1714 of medium (e.g., the first medium 182) introduced into the channel 122 and moved to an interface (e.g., the channel opening 130, 140) to the pen 126, 136 generally as illustrated in FIG. 17. The volume 1714 of first medium 182 can be moved in the channel 122 generally as discussed above with respect to moving the volume 1014 of FIG. 10. The volume 1714 of the first medium 182 can be at the opening 130, 140 for a time that is sufficient for the material 1702 to diffuse from the volume 1714 into the pen 126, 136. The material 1702 can by any of many possible types of materials. For example, the material 1702 can comprise nutrients for the micro-objects 702 in a pen 126, 136; biological labels for tagging an analyte in a pen 126, 136; or the like.

As another example, the material 1702 or the volume 1714 of medium itself can be a reagent for a pen 126, 136. For example, the material 1702 can be a lysing agent. Alternatively, the medium of the volume 1714 can itself be a reagent (e.g., a lysing agent). In the latter case, there may not be material 1702 in the volume 1714 because the medium of the volume 1714 is the material that is to be diffused into a pen 126, 136. Thus, after being placed at the channel opening 130, 140 to a pen 126, 136, the volume 1714 (of the reagent) can be allowed to diffuse into the pen 126, 136. Rather than introducing the material 1702 in a volume 1714 of the first medium 182, the material 1702 (or the volume 1714 of a reagent) can be placed into a pen 126, 136 at step 320 through an opening (not shown) in the structure 104, the fluidic circuit 108, and/or the cover 110, if such an opening is present. In embodiments having EW devices and surfaces, a droplet containing a reagent can be generated by EW by attraction, out of a larger volume containing reagent. The droplet may be generated within a droplet generator component (not shown) either in a location within the microfluidic apparatus or may be located outside of the microfluidic apparatus itself, In any case, the droplet generator component may be fluidically connected with the fluidic channel 122. The volume 1714 of reagent needed to perform an analysis may be one or more droplets so generated. Each of the droplet(s) containing a reagent (and eventually summing to comprise volume 1714) can then be pulled through the channel 122 by EW forces on the EW surface when the channel is filled with medium 184, and the droplet(s) delivered to a pen 126 and merged with the first medium 182 therein. Analysis using the reagent so delivered may follow delivery of the volume 1714. Analyses which may be performed include but are not limited to polymerase chain reaction (PCR) of pen material(s), lysis of biological cells, a controlled volume assay, or release of toxic reagents into pens to assess activity upon biological cells. Any sort of processing and/or assaying of biological cells or material produced by the cell that may be compromised in its accuracy by being connected by fluid to other cells or biological materials produced by cells in adjacent pens can be performed using selected steps of this process. Additionally, multiple rounds of loading micro-objects 702 (including biological cells) can be performed using step 306 at multiple points in the process, and can include isolation steps in between the cell loading steps.

Steps 306-320 of FIG. 3 are thus examples of actions that can be performed on the apparatus 100 of FIGS. 1A and 1B after the apparatus 100 is initialized at step 302 as discussed above. These actions are examples only, and many other actions can also be taken. Moreover, the actions represented by steps 306-320 can be performed in a variety of orders.

For example, micro-objects 702 in the form of biological cells can be loaded into pens 126, 136 at step 306, and the pens 126, 136 can then be isolated at step 308, 316, or 318. The micro-objects 702 (e.g., cells) in the pens 126, 136 can then be cultured at step 312. Micro-objects 1602 (e.g., inanimate micro-objects configured to bind a biological material of interest produced by a micro-object 702 in a pen 126) can be placed into the pen 126, 136 with the micro-object 702 at step 306 or step 320. Step 320 can be performed, for example, any time after isolating the pens 126, 136 at step 308, 316, or 318. Step 310 can then be performed to select and remove one of the micro-objects 702, 1602 from a pen 126, 136. At any time before, during, or after such a process, step 314 can be performed to clean the channel 122.

In another example, micro-objects 702 in the form of biological cells can be loaded into pens 126, 136 at step 306, and the micro-objects 702 (e.g., cells) in the pens 126, 136 can then be cultured at step 312, followed by isolation of the pens 126, 136, at step 308, 316 or 318. Micro-objects 1602 (e.g., inanimate micro-objects configured to bind a biological material of interest produced by a micro-object 702 in a pen 126) can then be placed into the pen 126, 136 with the micro-object 702 at step 306 or step 320, using DEP forces (including OET) or EW forces as described. Additionally or alternatively, volume 1714 containing material 1702 can be delivered to pens 126, 136 to provide reagents either before or after introduction of micro-objects 1602. Delivery of volume 174 can be performed using DEP forces (including OET) or EW forces as described. Analysis of the micro-object(s) 702 can then be performed as in process 2500. Analysis may be performed on all micro-objects 702, one selected micro-object 702 or any subset of micro-objects 702. At any time before, during, or after such a process, step 314 can be performed to clean the channel 122.

In yet another example, micro-objects 702 in the form of biological cells can be loaded into pens 126, 136 (step 306), and the micro-objects 702 (e.g., cells) in the pens 126, 136 can then be cultured at step 312, where the culturing step may be preceded or followed by the step of isolation of the pens 126, 136, at step 308, 316 or 318. After culturing has been performed for a period of time, one or more micro-objects can be selected and removed from the pens 126, 136 using DEP forces (including OET) or EW forces as described (step 310). The one or more selected micro-object(s) 702 may be moved into yet another pen 126, 136, using DEP forces (including OET) or EW forces as described (step 306). Alternatively, the micro-object(s) may be exported by moving the micro-object(s) through the channel 122 and out of the apparatus, which may also be performed using DEP forces (including OET) or EW forces as described or by fluid flow.

FIGS. 1A, 1B, 2, and 26-31 thus illustrate example configurations of a microfluidic apparatus 100, 200, and FIGS. 3-17 illustrate examples of operation of the apparatus 100 (or 200) including utilizing different media 182, 184 from the media source 180.

The ability to trap, remove, or otherwise control bubbles in fluidic medium in a microfluidic apparatus can be desirable in some circumstances. FIGS. 18-23 and 33-35 illustrate examples of configurations of fluidic structures and processes for controlling bubbles in a medium in a fluidic circuit (e.g., like 120 in FIGS. 1A and 1B) of a microfluidic apparatus.

Figure 18:
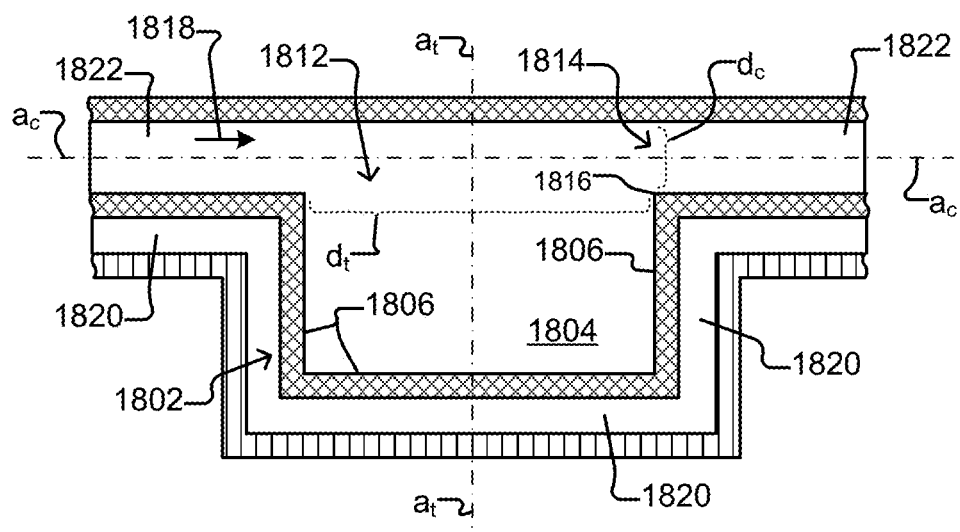
FIG. 18 illustrates an example of a bubble trap connected to a fluidic channel according to some embodiments of the invention.

FIG. 18 illustrates a partial view of a fluidic channel 1822 and an example of a bubble trap 1802 for trapping bubbles in a fluidic medium in the channel 1822. The channel 1822 and the bubble trap 1802 can be structures that are part of a fluidic circuit (e.g., like 120) of a microfluidic apparatus (e.g., like 100). The channel 1822 and the bubble trap 1802 can thus be part of the fluidic circuit 120 of the apparatus 100 of FIGS. 1A and 1B. The bubbles can be of any fluid that is immiscible in the fluidic medium in the channel 1822. For example, the bubbles can be gas bubbles (e.g., air bubbles), bubbles of oil, or the like.

As shown, a flow path 1818 of the channel 1822 can be oriented along a channel axis $a_c$. The bubble trap 1802 can comprise a trap chamber 1804 with an opening 1812 to the channel 1822. In some embodiments, the trap opening 1812 can be substantially parallel to the channel axis $a_c$. The trap chamber 1804 can comprise walls 1806 and can be oriented along a trap axis $a_t$, which can be substantially perpendicular to the trap opening 1812. The trap axis $a_t$ can be oriented at a non-zero angle with respect to the channel axis $a_c$ (and thus the trap opening 1812) so that the channel axis $a_c$ and the trap axis $a_t$ are not parallel. For example, in some embodiments, the trap axis $a_t$ can be substantially perpendicular to the channel axis $a_c$ as shown in FIG. 18.

The cross-sectional area of the trap opening 1812 can be larger than a cross-sectional area of the channel 1822 at an outer edge 1816 of the trap opening 1812 and perpendicular to the direction of the flow path 1818. (Hereinafter the cross-section of the channel 1822 at the outer edge 1816 of the trap opening 1812 is referred to as the channel opening 1814.) That is, the size $d_t$ of the trap opening 1812 can be larger (e.g., at least one and a quarter times larger, at least one and a half times larger, at least two times larger, at least three times larger, at least five times larger, or more) than the size $d_c$ of the channel opening 1814. The size $d_t$ of the trap opening 1812 and the size $d_c$ of the channel opening 1814 can be in units of distance (e.g., a diameter or width, wherein height is understood to be constant), area, or the like.

In some embodiments, one or more of the walls 1806 of the chamber 1804 can be gas permeable and thus allow gas bubbles trapped by the bubble trap 1802 to pass through the wall or walls 1806. For example, a gas permeable wall 1806 can comprise a gas permeable material (e.g., PDMS). As another example, a gas permeable wall 1806 can comprise passages (e.g., micro sized passages) that allow gas to escape through the wall 1806. As shown in FIG. 18, some embodiments can also include an outgas channel 1820 disposed adjacent one or more of the walls 1806 of the bubble trap 1802 to capture and conduct to a collection or disposal point (not shown) gas from the gas bubbles trapped by the bubble trap 1802.

Figure 19:
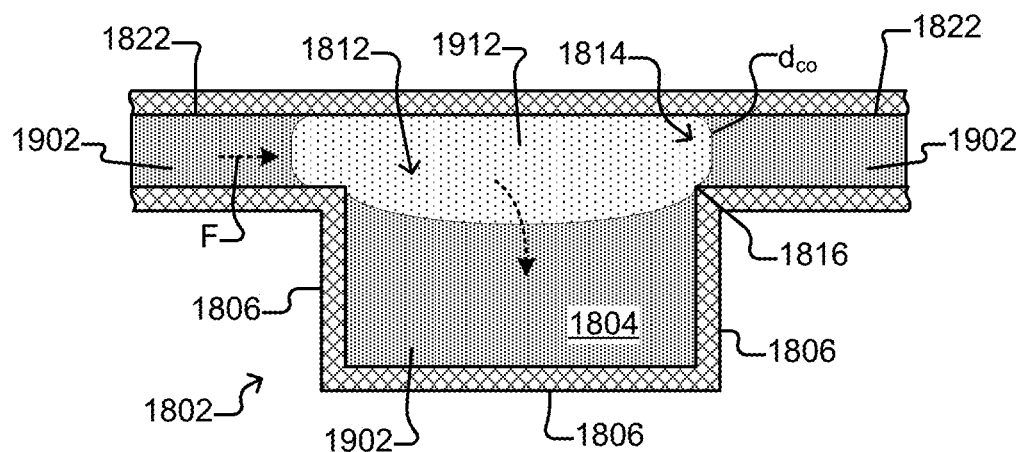
FIG. 19 is an example of the bubble trap of FIG. 18 trapping a bubble according to some embodiments of the invention.

Because the size $d_t$ of the trap opening 1812 is larger than the size $d_c$ of the channel opening 1814, the radius of curvature of the bubble surface of a bubble located at the channel opening 1814 is smaller than the radius of curvature of the bubble surface of a bubble located at the trap opening. As a result, there is a pressure drop across a bubble in the channel 1822 that forces the bubble into the trap chamber 1804 that minimizes the bubble's surface area. An example is illustrated in FIG. 19, which shows a bubble trap 1802 having similar features as that of bubble trap 1802 of FIG. 18 and having a flow F of fluidic medium 1902, including bubble 1912, in the channel 1822. Bubble trap 1802 of FIG. 19 has a trap chamber 1804, walls 1806, trap opening 1812 that is larger than channel opening 1814 at inner corner 1814, as that the bubble trap of FIG. 18. As discussed above, as the bubble approaches trap 1802, the most energetically favorable position of the bubble will be inside of the trap. The bubble trap 1802 can thus remove gas bubbles (like 1912) from a medium 1902 flowing in the channel 1822.

Although the trap chamber 1804 is illustrated in FIGS. 18 and 19 as close-ended (e.g., comprising walls 1806 on all sides except the trap opening 1812), the trap chamber 1804 can instead be open-ended. For example, the wall 1806 at the bottom of the trap chamber 1804 in FIGS. 18 and 19 can be replaced with an opening (not shown), which can lead to another fluidic structure (e.g., a reservoir) (not shown), an outlet (e.g., like 116 in FIGS. 1A and 1B), or the like.

Figure 20:
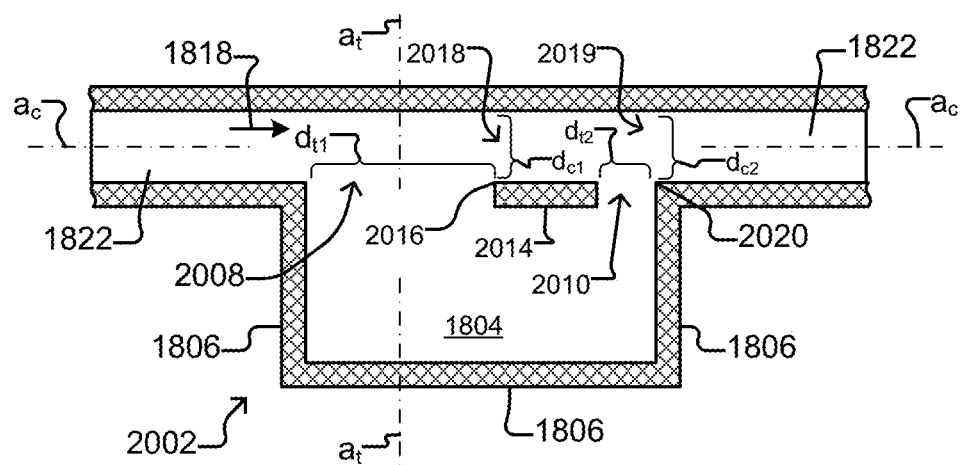
FIG. 20 shows another example of a bubble trap connected to a fluidic channel according to some embodiments of the invention.

The bubble trap 1802 illustrated in FIGS. 18 and 19 is but an example and variations are contemplated. FIG. 20 illustrates one such example: bubble trap 2002.

As shown, the bubble trap 2002 can be generally similar to the bubble trap 1802 except that the bubble trap 2002 can comprise a barrier 2014 at an interface to the channel 1822. The barrier 2014 can be, for example, part of a wall of the channel 1822. Alternatively, the barrier 2014 can be another wall 1806 of the chamber 1804. Regardless, as shown in FIG. 20, the barrier 2014 can create two openings 2008, 2010 from the trap chamber 1804 to the channel 1822. The first trap opening 2008 can have a size $d_{t1}$, and the second trap opening 2010 can have a size $d_{t2}$.

The size $d_{t1}$ of the first trap opening 2008 can be larger than the size $d_{c1}$ of a cross-section of the channel 1822 at an outer edge 2016 of the first trap opening 1808 along the flow path 1818 in the channel 1822. (Hereinafter the cross-section of the channel 1822 at the outer edge 2016 of the first trap opening 2008 is referred to as the first channel opening 2018.) In contrast, the size $d_{t2}$ of the second trap opening 2010 can be smaller than the size $d_{c2}$ of a cross-section of the channel 1822 at an outer edge 2020 of the second trap opening 2010 along the flow path 1818 in the channel 1822. (Hereinafter the cross-section of the channel 1822 at the outer edge 2020 of the second trap opening 2010 is referred to as the second channel opening 2018.) The sizes $d_{t1}$, $d_{t2}$, $d_{c1}$, $d_{c2}$ can be, for example, in units of distance (e.g., diameter, width, or the like, where height is understood to be constant), area, or the like. In some embodiments, the size $d_{t1}$ of the first trap opening 2008 can be, for example, at least one and quarter times larger, at least one and a half times larger, at least two times larger, at least three times larger, at least five times larger, or more than the size $d_{c1}$ of the first channel opening 2018. In some embodiments, the size $d_{c2}$ of the second channel opening 2019 can be, for example, at least one and quarter times larger, at least one and a half times larger, at least two times larger, at least three times larger, at least five times larger, or more than the size $d_{t2}$ of the second trap opening 2010.

In some embodiments, the sizes $d_{c1}$, $d_{c2}$ of the channel openings 2018, 2019 can be substantially equal. In such an embodiment the size $d_{t1}$ of the first trap opening 2008 can be greater than the sizes $d_{c1}$, $d_{c2}$ of the channel openings 2018, 2019, which can be greater than the size $d_{t2}$ of the second trap opening 2010.

Figure 21:
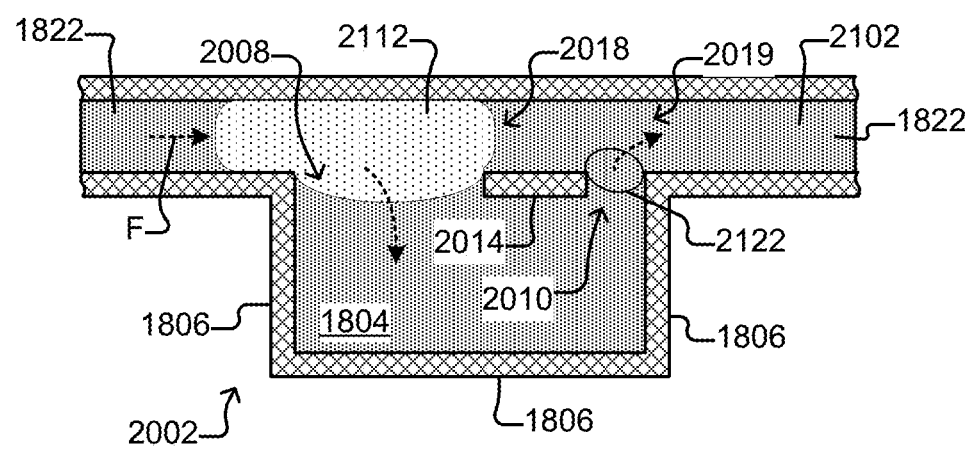
FIG. 21 is an example of the bubble trap of FIG. 20 trapping a bubble according to some embodiments of the invention.

As illustrated in FIG. 21, the trap chamber 1804 can be filled fully or partially with a fluidic medium 2102, which can also be flowed at a rate F in the channel 1822. As a gas bubble 2112 in the medium 2102 passes the first trap opening 2008, the bubble 2112 can preferentially enter the trap chamber 1804 driven by pressure differentials that arise because the size $dt_1$ of the first trap opening 2008 is larger than the size $dc_1$ of the first channel opening 2018 generally as discussed above with respect to FIGS. 18 and 19. The foregoing can displace a volume 2122 of the medium 2102 from the trap chamber 1804 through the second trap opening 2010 into the channel 1822. That the size $dt_2$ of the second trap opening 2010 is smaller than the size $dc_2$ of the second channel opening 2019 can aid in pulling the displaced volume 2122 of medium 2102 from the trap chamber 1804 through the second trap opening 2010 into the channel 1822. Once material from the bubble substantially fills the bubble trap, surface tension between the bubble and its environment will both keep the bubble material in the trap and keep it from exiting the trap via the second trap opening. Any additional bubble material present in the channel 1822 will continue to travel down the channel past both the first and second trap openings 2008, 2010. Additional bubble traps of any suitable design may be placed further downstream along the channel 1822 to capture additional bubble material, whether it is gas or immiscible liquid. In some embodiments, there may be 1, 2, 3, 4, 5, 10, 15, 20, 25, 50 or 100 additional bubble traps located along the channel 1822. The bubble traps may be placed in the microfluidic channel upstream of pens containing micro-objects 702 and prevent bubble material from contacting any micro-object 702 in the microfluidic circuit.

Figure 22:
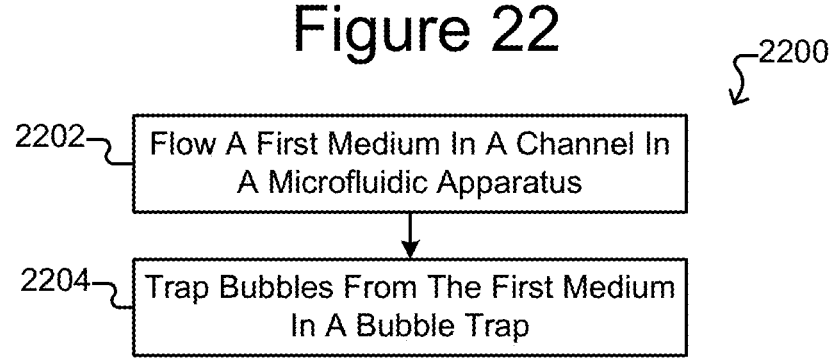
FIG. 22 is an example of a process for trapping a bubble in a flow of fluidic medium in a fluidic channel according to some embodiments of the invention.

FIG. 22 illustrates an example of a process 2200 for trapping gas bubbles in a fluidic fluid flowing in a channel such as the channel 1822 illustrated in FIGS. 18-21. As shown, at step 2202, the process 2200 can flow a fluidic medium (which can contain gas bubbles) in the channel. For example, the medium 1902 can be flowed in the channel 1822 as illustrated in FIG. 19. FIG. 21 illustrates another example in which medium 2102 is flowed in the channel 1822.

At step 2204 of FIG. 22, the process 2200 can trap gas bubbles in the flowing fluidic medium in a bubble trap connected to the channel. For example, the bubble trap 1802 of FIGS. 18 and 19 can trap bubbles like bubble 1912 as discussed above with respect to FIG. 19. As another example, the bubble trap 2002 of FIGS. 20 and 21 can trap bubbles like bubble 2112 as discussed above with respect to FIG. 21. FIG. 22 can include additional steps. For example, the trapped bubbles can be removed from the bubble trap 2002, for example, by pulling the bubbles out of the bubble trap 2002, through a vacuum channel, or the like. In some embodiments, the trapped bubbles are removed from the bubble trap 2002 by pulling the bubble out of the bubble trap 2002 through a filter, which will provide resistance to pulling any other materials besides the bubble material out of the trap.

Figure 23:
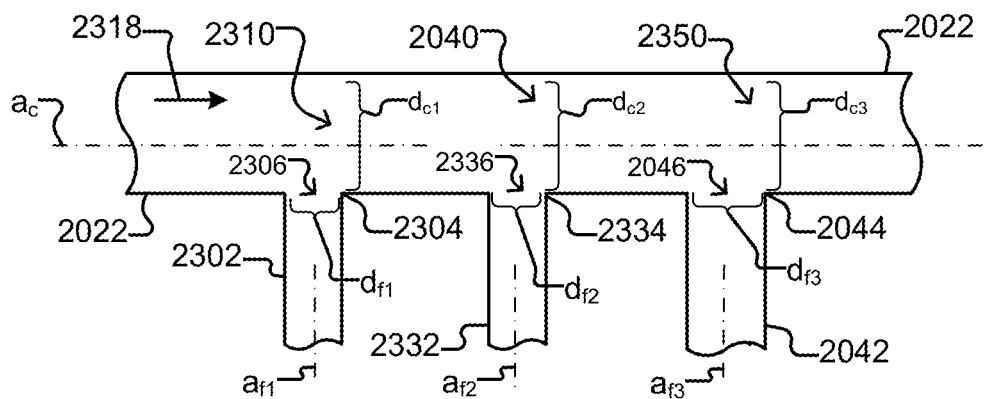
FIG. 23 illustrates an example of one or more feed channels connected to a primary fluidic channel configured to provide substantially bubble-free fluidic medium to the feed channels according to some embodiments of the invention.

FIG. 23 illustrates a partial view of a fluidic primary channel 2322 to which openings 2306, 2336, 2346 of one or more fluidic feed channels 2302, 2332, 2342 (three are shown but there can be fewer or more) are connected. The channels 2302, 2322, 2332, 2342 can be fluidic structures that are part of a fluidic circuit (e.g., like 120) of a microfluidic apparatus (e.g., like 100). The channels 2302, 2322, 2332, 2342 can thus be part of the fluidic circuit 120 of the apparatus 100 of FIGS. 1A and 1B.

As shown, a flow path 2318 of the primary channel 2322 can be oriented along a channel axis $a_c$, and flow paths of each of the feed channels 2302, 2332, 2342 can be oriented along a feed axis $a_{f1}$, $a_{f2}$, $a_{f3}$. As shown, each of the feed axes $a_{f1}$, $a_{f2}$, $a_{f3}$ can be oriented at a non-zero angle with respect to the channel axis $a_c$ such that none of the feed axes $a_{f1}$, $a_{f2}$, $a_{f3}$ is parallel to the channel axis $a_c$. For example, in some embodiments, the feed axes $a_{f1}$, $a_{f2}$, $a_{f3}$ can be substantially parallel with each other but substantially perpendicular to the channel axis $a_c$ as shown in FIG. 23.

As illustrated in FIG. 23, the sizes $d_{f1}$, $d_{f2}$, $d_{f3}$ of the feed openings 2306, 2336, 2346 of the feed channels 2302, 2332, 2342 can be smaller than the sizes $d_{c1}$, $d_{c2}$, $d_{c3}$ of corresponding cross-sections of the primary channel 2322 at outer edges 2304, 2334, 2344 of the feed openings 2306, 2336, 2346. (Hereinafter the cross-sections of the primary channel 2322 at the outer edges 2304, 2334, 2344 of the feed openings 2306, 2336, 2346 to the feed channels 2302, 2332, 2342 are referred to as the primary channel openings 2310, 2340, 2350.) Generally in accordance with the discussion above regarding the larger size $d_t$ of the trap opening 1812 with respect to the size $d_c$ of the channel opening 1814 in FIG. 18, the smaller sizes $d_{f1}$, $d_{f2}$, $d_{f3}$ of the feed channel openings 2306, 2336, 2346 relative to the sizes $d_{c1}$, $d_{c2}$, $d_{c3}$ of the corresponding primary channel openings 2310, 2340, 2350 can result in pressure differentials that tend to keep gas bubbles (not shown) in a flow of fluidic medium (not shown) along the flow path 2318 in the primary channel 2322 and prevent such gas bubbles (not shown) from entering the feed channels 2302, 2332, 2342. In various embodiments, the sizes $d_{c1}$, $d_{c2}$, $d_{c3}$ of the primary channel openings 2310, 2340, 2350 can be, for example, at least one and quarter times larger, at least one and a half times larger, at least two times larger, at least three times larger, at least five times larger, or more than the sizes $d_{f1}$, $d_{f2}$, $d_{f3}$ of the corresponding feed openings 2306, 2336, 2346 of the feed channels 2302, 2332, 2342.

Figure 24:
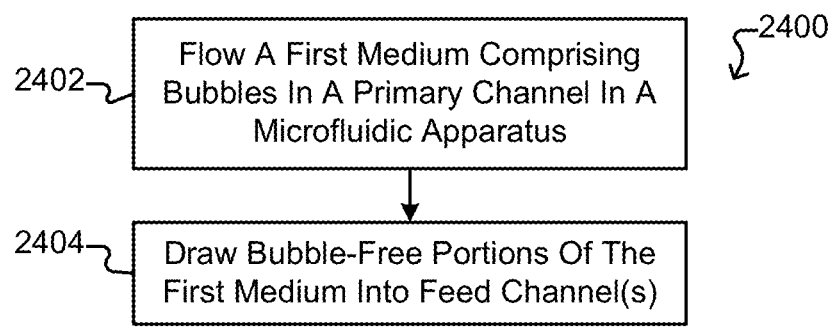
FIG. 24 is an example of a process for providing substantially bubble-free fluidic medium from a primary fluidic channel to one or more feed channels according to some embodiments of the invention.

The configuration illustrated in FIG. 23 can thus be utilized to provide fluidic medium (not shown) that contains gas bubbles flowing in the primary channel 2322 as substantially bubble free fluidic medium (not shown) to one or more feed channels 2302, 2332, 2342 fluidically connected to the primary channel 2322. FIG. 24 illustrates an example of a process 2400 for doing so.

As shown in FIG. 24, at step 2402, the process 2400 can flow a fluidic medium that may contain gas bubbles in a primary fluidic channel 2322 (see FIG. 23). At step 2404, the process 2400 can draw substantially bubble free fluidic medium from the primary channel 2322 into one or more feed channels 2302, 2332, 2342. This can be accomplished due to the smaller relative sizes $d_{f1}$, $d_{f2}$, $d_{f3}$ of the feed channel openings 2306, 2336, 2346 relative to the sizes $d_{c1}$, $d_{c2}$, $d_{c3}$ of the primary channel openings 2306, 2336, 2346 as discussed above.

FIG. 25 is an example of a process 2500 in which biological micro-objects can be cultured in isolated pens of a microfluidic apparatus such as the apparatus 100 of FIGS. 1A and 1B. As shown in FIG. 25, at step 2502, the process 2500 can place a first biological micro-object in a first pen of a microfluidic apparatus, and at step 2504, the process 2500 can place a second biological micro-object in a second pen of the microfluidic apparatus. For example, a first biological micro-object can be placed in one of the pens 126, 136 of the apparatus 100 of FIGS. 1A and 1B, and a second biological micro-object can be placed in another one of the pens 126, 136. As shown in FIGS. 1A and 1B, the first and second pens 126, 136 can be fluidically connected.

The first biological micro-object and the second biological micro-object can be any biological object and/or carrier, on which the biological object is disposed. For example, the first and second biological micro-objects can be biological cells, biological materials, or the like. The first biological micro-object and the second biological micro-object can be placed in pens 126, 136 in any of the ways micro-objects 702 are placed into pens 126, 136 as discussed above with respect to FIG. 7.

At step 2506, the process 2500 can isolate the first pen in which the first biological micro-object was placed at step 2502 from the second pen in which the second biological micro-object was placed at step 2504. The first pen and the second pen can be isolated from each other in any way disclosed herein (e.g., as illustrated in FIGS. 8, 9, 14, 15A, and/or 15B) for isolating one microfluidic structure from another microfluidic structure.

At step 2508, the process 2500 can culture the biological micro-object in the first pen, and at step 2510, the process 2500 can culture the second biological micro-object in the second pen. The steps 2508, 2510 can be performed while the first pen is isolated from the second pen. For example, nutrients (not shown) can be provided to the first and second pens in any way discussed herein. For example, such nutrients can be provided to the first pen and/or the second pen in the same way that material 1702 is provided to an isolated pen 126 as illustrated in FIG. 17. At step 2512, the process 2500 can analyze the first biological micro-object and/or the second biological micro-object after those biological micro-objects have been cultured at steps 2508, 2510. The step of analyzing either the first biological micro-object or the second biological micro-object may include analyzing a biological material produced by the first or second biological micro-object. The biological material produced by the first biological micro-object and the biological materials produced by the second biological micro-object may not be the same type of biological material and analyzing the first biological material may include performing a different analysis than the analysis performed to analyze the second biological material. For one non-limiting example, the first biological material may be a first antibody having a first target and the second biological material may be a second antibody having a different target.

As with all the examples of processes shown in any of the figures, the steps 2502-2512 in FIG. 25 are examples, and variations are possible. For example, the process 2500 can include more steps or fewer steps than shown. As another example, some or all of the steps 2502-2512 can be performed in a different order than shown, and two or more of the steps can be performed simultaneously.

EXPERIMENTAL

System and Microfluidic device for all experiments: Manufactured by Berkeley Lights, Inc. The system includes at least a flow controller, temperature controller, fluidic medium conditioning and pump component, light source for light activated DEP configurations, microfluidic device, mounting stage, and a camera. The fluidic channels and pens of the microfluidic device were fabricated from polydimethylsiloxane (PDMS) bonded to glass and features introduced by soft lithography. The pens of the microfluidic devices shown in the examples have volumes in the range of about $5 \times 10^5$ to $1 \times 10^8$ $\mu m^3$.

Figure 32:
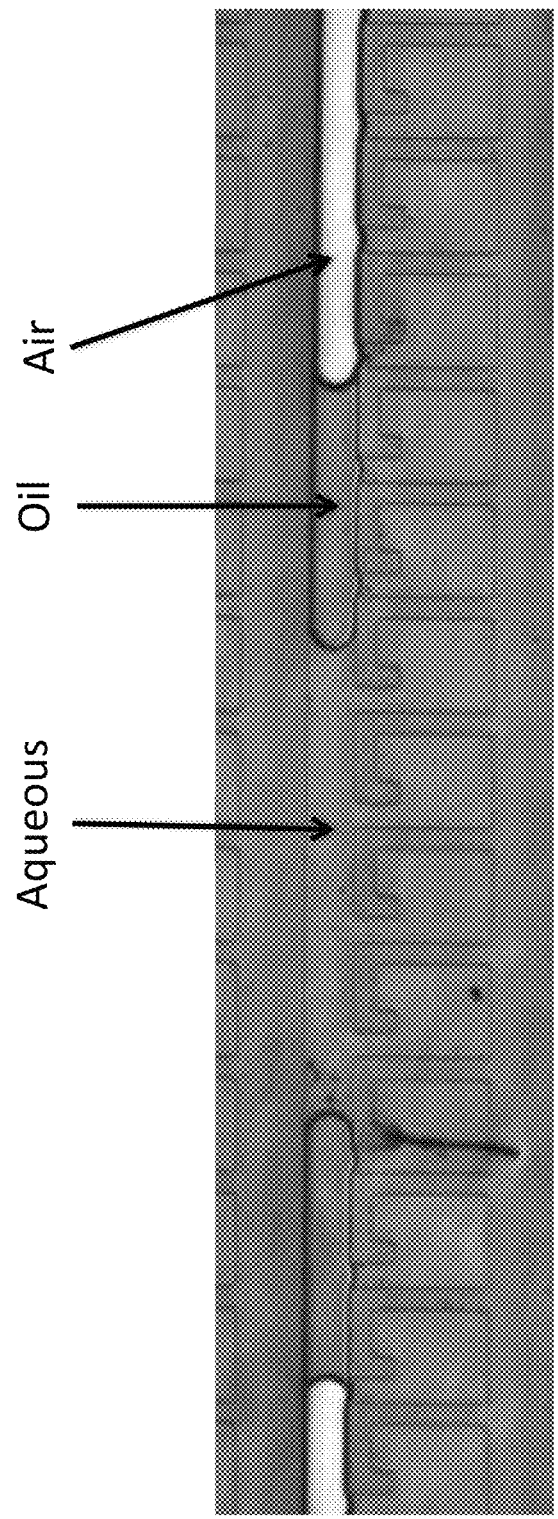
FIG. 32 is a photographic representation of an embodiment of isolating microfluidic structures of the apparatus of FIG. 1 according to some embodiments of the invention.

Example 1. Isolation of Pens Using Progressive Introduction of Immiscible Media in the Fluidic Channel Aqueous medium (deionized water) was flowed into the microfluidic apparatus first, then followed by Fuorinert™ Electronic liquid (FC-3283, 3M, a perfluorinated organic liquid, molecular weight 521) which is a water immiscible medium. Lastly air was flowed into the microfluidic channel. Flow rates were about 0.5 ml/hr. As shown in the photograph of the microfluidic device of FIG. 32, neither the water immiscible fluid, Fluorinert™ FC-3283, nor the air entered the pens. The opening of the pens into the channel is much smaller (width). The height is constant throughout the microfluidic circuit shown. Pens of this microfluidic circuit were isolated from each other and from the aqueous medium in the channel as the fluorinated immiscible fluid and air were flowed into the channel.

Figure 33:
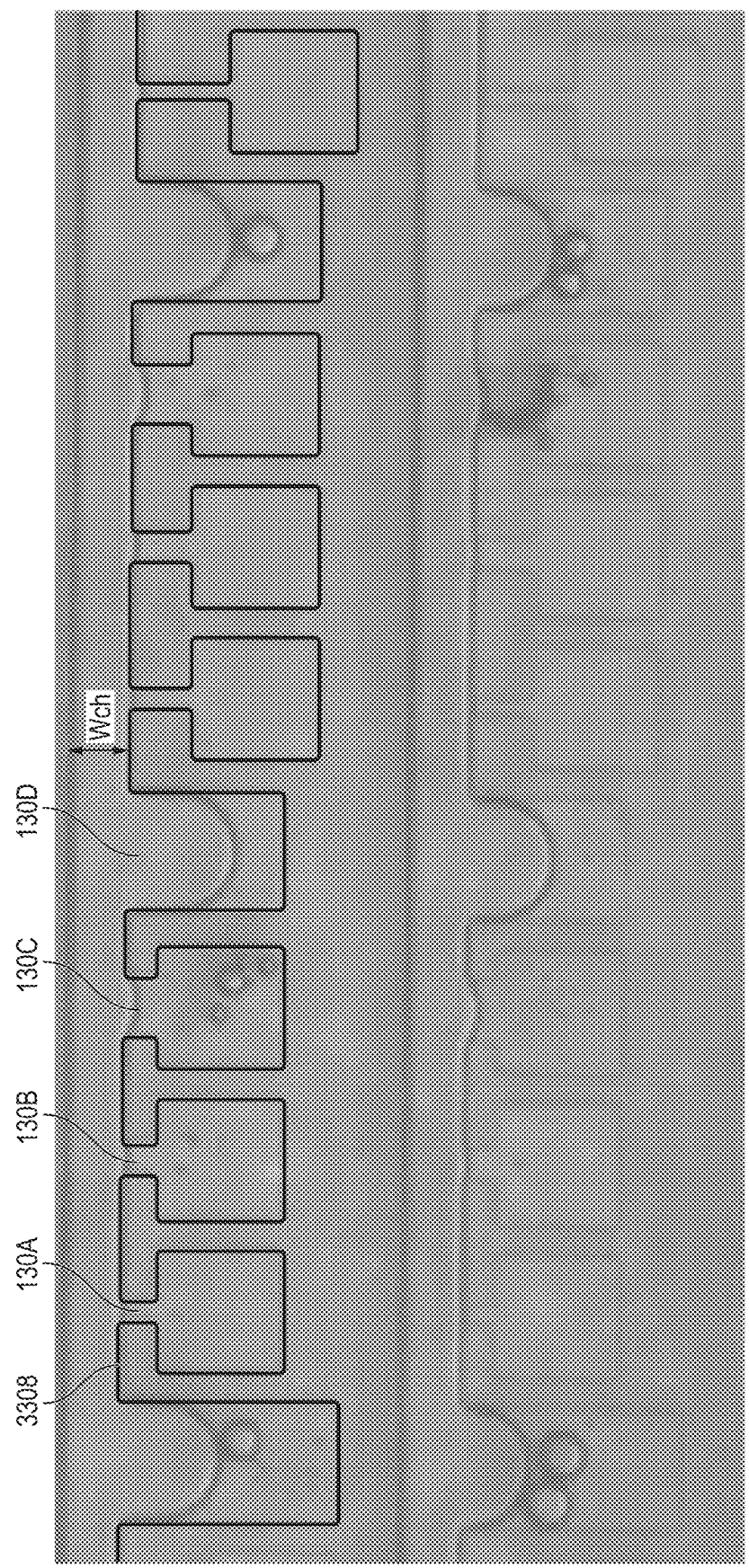
FIG. 33 is a photographic representation with annotations of embodiments of bubble traps according to some embodiments of the invention

Example 2. Isolation of Pens and Bubble Trap Function for Microfluidic Apparatuses A. FIG. 33 shows a photograph of a microfluidic device focused on two parallel channels, each having a fluidic channel of width $W_c$. Along the channel, pens having a range of volumes and a variety of sizes of pen openings 130A, 130B, 130C, 130D are distributed. The boundaries of the pens are annotated in the upper channel for ease of viewing; they are the same as the pens distributed along the channel. Aqueous medium (deionized water) was flowed into the microfluidic channels and filled the pens. Following that, Fuorinert™ Electronic liquid (FC-3283, 3M, a perfluorinated organic liquid, molecular weight 521) which is a water immiscible medium, was flowed into the microfluidic channels at about 0.5 ml·hr. As shown in the photograph of FIG. 33, immiscible Fluorinert™ organic liquid filled the channel, and significantly entered the pen having a pen opening 130D which has a width (constant height in the microfluidic apparatus) much greater than width $W_c$ of the channel. Some bubbles of the immiscible fluid entered the pen having pen opening 130C, which also has a width slightly larger than width $W_c$ of the channel. No bubbles or significant portion of the Fluorinert™ organic liquid entered the pens having openings 130A and 130B, which are significantly narrower than width $W_c$ of the channel. This experiment demonstrates that pens can be effectively isolated from the channel or other pens using immiscible fluid which does not enter pens selectively as designed.

Figure 34:
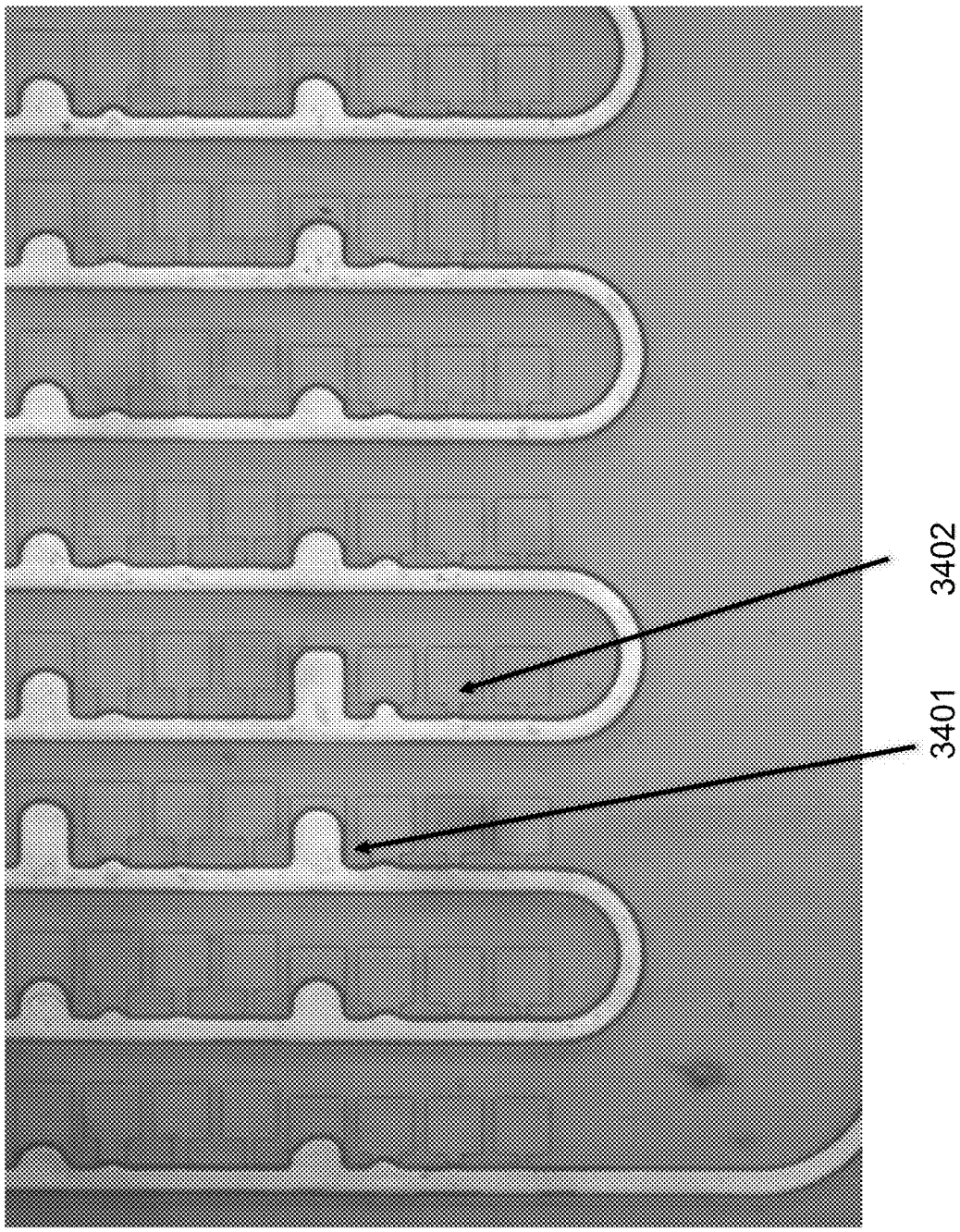
FIG. 34 is a photographic representation of another embodiment of a bubble trap according to some embodiments of the invention.

B. FIG. 34 shows a photograph of a microfluidic apparatus having a long fluidic channel with pens distributed along the channel in between turns in the channel as it traverses the microfluidic chip. As in the above example, different sized pens are aligned along the channel and have different sized pen openings into the channel. Deionized water was flowed into the microfluidic channel, followed by flow of immiscible Fluorinert™ organic liquid. Throughout the entire fluidic channel, pens (for example, 3401) having a large pen opening relative to the width of the fluidic channel (constant height throughout the microfluidic chip) demonstrated significant entry of the immiscible second medium. For pens having a pen opening smaller than that of the channel width (e.g., 3402) no or very little immiscible second fluidic medium entered.

Example 3. Bubble Trap for Microfluidic Apparatuses

Figure 35A:
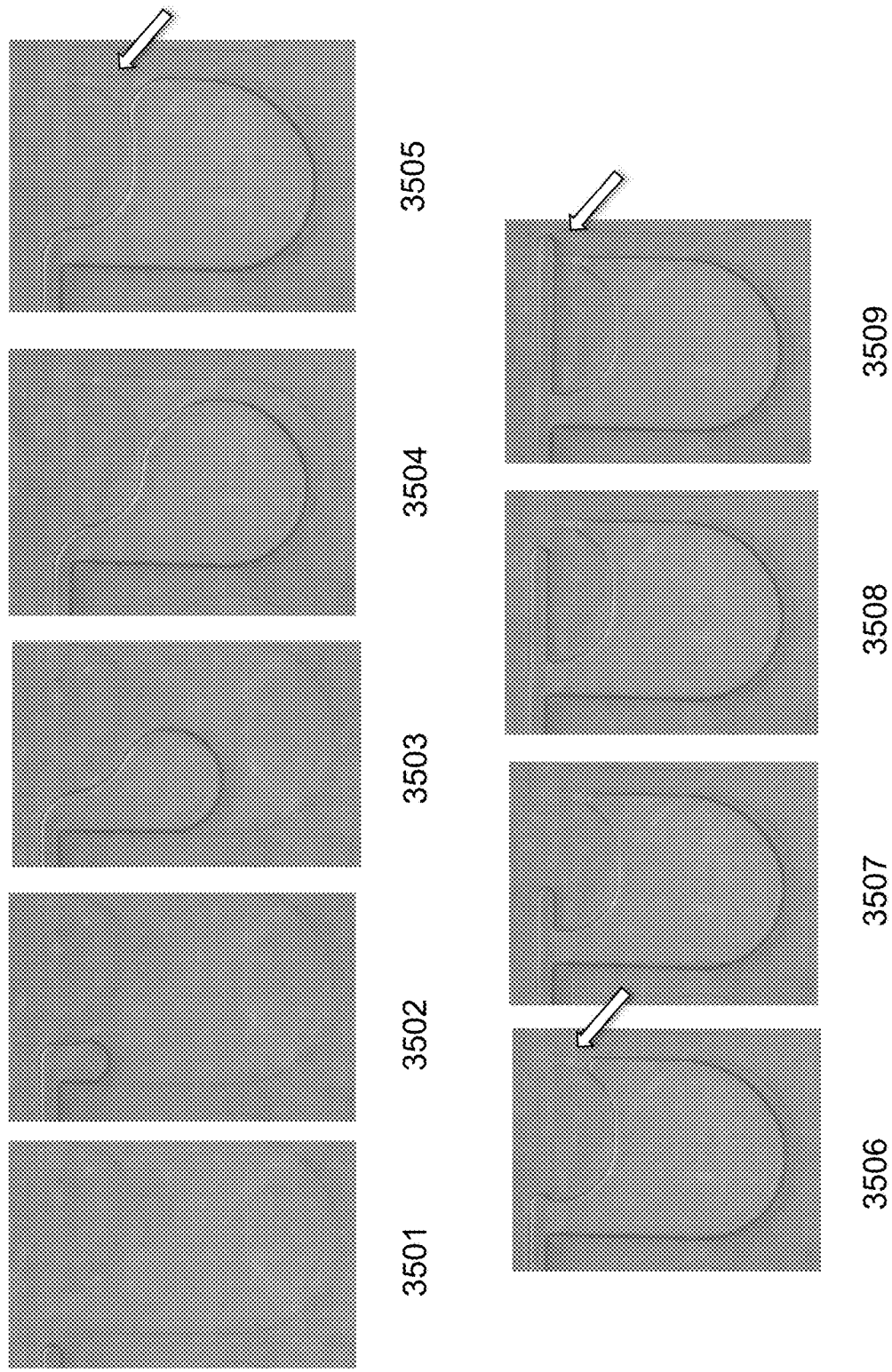
FIGS. 35A and 35B are photographic representations of another embodiment of a bubble trap according to some embodiments of the invention.
Figure 35B:
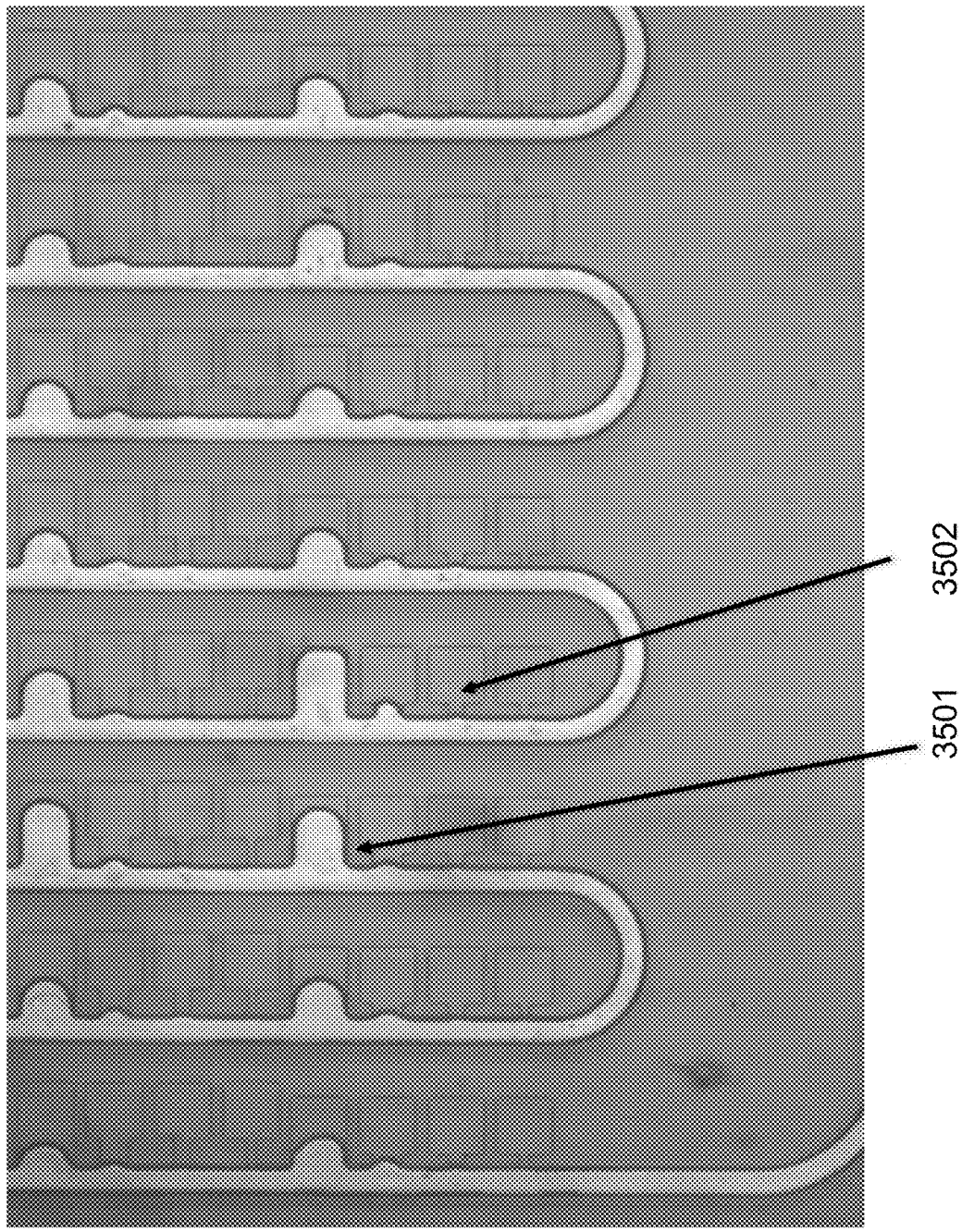

A microfluidic bubble trap was fabricated on a chip using the materials and techniques of the general methods above, and used within the instrumentation described therein. This trap is similar to the bubble trap of FIG. 20, having two openings into the main channel, an upstream opening that is larger than the main channel and a second, downstream opening that is smaller than that of the main channel. An aqueous solution (deionized water) was flowed first through the fluidic channel, which also filled the bubble trap. Flow of immiscible Fluorinert™ organic liquid followed at a rate of about 0.5 ml/hr. FIG. 35 shows a series of photographs at succeeding points in the introduction of the immiscible fluid, which represent flow of unwanted gas or oils within the microfluidic circuit. The photograph at 3501 shows the bubble trap filled entirely with aqueous medium, having the channel mostly filled with aqueous medium as well. Immiscible medium started to approach the bubble trap, but was not yet at the opening to the channel. Photograph 3502 shows the start of flow of immiscible medium into the bubble trap, which entered preferentially into the trap rather than continue down the channel. This occurred as the opening of the upstream opening of the bubble trap is larger than that of the main channel. As discussed above for the bubble trap of FIGS. 18-20, the differences in surface tension acting upon the immiscible medium in the channel as opposed to that acting upon the immiscible medium at the opening to the bubble trap and within the bubble trap create pressure differentials that direct the immiscible medium into the trap. The trap continued to fill as more immiscible fluidic medium continued to flow through the main channel, as is shown at 3503, 3504 and 3505. As the bubble trap filled and approached the second downstream smaller trap opening to the channel (see white arrow at 3505), surface tension no longer drives more immiscible medium into the trap, and immiscible medium resumes flowing down the main channel, past the opening to the trap (see white arrow at 3506 where the immiscible medium stopped filling and immiscible medium started moving past the trap opening.) Photographs 3507, 3508, and 3509 show how the immiscible fluid continued to flow down the main channel. The arrow at 3509 points to a small meniscus of aqueous medium isolated at the second trap opening which remains in place. This experiment demonstrated that one or a series of bubble traps of this design placed in line upstream of pens containing biological cells can capture all unwanted immiscible fluid that may enter the microfluidic channel.

Example 4. Isolation of Microfluidic Pens Using Coated Beads in the Microfluidic Channel Materials: Hyb9.4 cells (ATCC®, HB-10508™) were incubated in 5% carbon dioxide incubator and split every 2-3 days. Labeled anti-CD45 antibody: Goat anti mouse f(ab')2-alexa 568 purchased from Molecular Probes (Thermo Fisher Scientific, Catalog #A11019).

CD45 coated beads: Streptavidin coated beads, diameter 8 μm (Spherotech Cat #SVP-60-5) were coated with CD45 (R&D Systems Cat #1430-CD) as follows. Resuspended carrier free CD45 (50 μg) in 500 μl PBS (Fisher Cat #BP29303), pH 7.2, was coupled to EZ-Link™ NHS-PEG4-Biotin (Pierce Cat #21329). The coupled CD45-PEG4-Biotin was reacted with the streptavidin coated beads to produce the CD45 coated beads.

Culture medium: Serum free hybridoma medium (Life Technologies, Cat #12045-076), with 10% w/w Fetal Bovine Serum (Hyclone, Cat #SH30084.03) and 1% w/w Penicillin-Streptomycin (10,000 U/ml Life Technologies Cat #15140-122) with 5% carbon dioxide saturating headspace of the media reservoir.

Priming: The microfluidic chip having a plurality of pens was primed purging the microfluidic chip with 100% carbon dioxide gas at 15 psi for 5 min. A priming solution which included the culture medium and 1% by weight of Pluronic® F127 nonionic surfactant was flowed for 8 min about 5

μl/sec. The culture medium was then flowed for an additional 5 min at about 5 μl/sec.

The Hyb9.4 cells were loaded by use of DEP forces, in particular, opto-electronic tweezer (OET) manipulation of cells to direct single cells or small groups of cells into individual pens. The cells were cultured for 30 min, with perfusion of culture media at 0.1 ul/s, at 36° C. Culture media was then flushed at 1 ul/s for 5 min, in order to remove any bubbles in the input line, and any secreted antibody that may have diffused into the channel up until this point.

The CD45 coated polystyrene beads and the secondary fluorescent antibody were then flowed in with more medium where the beads were present at a concentration of $1 \times e^6$ beads/ml, and the fluorescent secondary antibody were present at a 1:5000 dilution in the culture medium and the flow was then stopped, leaving the beads and labeled antibody in the fluidic channel.

Figure 36:
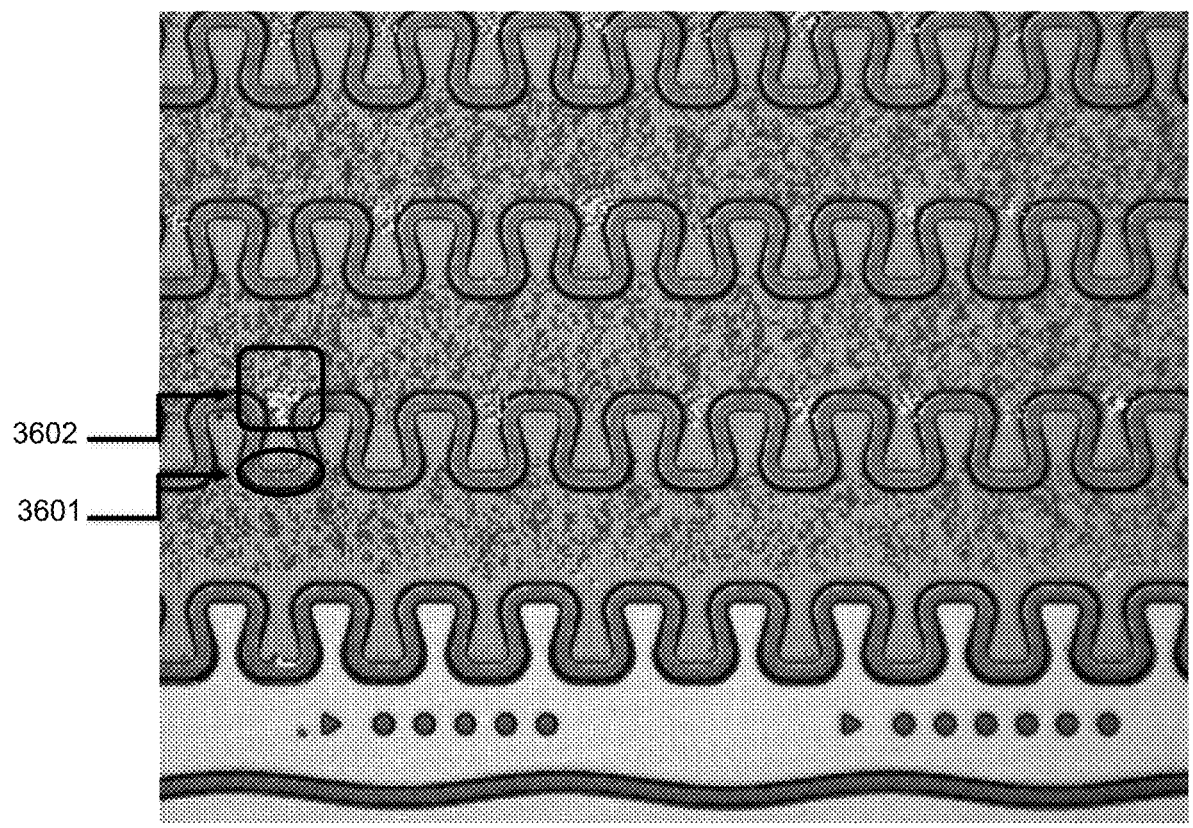
FIG. 36 is a photographic representation of another embodiment of isolating microfluidic structures of FIG. 1 according to some embodiments of the invention.

A. Referring to FIG. 36, the Hyb 9.4 cells remain at the bottom of the pen, as specifically pointed to by the oval 3601. After introducing the cells, and thereafter CD45 coated beads and labeled secondary antibody, the cells expressed an antibody specific to CD45. As the CD45 antibody diffused out of the pen, the antibody was captured by the CD45 coated beads at the pen entrance. The photograph of FIG. 36 was taken at a time between 30-60 post bead/secondary antibody introduction. The labelling shows (see square enclosure 3602 for one particular pen) that the antibodies secreted in the pens by Hyb 9.4 were concentrated at the pen entrance, rather than spreading out and moving throughout the main channel. Therefore, the secreted antibodies were effectively isolated by the coated beads in the channel, close to the entrance to the pen, and were not flowing throughout the channel. The fluorescence is punctuated at the entrance to pens and was not evenly distributed throughout the channel. The beads are effective at capturing secreted substances before diffusion could carry those substances along the channel and into a non-originating pen, thus limiting diffusion of the secreted substances.

B. Referring to FIGS. 37-38, the same experiment was carried out in a different microfluidic circuit arrangement, but with the same materials and protocol. The images shown were taken at different time points after culturing of the Hyb9.4 cells was initiated and after both the coated beads and the secondary antibodies were introduced to the fluidic channel. A first photograph at time=0 (top panel of FIG. 37) showed no fluorescence at all. In the second panel of FIG. 37, a photograph taken at time=30 min, showed initial amounts of fluorescence, centered at the entrance to pens. Three such clusters are noted with white circles around them, but other clusters were beginning to be evident as well. The top panel in FIG. 38, is a photograph taken at time=45 min. More clusters about the pen entrances were clearly visible (marked with white circles) and no general diffuse fluorescence was evident throughout the channel, indicating effective capture of the secreted antibodies. The bottom panel in FIG. 38 is a photograph taken at time=55 in, and increasing concentration at the pen entrances was seen. Again, no general diffuse labelling was seen in the channel, so the coated beads were effectively capturing secreted substances near their point of generation and not permitting systemic diffusion.

Although specific embodiments and applications of the invention have been described in this specification, these embodiments and applications are exemplary only, and many variations are possible.

We claim:

1. A process of operating a microfluidic apparatus, wherein the microfluidic apparatus comprises a flow region comprising a fluidic channel with a size $W_c$, and at least two isolation pens, wherein each of said isolation pens has a single opening with a size $W_o$ to the fluidic channel, and a connector region fluidically connecting said isolation pen to the fluidic channel, wherein the size $W_c$ of the fluidic channel is larger than the size $W_o$ of the opening to each of said isolation pens, the process comprising:
   flowing a first fluidic medium along said fluidic channel;
   disposing a first biological micro-object in the first isolation pen of said at least two isolation pens; and
   fluidically isolating the first isolation pen of said at least two isolation pens from a second isolation pen of said at least two isolation pens, wherein the relationship between the size $W_c$ of the fluidic channel and the size $W_o$ of the opening to each of said isolation pens is configured to reduce exchange of soluble components from said first isolation pen into said second isolation pen.

2. The process of claim 1, wherein flowing said first fluidic medium along said fluidic channel comprises flowing said first fluidic medium past said opening of said first isolation pen and, subsequently, past said opening of said second isolation pen.

3. The process of claim 1, wherein fluidically isolating said first isolation pen from said second isolation pen further comprises flowing a second fluidic medium along said fluidic channel; and, displacing said first fluidic medium in the channel of the microfluidic apparatus.

4. The process of claim 3, wherein said second fluidic medium is immiscible with said first fluidic medium.

5. The process of claim 4, wherein the second fluidic medium is comprised of a non-aqueous solution.

6. The process of claim 5, wherein the second fluidic medium comprises an oil.

7. The process of claim 1, wherein the size $W_o$ of the opening to said first isolation pen opening is a cross-sectional width of about 2 to about 100 microns.

8. The process of claim 7, wherein the size $W_o$ of the opening to said first isolation pen opening is a cross-sectional width of about 30 to about 90 microns.

9. The process of claim 1, wherein the width $W_c$ of the channel at each opening of the at least two isolation pens is about 30 to about 1000 microns.

10. The process of claim 9, wherein the width $W_c$ of the channel at each opening of the at least two isolation pens is about 50 to about 250 microns.

11. The process of claim 1, wherein a linear distance between the openings of the at least two isolation pens to the microfluidic channel is about 60 to about 2500 microns.

12. The process of claim 11, wherein the linear distance between the openings in the at least two isolation pens to the microfluidic channel is about 80 to about 500 microns.

13. The process of claim 1, wherein a height of the channel ($H_{ch}$) at the first isolation pen opening is about 20 to about 100 microns.

14. The process of claim 1, further comprising covalent modification of at least one surface of the channel of the microfluidic apparatus such that the covalent modification generates a surface on the channel that is more hydrophobic than at least one surface of the first isolation pen.

15. The process of claim 1, wherein disposing the biological micro-object comprises generating dielectrophoretic (DEP) forces that move the first biological micro-object into the first isolation pen.

16. The process of claim 1, further comprising disposing a second biological micro-object in the second isolation pen of said microfluidic apparatus.

17. The process of claim 16, wherein fluidically isolating the first isolation pen further comprises isolating the first biological micro-object in the first isolation pen from said second biological micro-object in said second isolation pen by a volume of said second fluidic medium.

18. The process of claim 17, further comprising culturing said second biological micro-object in said second isolation pen.

19. The process of claim 18, wherein the culturing occurs after isolating said first isolation pen from said second isolation pen.

20. The process of claim 19, further comprising analyzing said second biological micro-object in said second isolation pen.

21. The process of claim 20, wherein the analyzing occurs after culturing said second biological micro-object.

22. The process of claim 1, further comprising culturing said first biological micro-object in said first isolation pen.

23. The process of claim 1, further comprising analyzing said first biological micro-object in said first isolation pen.

24. The process of claim 1, wherein each of the at least two isolation pens comprises a volume of at least $1 \times 10^5$ cubic microns.

25. The process of claim 1, wherein the at least two isolation pens each comprise a single opening.

26. The process of claim 1, wherein the opening to each of the at least two isolation pens is perpendicular to a cross-sectional width of the channel.

27. The process of claim 1, wherein the size $W_c$ of the channel is greater than or equal to one and one quarter times the size $W_o$ of the opening of each of the at least two isolation pens.

28. A process of operating a microfluidic apparatus, wherein the microfluidic apparatus comprises a flow region comprising a fluidic channel with a size $W_c$, and at least two isolation pens, wherein each of said isolation pens has a single opening with a size $W_o$ to the fluidic channel, and a connector region comprising the single opening and fluidically connecting said isolation region to the fluidic channel, wherein the size $W_c$ of the fluidic channel is larger than the size $W_o$ of the opening to each of said isolation pens, the process comprising:

flowing a first fluidic medium along said fluidic channel;

disposing a first biological micro-object in the first isolation pen of said at least two isolation pens; and fluidically isolating the first isolation pen of said at least two isolation pens from a second isolation pen of said at least two isolation pens, wherein the relationship between the size $W_c$ of the fluidic channel and the size $W_o$ of the opening to each of said isolation pens is configured to reduce exchange of soluble components from said first isolation pen into said second isolation pen.

* * * * *